(12) United States Patent
Koerber et al.

(10) Patent No.: US 8,597,688 B2
(45) Date of Patent: Dec. 3, 2013

(54) PESTICIDAL MIXTURES COMPRISING ISOXAZOLINE COMPOUNDS II

(75) Inventors: Karsten Koerber, Eppelheim (DE); Florian Kaiser, Mannheim (DE); Egon Haden, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 78 days.

(21) Appl. No.: 13/003,032

(22) PCT Filed: Jul. 2, 2009

(86) PCT No.: PCT/EP2009/058334
§ 371 (c)(1),
(2), (4) Date: Jan. 7, 2011

(87) PCT Pub. No.: WO2010/003877
PCT Pub. Date: Jan. 14, 2010

(65) Prior Publication Data
US 2011/0159107 A1   Jun. 30, 2011

Related U.S. Application Data

(60) Provisional application No. 61/079,311, filed on Jul. 9, 2008.

(51) Int. Cl.
*A01N 59/26* (2006.01)
*A61K 33/42* (2006.01)

(52) U.S. Cl.
USPC .......................................................... 424/605

(58) Field of Classification Search
None
See application file for complete search history.

(56) References Cited

U.S. PATENT DOCUMENTS

| | | | |
|---|---|---|---|
| 3,917,698 | A | 11/1975 | Breslow |
| 6,313,344 | B1 | 11/2001 | Trah et al. |
| 6,521,643 | B1 | 2/2003 | Tomishima et al. |
| 2003/0119806 | A1 | 6/2003 | Lindell et al. |
| 2004/0014801 | A1 | 1/2004 | Cohen et al. |
| 2004/0110637 | A1* | 6/2004 | Ziemer et al. .................. 504/100 |
| 2007/0066617 | A1 | 3/2007 | Mita et al. |
| 2008/0262057 | A1 | 10/2008 | Tisdell et al. |
| 2009/0023923 | A1 | 1/2009 | Mizukoshi et al. |
| 2009/0156643 | A1 | 6/2009 | Mita et al. |
| 2010/0144797 | A1 | 6/2010 | Mita et al. |
| 2010/0144808 | A1 | 6/2010 | Mita et al. |
| 2010/0160683 | A1 | 6/2010 | Matoba et al. |
| 2010/0286175 | A1 | 11/2010 | Grammenos et al. |
| 2011/0172414 | A1 | 7/2011 | Mita et al. |

FOREIGN PATENT DOCUMENTS

| | | |
|---|---|---|
| CA | 2 547 744 | 12/2006 |
| CH | 577487 | 7/1976 |
| CH | 595365 | 2/1978 |
| CH | 608011 | 12/1978 |
| CN | 1 927 860 | 3/2007 |
| DE | 10 2004 010 086 | 9/2004 |
| EP | 0 539 676 | 5/1993 |
| EP | 1 538 138 | 6/2005 |
| EP | 1 731 512 | 12/2006 |
| EP | 1 932 836 | 6/2008 |
| EP | 1 997 813 | 12/2008 |
| EP | 2 151 437 | 2/2010 |
| EP | 2 186 804 | 5/2010 |
| EP | 2 199 287 | 6/2010 |
| JP | 2007/016017 | 1/2007 |
| JP | 2007/106756 | 4/2007 |
| JP | 2007/308471 | 11/2007 |
| JP | 2008/239611 | 10/2008 |
| JP | 2009/108046 | 5/2009 |
| WO | WO 01/17964 | 3/2001 |
| WO | WO 02/068392 | 9/2002 |
| WO | WO 03/022808 | 3/2003 |
| WO | WO 03/062222 | 7/2003 |
| WO | WO 03/067987 | 8/2003 |
| WO | WO 2004/018410 | 3/2004 |
| WO | WO 2004/060371 | 7/2004 |

(Continued)

OTHER PUBLICATIONS

Kiriyama et al., J Pesticide Sci 2003.*

(Continued)

*Primary Examiner* — James H Alstrum Acevedo
*Assistant Examiner* — Thor Nielsen
(74) *Attorney, Agent, or Firm* — Brinks, Hofer, Gilson & Lione

(57) ABSTRACT

The present invention relates to pesticidal mixtures comprising as active components
1) at least one isoxazoline compound I of the formula I

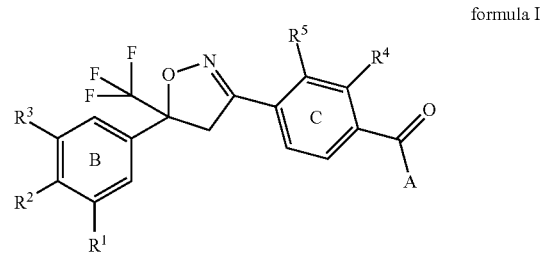

formula I wherein $R^1$, $R^2$, $R^3$, $R^4$, $R^5$ and A are defined as in the description;
and
2) at least one fungicidal compounds II selected from azoles, strobilurins, carboxamides, carbamates, heterocyclic and various other compounds as defined in the description, in synergistically effective amounts.

The invention relates further to methods and use of these mixtures for combating insects, arachnids or nematodes and harmful fungis in and on plants, and for protecting such plants being infested with pests, especially also for protecting seeds.

24 Claims, No Drawings

(56) References Cited

FOREIGN PATENT DOCUMENTS

| | | |
|---|---|---|
| WO | WO 2004/060865 | 7/2004 |
| WO | WO 2005/036961 | 4/2005 |
| WO | WO 2005/085216 | 9/2005 |
| WO | WO 2006/010570 | 2/2006 |
| WO | WO 2006/021833 | 3/2006 |
| WO | WO 2006/065659 | 6/2006 |
| WO | WO 2007/026965 | 3/2007 |
| WO | WO 2007/070606 | 6/2007 |
| WO | WO 2007/074789 | 7/2007 |
| WO | WO 2007/075459 | 7/2007 |
| WO | WO 2007/079162 | 7/2007 |
| WO | WO 2007/081019 | 7/2007 |
| WO | WO 2007/093599 | 8/2007 |
| WO | WO 2007/094313 | 8/2007 |
| WO | WO 2007/105814 | 9/2007 |
| WO | WO 2007/125984 | 11/2007 |
| WO | WO 2008/012027 | 1/2008 |
| WO | WO 2008/019760 | 2/2008 |
| WO | WO 2008/022937 | 2/2008 |
| WO | WO 2008/070831 | 6/2008 |
| WO | WO 2008/108448 | 9/2008 |
| WO | WO 2008/122375 | 10/2008 |
| WO | WO 2008/126665 | 10/2008 |
| WO | WO 2008/130651 | 10/2008 |
| WO | WO 2008/154528 | 12/2008 |
| WO | WO 2009/002809 | 12/2008 |
| WO | WO 2009/005015 | 1/2009 |
| WO | WO 2009/022746 | 2/2009 |
| WO | WO 2009/025983 | 2/2009 |
| WO | WO 2009/035004 | 3/2009 |
| WO | WO 2009/045999 | 4/2009 |
| WO | WO 2009/049846 | 4/2009 |
| WO | WO 2009/077197 | 6/2009 |
| WO | WO 2009/112275 | 9/2009 |
| WO | WO 2009/0126668 | 10/2009 |
| WO | WO 2010/003923 | 1/2010 |
| WO | WO 2010/020521 | 2/2010 |
| WO | WO 2010/020522 | 2/2010 |
| WO | WO 2010/072602 | 7/2010 |
| WO | WO 2010/072781 | 7/2010 |
| WO | WO 2010/112545 | 10/2010 |
| WO | WO 2011/073444 | 2/2011 |

OTHER PUBLICATIONS

International Search Report prepared in International Application No. PCT/EP2009/058334, filed Jul. 2, 2009.

International Preliminary Report on Patentability from corresponding International Application No. PCT/EP2009/058334, filed Jul. 2, 2009.

Belen'Kii et al, Database: Beilstein, XP002580907 database accession No. 1988095, Russian Chem. Bull., (1997), pp. 101-104, vol. 46, No. 1.

"DMP 754 Roxifiban Acetate", Drugs of the Future, (1998), pp. 707-711, vol. 23(7).

Hosking, M., et al., "Roxifiban DuPont", Current Opinion in Cardiovascular, Pulmonary & Renal Investigational Drugs, (2000), pp. 165-171, vol. 2(2).

Kaugars, G. et al., "Miticidal activity of benzoyl chloride phenylhydrazones", Journal of Agriculture and Food Chem., (1973), pp. 647-650, vol. 21, No. 4.

Wierenga, J. et al., "Insecticidal activity of N-arylalkylbenzhydrolpiperidines", Pest Management Science, (2002), pp. 1266-1272, vol. 58.

Walters, Matthew J. et al., "The preparation of 5-Aryl-5-methyl-4,5-dihydroisoxazoles from dilithiated C($\alpha$), O-oximes and Select Acetyl Ketones", Synthetic Communications, 2003, p. 4163-4171, vol.. 33, No. 23.

Office Action dated Dec. 5, 2012, from U.S. Appl. No. 13/003,037.
Office Action dated Jan. 29, 2013, from U.S. Appl. No. 13/141,264.

* cited by examiner

PESTICIDAL MIXTURES COMPRISING ISOXAZOLINE COMPOUNDS II

This application is a National Stage application of International Application No. PCT/EP2009/058334, filed Jul. 2, 2009, which claims the benefit of U.S. Provisional Application No. 61/079,311 filed Jul. 9, 2008, the entire contents of which are hereby incorporated herein by reference.

The present invention relates to mixtures of active ingredients having synergistically enhanced action and to methods comprising applying said mixtures.

One typical problem arising in the field of pest control lies in the need to reduce the dosage rates of the active ingredient in order to reduce or avoid unfavorable environmental or toxicological effects whilst still allowing effective pest control.

Another problem encountered concerns the need to have available pest control agents which are effective against a broad spectrum of pests.

Another problem underlying the present invention is the desire for compositions that improve plants, a process which is commonly and hereinafter referred to as "plant health". For example, advantageous properties that may be mentioned are improved crop characteristics including: emergence, crop yields, protein content, more developed root system, tillering increase, increase in plant height, bigger leaf blade, less dead basal leaves, stronger tillers, greener leaf color, pigment content, photosynthetic activity, less fertilizers needed, less seeds needed, more productive tillers, earlier flowering, early grain maturity, less plant verse (lodging), increased shoot growth, enhanced plant vigor, increased plant stand and early germination; or any other advantages familiar to a person skilled in the art. Methods for improving the health of plants by applying active compounds to the plants or the locus are a general need.

Another difficulty in relation to the use of pesticides is that the repeated and exclusive application of an individual pesticidal compound leads in many cases to a rapid selection of pests which have developed natural or adapted resistance against the active compound in question.

It is also an object of the present invention, with a view to reducing the application rates and broadening the activity spectrum of the active compounds I and II, to provide mixtures which, at a reduced total amount of active compounds applied, have improved activity against harmful fungi and animal pests.

It was therefore an object of the present invention to provide pesticidal mixtures which solve the problems outlined above.

The combating of harmful phytopathogenic fungi is in many regions not the only problem the farmer has to face. Also harmful insects can cause a great damage to crops and other plants. An efficient combination of fungicidal and insecticidal activity is desirable to overcome this problem. Thus, it is a further object of the present invention to provide a mixture which, on the one hand, has good fungicidal activity, and, on the other hand, good insecticidal activity, resulting in a broader pesticidal spectrum of action.

We have found that this object is in part or in whole achieved by the combination of active compounds defined as in the following.

The present invention relates to pesticidal mixtures comprising, as active compounds, 1) as active compound I at least one insecticidal isoxazoline compound of formula I formula I wherein
A is selected from

A-1

A-2

A-3

A-4

A-5

A-6

A-7

A-8 or

-continued

A-9 and wherein # denotes the bond in formula I;

$R^1$, $R^3$ are independently from one another selected from hydrogen, chloro or $CF_3$;

$R^2$ is hydrogen or chloro;

$R^4$ is hydrogen or $CH_3$, $R^5$ is hydrogen, or $R^4$ and $R^5$ are together a bridging 1,3-butadienyl group, which form—together with the aromatic phenylring C they are attached to—a naphtyl ring;

or the tautomers, enantiomers, diastereomers or salts thereof, pure or as mixtures of these, and 2) as active compound II at least one fungicidal compound selected from the groups II.A to II.F:

II.A azoles such as triazoles, imidazoles, pyrazoles, thiazoles and oxazoles selected from the group consisting of azaconazole, benomyl, bitertanol, bromuconazole, carbendazim, cyproconazole, cyazofamid, difenoconazole, diniconazole, diniconazole-M, enilconazole, epoxiconazole, ethaboxam, etridiazole, fluquinconazole, fenbuconazole, flusilazole, flutriafol, fuberidazole, hexaconazole, hymexazole, imazalil, imazalil-sulfphate, imibenconazole, ipconazole, metconazole, myclobutanil, oxpoconazol, paclobutrazol, pefurazoate, penconazole, prochloraz, propiconazole, prothioconazole, simeconazole, triadimefon, triadimenol, tebuconazole, tetraconazole, thiabendazole, triticonazole, triflumizole, uniconazol and 1-(4-chlorophenyl)-2-([1,2,4]triazol-1-yl)-cycloheptanol;

II.B strobilurins selected from the group consisting of azoxystrobin, dimoxystrobin, enestroburin, fluoxastrobin, kresoxim-methyl, methominostrobin, orysastrobin, picoxystrobin, pyraclostrobin, pyribencarb, trifloxystrobin, methyl 2-(ortho-(2,5-dimethylphenyloxymethylene)phenyl)-3-methoxy-acrylate, 2-(2-(6-(3-chloro-2-methyl-phenoxy)-5-fluoro-pyrimidin-4-yloxy)-phenyl)-2-methoxyimino-N-methyl-acetamide and 3-methoxy-2-(2-(N-(4-methoxy-phenyl)-cyclopropanecarboximidoylsulfanylmethyl)-phenyl)-acrylic acid methyl ester;

II.C carboxamides selected from the group consisting of benalaxyl, benalaxyl-M, benodanil, bixafen, boscalid, carboxin, carpropamid, dimethomorph, diclocymet, fenhexamid, fluopyram, flutolanil, furametpyr, flumorph, flumetover, fluopicolide (picobenzamid), mandipropamid, mepronil, metalaxyl, mefenoxam, ofurace, oxadixyl, oxycarboxin, oxytetracyclin, penthiopyrad, silthiofam, thifluzamide, tiadinil, zoxamide, 5-fluoro-1,3-dimethyl-1H-pyrazole-4-carboxylic acid[2-(1,2-dimethylpropyl)-phenyl]-amide, methyl-3-(4-chlorophenyl)-3-(2-isopropoxycarbonylamino-3-methylbutyrylamino) propionate, 2-chloro-N-(1,1,3-trimethyl-indan-4-yl)-nicotinamide, N-(3-ethyl-3,5-5-trimethyl-cyclohexyl)-3-formylamino-2-hydroxy-benzamide, N-(2-{4-[3-(4-chlorophenyl)prop-2-ynyloxy]-3-methoxyphenyl}ethyl)-2-methanesulfonylamino-3-methylbutyramide, N-(2-{4-[3-(4-chlorophenyl)-prop-2-ynyloxy]-3-methoxyphenyl}ethyl)-2-ethanesulfonylamino-3-methyl-butyramide, N-(6-methoxy-pyridin-3-yl)cyclopropane-carboxamide, 2-amino-4-methyl-thiazole-5-carboxamide, N-(2-cyanophenyl)-3,4-dichloroisothiazole-5-carboxamide, N-(4'-bromobiphenyl-2-yl)-4-difluoromethyl-2-methylthiazole-5-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(3',4'-dichloro-5-fluorobiphenyl-2-yl)-3-difluoromethyl-1-methylpyrazole-4-carboxamide; N-(3',4'-dichloro-4-fluorobiphenyl-2-yl)-3-difluoromethyl-1-methylpyrazole-4-carboxamide, N-(3',4'-dichloro-5-fluorobiphenyl-2-yl)-3-difluoromethyl-1-methylpyrazole-4-carboxamide, N-(2-(1,3-dimethylbutyl)-phenyl)-1,3-dimethyl-5-fluoro-1H-pyrazole-4-carboxamide, N-(4'-chloro-3',5-difluoro-biphenyl-2-yl)-3-difluoromethyl-1-methyl-1H-pyrazole-4-carboxamide, N-(4'-chloro-3',5-difluoro-biphenyl-2-yl)-3-trifluoromethyl-1-methyl-1H-pyrazole-4-carboxamide, N-(3',4'-dichloro-5-fluoro-biphenyl-2-yl)-3-trifluoromethyl-1-methyl-1H-pyrazole-4-carboxamide, N-(3',5-difluoro-4'-methyl-biphenyl-2-yl)-3-difluoromethyl-1-methyl-1H-pyrazole-4-carboxamide, N-(3',5-difluoro-4'-methyl-biphenyl-2-yl)-3-trifluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoromethyl-1-methyl-1H-pyrazole-4-carboxamide, N-(2',4'-difluorobiphenyl-2-yl)-1-methyl-3-trifluoromethyl-1H-pyrazole-4-carboxamide, N-(2',4'-dichlorobiphenyl-2-yl)-1-methyl-3-trifluoromethyl-1H-pyrazole-4-carboxamide, N-(2',4'-difluorobiphenyl-2-yl)-3-difluoromethyl-1-methyl-1H-pyrazole-4-carboxamide, N-(2',4'-dichlorobiphenyl-2-yl)-3-difluoromethyl-1-methyl-1H-pyrazole-4-carboxamide, N-(2',5'-difluorobiphenyl-2-yl)-1-methyl-3-trifluoromethyl-1H-pyrazole-4-carboxamide, N-(2',5'-dichlorobiphenyl-2-yl)-1-methyl-3-trifluoromethyl-1H-pyrazole-4-carboxamide, N-(2', difluorobiphenyl-2-yl)-3-difluoromethyl-1-methyl-1H-pyrazole-4-carboxamide, N-(2',5'-dichlorobiphenyl-2-yl)-3-difluoromethyl-1-methyl-1H-pyrazole-4-carboxamide, N-(3',5'-difluorobiphenyl-2-yl)-1-methyl-3-trifluoromethyl-1H-pyrazole-4-carboxamide, N-(3',5'-dichlorobiphenyl-2-yl)-1-methyl-3-trifluoromethyl-1H-pyrazole-4-carboxamide, N-(3',5'-difluorobiphenyl-2-yl)-3-difluoromethyl-1-methyl-1H-pyrazole-4-carboxamide, N-(3',5'-dichlorobiphenyl-2-yl)-3-difluoromethyl-1-methyl-1H-pyrazole-4-carboxamide, N-(3'-fluorobiphenyl-2-yl)-1-methyl-3-trifluoromethyl-1H-pyrazole-4-carboxamide, N-(3'-chlorobiphenyl-2-yl)-1-methyl-3-trifluoromethyl-1H-pyrazole-4-carboxamide; N-(3'-fluorobiphenyl-2-yl)-3-difluoromethyl-1-methyl-1H-pyrazole-4-carboxamide, N-(3'-chlorobiphenyl-2-yl)-3- difluoromethyl-1-methyl-1H-pyrazole-4-carboxamide, N-(2'-fluorobiphenyl-2-yl)-1-methyl-3-trifluoromethyl-1H-pyrazole-4-carboxamide, N-(2'-chlorobiphenyl-2-yl)-1-methyl-3-trifluoromethyl-1H-pyrazole-4-carboxamide, N-(2'-fluorobiphenyl-2-yl)-3-difluoromethyl-1-methyl-1H-pyrazole-4-carboxamide, N-(2'-chlorbiphenyl-2-yl)-3-difluoromethyl-1-methyl-1H-pyrazole-4-carboxamide; N-(2'-fluoro-4'-chloro-5'-methylbiphenyl-2-yl)-1-methyl-3-trifluoromethyl-1H-pyrazole-4-carboxamide, N-(3',4',5'-trifluorobiphenyl-2-yl)-1-methyl-3-trifluoromethyl-1H-pyrazole-4-carboxamide, N-(3',4',5-trifluorobiphenyl-2-yl)-1-methyl-3-difluoromethyl-1H-pyrazole-4-carboxamide, N-(2',4',5'-trifluorobiphenyl-2-yl)-1-methyl-3-difluoromethyl-1H-pyrazole-4-carboxamide, N-(3',4',5-trifluorobiphenyl-2-yl)-3-chlorofluoromethyl-1-methyl-1H-pyrazole-4-carboxamide, N-[2-(1,1,2,3,3,3-hexafluoropropoxy)phenyl]-1-methyl-3-trifluoromethyl-1H-pyrazole-4-carboxamide, N-[2-(1,1,2,3,3,3-hexafluoropropoxy)-phenyl]-3-difluoromethyl-1-methyl-1H-pyrazole-4-carboxamide, N-[2-(2-chloro-1,1,2-trifluoroethoxy)phenyl]-1-methyl-3-trifluoromethyl-1H-pyrazole-4-carboxamide, N-[2-(2-chlor-1,1,2-trifluoroethoxy)phenyl]-3-difluoromethyl-1-methyl-1H-pyrazole-4-carboxamide, N-[2-(1,1,2,2-tetrafluoroethoxy)phenyl]-3-difluoromethyl-1-methyl-1H-pyrazole-4-carboxamide, N-[2-(1,1,2,2-tetrafluoroethoxy)phenyl]-1-methyl-3-trifluoromethyl-1H-pyrazole-4-carboxamide, N-(4'-(trifluoromethylthio)biphenyl-2-yl)-3-difluoromethyl-1-methyl-1H-pyrazole-4-carboxamide, N-(4'-(trifluoromethylthio)biphenyl-2-yl)-1-methyl-3-trifluoromethyl-1H-pyrazole-4-carboxamide and N-(2-Bicycloprop-2-ylphenyl)-3-difluoromethyl-1-methyl-1H-pyrazole-4-carboxamide;

II.D heterocyclic compounds selected from the group consisting of acibenzolar-5-methyl, anilazine, aldimorph, blasticidin-S, bupirimate, captafol, captan, chinomethionat, cyprodinil, dazomet, debacarb, diclomezine, difenzoquat, difenzoquat-methylsulphat, diflumetorim, dodemorph, dodemorph-acetate, famoxadone, fenamidone, fenarimol, ferimzone, fenpiclonil, fenpropidin, fenpropimorph, fludioxonil, fluazinam, fluoroimid, folpet, fenoxanil, iprodione, mepanipyrim, nitrapyrin, nuarimol, octhilinone, oxolinic acid, piperalin, probenazole, procymidone, proquinazid, pyrifenox, pyrimethanil, pyroquilon, quinoxyfen, tricyclazole, triforine, tridemorph, vinclozolin, 5-chloro-7-(4-methylpiperidin-1-yl)-6-(2,4,6-trifluorophenyl)-[1,2,4]triazolo[1,5-a]pyrimidine, 6-(4-tert-butylphenyl)-5-methyl-[1,2,4]triazolo[1,5-a]pyrimidine-7-ylamine, 5-methyl-6-(3,5,5-trimethylhexyl)-[1,2,4]-triazolo[1,5-a]pyrimidine-7-ylamine, 5-methyl-6-octyl-[1,2,4]triazolo[1,5-a]pyrimidine-7-yl-amine, 6-methyl-5-octyl-[1,2,4]triazolo[1,5-a]pyrimidine-7-yl-amine, 6-ethyl-5-octyl-[1,2,4]triazolo[1,5-a]pyrimidine-7-yl-amine, 5-ethyl-6-octyl-[1,2,4]triazolo[1,5-a]pyri-midine-7-ylamine, 5-ethyl-6-(3,5,5-trimethylhexyl)-[1,2,4]-tri-azolo[1,5-a]pyrimi-dine-7-ylamine, 6-octyl-5-propyl-[1,2,4]triazolo[1,5-a]pyrimidine-7-yl-amine, 5-methoxy-methyl-6-octyl-[1,2,4]triazolo[1,5-a]pyrimidine-7-yl-amine, 6-octyl-5-trifluoromethyl-[1,2,4]triazolo[1,5-a]pyrimidine-7-yl-amine and 5-trifluoromethyl-6-(3,5,5-trimethyl-hexyl)-[1,2,4]triazolo[1,5-a]pyrimidine-7-ylamine, 2,3,5,6-tetrachloro-4-methanesulfonyl-pyridine, 3,4,5-trichloropyridine-2,6-di-carbonitrile, N-(1-(5-bromo-3-chloro-pyridin-2-yl)-ethyl)-2,4-dichloro-nicotinamide, N-((5-bromo-3-chloro-pyridin-2-yl)-methyl)-2,4-dichloro-nicotinamide, 2-butoxy-6-iodo-3-propylchromen-4-one and N,N-dimethyl-3-(3-bromo-6-fluoro-2-methylindole-1-sulfonyl)-[1,2,4]triazole-1-sulfonamide;

II.E carbamates selected from the group consisting of diethofencarb, ferbam, flubenthiavalicarb, iprovalicarb, mancozeb, maneb, metam, methasulphocarb, metiram, propamocarb, propamocarb hydrochlorid, propineb, thiram, zineb, ziram, 4-fluorophenyl N-(1-(1-(4-cyanophenyl)ethanesulfonyl)but-2-yl)carbamate, methyl 3-(4-chlorophenyl)-3-(2-isopropoxycarbonylamino-3-methylbutyrylamino)propanoate and carbamate oxime ethers of the formula II$^{E.1}$

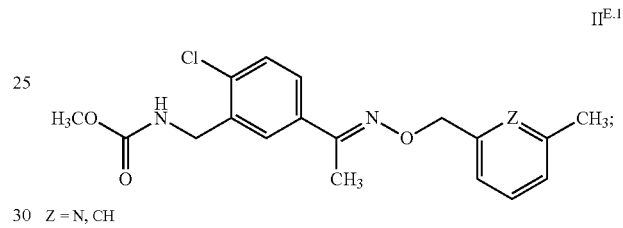

II$^{E.1}$

Z = N, CH

II.F various fungicides selected from the group of antibiotics comprising kasugamycin, kasugamycin-hydrochlorid-hydrat, mildiomycin, streptomycin, polyoxin and validamycin A; the group of nitrophenyl derivatives comprising binapacryl, dinocap, dinobuton, dicloran, nitrothal-isopropyl and tecnazen; the group of sulfur-containing heterocyclyl compounds comprising dithianon and isoprothiolane; the group of organometallic compounds comprising fentin salts; the group of organophosphorus compounds comprising edifenphos, iprobenfos, fosetyl, fosetyl-aluminum, phosphorous acid and its salts, pyrazophos and tolclofos-methyl; the group of organochlorine compounds comprising chlorothalonil, dichlofluanid, dichlorophen, pentachlorophenol and its salts, flusulfamide, hexachlorobenzene, phthalide, pencycuron, quintozene, thiophanate-methyl and tolylfluanid; the group of inorganic active compounds comprising Bordeaux mixture, copper acetate, copper hydroxide, copper oxychloride, basic copper sulfate, oxin-copper and sulfur; and/or selected from a group of various fungicides consisting of biphenyl, bronopol, cyflufenamid, cymoxanil, diphenylamine, dimethirimol, dodine, dodine free base, ethirimol, furalaxyl, iminoctadine, iminoctadine-triacetate, iminoctadine-tris (albesilate), guazatine, guazatine-acetate, metrafenone, prohexadione calcium, spiroxamine guanidine, N-(4-chloro-2-nitro-phenyl)-N-ethyl-4-methylbenzenesulfon-amide, N-(cyclopropylmethoxyimino-(6-difluoromethoxy-2,3-difluorophenyl)-methyl)-2-phenyl acetamide, N'-(4-(4-chloro-3-trifluoromethyl-phenoxy)-2,5-dimethylphenyl)-N-ethyl-N-methyl formamidine, N'-(4-(4-fluoro-3-trifluoromethyl-phenoxy)-2,5-dimethylphenyl)-N-ethyl-N-methyl formamidine, N'-(2- methyl-5-trifluormethyl-4-(3-trimethylsilanyl-propoxy)-phenyl)-N-ethyl-N-methyl formamidine and N'-(5-difluormethyl-2-methyl-4-(3-trimethylsilanyl-propoxy)-phenyl)-N-ethyl-N-methyl formamidine;

in a synergistically effective amount.

Pesticidal active isoxazoline compounds have been described in WO05/085219, WO2007/075459, WO2008/019760 and WO2008/012027. Further isoxazoline compounds comprising annelated bicyclic moieties, as an naphtyl group, are disclosed in WO2007/079162. Preparation methods are described in WO 2007/074789 and WO 2007/094313. In general, pesticidal active isoaxzoline compounds are also described in JP 2007/016017, JP 2007/106756, WO 2005/085216, WO 2007/026965, WO 2007/105814, WO 2007/125984, WO 2007/026965, JP 2008-239611, WO 2008108448, WO 2009/005015, WO 2009/035004, WO 2008/150393, WO 2008/154528, WO 2009/002809, WO 2009/003075, WO 2009/025983, WO 2009/051956, WO 2009/022746, WO 2009/049846, WO 2008/126665, US 2008/00262057 and WO 2009/024541.

The prior art does not disclose pesticidal mixtures comprising selective isoxazoline compounds according to the present invention showing unexpected and synergistic effects in combination with other pesticidically active compounds.

The active compounds II mentioned above of groups II.A to II.F, their preparation and their action against harmful fungi are generally known and they are commercially available.

Benalaxyl, methyl N-(phenylacetyl)-N-(2,6-xylyl)-DL-alaninate (DE 29 03 612); metalaxyl, methyl N-(methoxyacetyl)-N-(2,6-xylyl)-DL-alaninate (GB 15 00 581); ofurace, (RS)-α-(2-chloro-N-2,6-xylylacetamido)-γ-butyrolactone [CAS RN 58810-48-3];

oxadixyl; N-(2,6-dimethylphenyl)-2-methoxy-N-(2-oxo-3-oxazolidinyl)acetamide (GB 20 58 059);

aldimorph, "4-alkyl-2,5(or 2,6)-dimethylmorpholine", comprising 65-75% of 2,6-dimethylmorpholine and 25-35% of 2,5-dimethylmorpholine, comprising more than 85% of 4-dodecyl-2,5(or 2,6)-dimethylmorpholine, where "alkyl" also includes octyl, decyl, tetradecyl and hexadecyl, with a cis/trans ratio of 1:1 [CAS RN 91315-15-0]; dodine, 1-dodecylguanidinium acetate (Plant Dis. Rep., Vol. 41, p. 1029 (1957)); dodemorph, 4-cyclododecyl-2,6-dimethylmorpholine (DE-A1198125); fenpropimorph, (RS)-cis-4-[3-(4-tert-butylphenyl)-2-methylpropyl]-2,6-dimethylmorpholine (DE-A 27 52 096);

fenpropidin, (RS)-1-[3-(4-tert-butylphenyl)-2-methylpropyl]piperidine (DE-A 27 52 096);

guazatine, mixture of the reaction products from the amidation of technical grade iminodi(octamethylene)diamine, comprising various guanidines and polyamines [CAS RN 108173-90-6];

iminoctadine, 1,1'-iminodi(octamethylene)diguanidine (Congr. Plant Pathol., 1., p. 27 (1968);

spiroxamine, (8-tert-butyl-1,4-dioxaspiro[4.5]dec-2-yl)diethylamine (EP-A 281 842);

tridemorph, 2,6-dimethyl-4-tridecylmorpholine (DE-A 11 64 152);

pyrimethanil, 4,6-dimethylpyrimidin-2-ylphenylamine (DD-A 151 404);

mepanipyrim, (4-methyl-6-prop-1-ynylpyrimidin-2-yl)phenylamine (EP-A 224 339);

cyprodinil, (4-cyclopropyl-6-methylpyrimidin-2-yl)phenylamine (EP-A 310 550);

cycloheximide, 4-{(2R)-2-[(1S,3S,5S)-3,5-dimethyl-2-oxocyclohexyl]-2-hydroxyethyl}piperidine-2,6-dione [CAS RN 66-81-9];

griseofulvin, 7-chloro-2',4,6-trimethoxy-6'-methylspiro[benzofuran-2(3H), 1'-cyclohex-2'-ene]-3,4'-dione [CAS RN 126-07-8];

kasugamycin, 3-O-[2-amino-4-[(carboxyliminomethyl)amino]-2,3,4,6-tetradeoxy-α-D-arabino-hexopyranosyl]-D-chiro-inositol [CAS RN 6980-18-3];

natamycin, (8E,14E,16E,18E,20E)-(1R,3S,5R,7R,12R,22R,24S,25R,26S)-22-(3-amino-3,6-dideoxy-β-D-mannopyranosyloxy)-1,3,26-trihydroxy-12-methyl-10-oxo-6,11,28-trioxatricyclo[22.3.1.0$^{5,7}$]octacosa-8,14,16,18,20-pentaene-25-carboxylic acid [CAS RN 7681-93-8];

polyoxin, 5-(2-amino-5-O-carbamoyl-2-deoxy-L-xylonamido)-1-(5-carboxy-1,2,3,4-tetrahydro-2,4-dioxopyrimidin-1-yl)-1,5-dideoxy-β-D-allofuranuronic acid [CAS RN 22976-86-9];

streptomycin, 1,1'-{1-L-(1,3,5/2,4,6)-4-[5-deoxy-2-O-(2-deoxy-2-methylamino-α-L-glucopyranosyl)-3-C-formyl-α-L-lyxofuranosyloxy]-2,5,6-trihydroxycyclohex-1,3-ylene}diguanidine (J. Am. Chem. Soc. Vol. 69, p. 1234 (1947));

bitertanol, β-([1,1'-biphenyl]-4-yloxy)-α-(1,1-dimethylethyl)-1H-1,2,4-triazole-1-ethanol (DE-A 23 24 020);

bromuconazole, 1-[[4-bromo-2-(2,4-dichlorophenyl)tetrahydro-2-furanyl]methyl]-1H-1,2,4-triazole (Proc. 1990 Br. Crop. Prot. Conf.—Pests Dis. Vol. 1, p. 459);

cyproconazole, 2-(4-chlorophenyl)-3-cyclopropyl-1-[1,2,4]triazol-1-ylbutan-2-ol (U.S. Pat. No. 4,664,696);

difenoconazole, 1-{2-[2-chloro-4-(4-chlorophenoxy)phenyl]-4-methyl-[1,3]dioxolan-2-ylmethyl}-1H-[1,2,4]triazole (GB-A 2 098 607);

diniconazole, (β E)-β-[(2,4-dichlorophenyl)methylene]-α-(1,1-dimethylethyl)-1H-1,2,4-triazole-1-ethanol (Noyaku Kagaku, 1983, Vol. 8, p. 575);

enilconazole (imazalil), 1-[2-(2,4-dichlorophenyl)-2-(2-propenyloxy)ethyl]-1H-imidazole (Fruits, 1973, Vol. 28, p. 545);

epoxiconazole, (2RS,3SR)-1-[3-(2-chlorophenyl)-2,3-epoxy-2-(4-fluorophenyl)propyl]-1H-1,2,4-triazole (EP-A 196 038);

fenbuconazole, α-[2-(4-chlorophenyl)ethyl]-α-phenyl-1H-1,2,4-triazole-1-propanenitrile (Proc. 1988 Br. Crop Prot. Conf.—Pests Dis., Vol. 1, p. 33);

fluquinconazole, 3-(2,4-dichlorophenyl)-6-fluoro-2-[1,2,4]-triazol-1-yl-3H-quinazolin-4-one (Proc. Br. Crop Prot. Conf.—Pests Dis., 5-3, 411 (1992));

flusilazole, 1-{[bis(4-fluorophenyl)methylsilanyl]methyl}-1H-[1,2,4]-triazole (Proc. Br. Crop Prot. Conf.—Pests Dis., Vol. 1, p. 413 (1984));

flutriafol, α-(2-fluorophenyl)-α-(4-fluorophenyl)-1H-1,2,4-triazole-1-ethanol (EP-A 15756);

hexaconazole, 2-(2,4-dichlorophenyl)-1-[1,2,4]triazol-1-ylhexan-2-ol (CAS RN 79983-71-4);

ipconazole, 2-[(4-chlorophenyl)methyl]-5-(1-methylethyl)-1-(1H-1,2,4-triazol-1-yl-methyl)cyclopentanol (EP-A 267 778), metconazole, 5-(4-chlorobenzyl)-2,2-dimethyl-1-[1,2,4]-triazol-1-ylmethylcyclopentanol (GB 857 383);

myclobutanil, 2-(4-chlorophenyl)-2-[1,2,4]triazol-1-ylmethylpentanenitrile (CAS RN 88671-89-0);

penconazole, 1-[2-(2,4-dichlorophenyl)pentyl]-1H-[1,2,4] triazole (Pesticide Manual, 12th Ed. 2000, p. 712);

propiconazole, 1-[[2-(2,4-dichlorophenyl)-4-propyl-1,3-dioxolan-2-yl]methyl]-1H-1,2,4-triazole (BE 835 579);

prochloraz, N-(propyl-[2-(2,4,6-trichlorophenoxy)ethyl]) imidazole-1-carboxamide (U.S. Pat. No. 3,991,071);

prothioconazole, 2-[2-(1-chlorocyclopropyl)-3-(2-chlorophenyl)-2-hydroxypropyl]-2,4-dihydro[1,2,4]triazole-3-thione (WO 96/16048);

simeconazole, α-(4-fluorophenyl)-α-[(trimethylsilyl)methyl]-1H-1,2,4-triazole-1-ethanol [CAS RN 149508-90-7];

tebuconazole, 1-(4-chlorophenyl)-4,4-dimethyl-3-[1,2,4]triazol-1-ylmethylpentan-3-ol (EP-A 40 345);

tetraconazole, 1-[2-(2,4-dichlorophenyl)-3-(1,1,2,2-tetrafluoroethoxy)propyl]-1H-1,2,4-triazole (EP-A 234 242);

triadimefon, 1-(4-chlorophenoxy)-3,3-dimethyl-1-(1H-1,2,4-triazol-1-yl)-2-butanone (BE 793 867);

triadimenol, β-(4-chlorophenoxy)-α-(1,1-dimethylethyl)-1H-1,2,4-triazole-1-ethanol (DE-A 3 24 010);

triflumizol, (4-chloro-2-trifluoromethylphenyl)-(2-propoxy-1-[1,2,4]triazol-1-ylethylidene)-amine (JP-A 79/119 462);

triticonazole, (5E)-5-[(4-chlorophenyl)methylene]-2,2-dimethyl-1-(1H-1,2,4-triazol-1-ylmethyl)cyclopentanol (FR 26 41 277);

iprodione, N-isopropyl-3-(3,5-dichlorophenyl)-2,4-dioxoimidazolidine-1-carboxamide (GB 13 12 536);

myclozolin, (RS)-3-(3,5-dichlorophenyl)-5-methoxymethyl-5-methyl-1,3-oxazolidine-2,4-dione [CAS RN 54864-61-8];

procymidone, N-(3,5-dichlorophenyl)-1,2-dimethylcyclopropane-1,2-dicarboximide (U.S. Pat. No. 3,903,090);

vinclozolin, 3-(3,5-dichlorophenyl)-5-methyl-5-vinyloxazolidine-2,4-dione (DE-A 22 07 576), ferbam, iron(3+) dimethyldithiocarbamate (U.S. Pat. No. 1,972,961);

nabam, disodium ethylenebis(dithiocarbamate) (U.S. Pat. No. 2,317,765);

maneb, manganese ethylenebis(dithiocarbamate) (U.S. Pat. No. 2,504,404);

mancozeb, manganese ethylenebis(dithiocarbamate) polymer complex zinc salt (GB 996 264);

metam, methyldithiocarbaminic acid (U.S. Pat. No. 2,791,605);

metiram, zinc ammoniate ethylenebis(dithiocarbamate) (U.S. Pat. No. 3,248,400);

propineb, zinc propylenebis(dithiocarbamate) polymer (BE 611 960);

polycarbamate, bis(dimethylcarbamodithioato-κS,κS')[μ-[[1,2-ethanediylbis[carbamodithioato-κS,κS']](2-)]]di[zinc] [CAS RN 64440-88-6];

thiram, bis(dimethylthiocarbamoyl) disulfide (DE-A 642 532);

ziram, dimethyldithiocarbamate [CAS RN 137-30-4];

zineb, zinc ethylenebis(dithiocarbamate) (U.S. Pat. No. 2,457,674);

anilazine, 4,6-dichloro-N-(2-chlorophenyl)-1,3,5-triazine-2-amine (U.S. Pat. No. 2,720,480);

benomyl, N-butyl-2-acetylaminobenzimidazole-1-carboxamide (U.S. Pat. No. 3,631,176);

boscalid, 2-chloro-N-(4'-chlorobiphenyl-2-yl)nicotinamide (EP-A 545 099);

carbendazim, methyl (1H-benzimidazol-2-yl)carbamate (U.S. Pat. No. 3,657,443);

carboxin, 5,6-dihydro-2-methyl-N-phenyl-1,4-oxathiine-3-carboxamide (U.S. Pat. No. 3,249,499);

oxycarboxin, 5,6-dihydro-2-methyl-1,4-oxathiine-3-carboxanilide 4,4-dioxide (U.S. Pat. No. 3,399,214);

cyazofamid, 4-chloro-2-cyano-N,N-dimethyl-5-(4-methylphenyl)-1H-imidazole-1-sulfonamide (CAS RN 120116-88-3];

dazomet, 3,5-dimethyl-1,3,5-thiadiazinane-2-thione (Bull. Soc. Chim. Fr. Vol. 15, p. 891 (1897));

diflufenzopyr, 2-{1-[4-(3,5-difluorophenyl)semicarbazono]ethyl}nicotinic acid [CAS RN 109293-97-2];

dithianon, 5,10-dioxo-5,10-dihydronaphtho[2,3-b][1,4]dithiin-2,3-dicarbonitrile (GB 857 383);

famoxadone, (RS)-3-anilino-5-methyl-5-(4-phenoxyphenyl)-1,3-oxazolidine-2,4-dione [CAS RN 131807-57-3];

fenamidone, (S)-1-anilino-4-methyl-2-methylthio-4-phenylimidazolin-5-one [CAS RN 161326-34-7];

fenarimol, α-(2-chlorophenyl)-α-(4-chlorophenyl)-5-pyrimidinemethanol (GB 12 18 623);

fuberidazole, 2-(2-furanyl)-1H-benzimidazole (DE-A 12 09 799);

flutolanil, α,α,α-trifluoro-3'-isopropoxy-o-toluanilide (JP 1104514);

furametpyr, 5-chloro-N-(1,3-dihydro-1,1,3-trimethyl-4-isobenzofuranyl)-1,3-dimethyl-1H-pyrazole-4-carboxamide [CAS RN 123572-88-3];

isoprothiolane, diisopropyl 1,3-dithiolan-2-ylidenemalonate (Proc. Insectic. Fungic. Conf. 8. Vol. 2, p. 715 (1975));

mepronil, 3'-isopropoxy-o-toluanilide (U.S. Pat. No. 3,937,840);

nuarimol, α-(2-chlorophenyl)-α-(4-fluorophenyl)-5-pyrimidinemethanol (GB 12 18 623);

fluopicolide (picobenzamid), 2,6-dichloro-N-(3-chloro-5-trifluoromethylpyridin-2-ylmethyl)benzamide (WO 99/42447);

probenazole, 3-allyloxy-1,2-benzothiazole 1,1-dioxide (Agric. Biol. Chem. Vol. 37, p. 737 (1973));

proquinazid, 6-iodo-2-propoxy-3-propylquinazolin-4(3H)-one (WO 97/48684);

pyrifenox, 2',4'-dichloro-2-(3-pyridyl)acetophenone (EZ)—O-methyloxime (EP 49 854);

pyroquilon, 1,2,5,6-tetrahydropyrrolo[3,2,1-ij]quinolin-4-one (GB 139 43 373)

quinoxyfen, 5,7-dichloro-4-(4-fluorophenoxy)quinoline (U.S. Pat. No. 5,240,940);

silthiofam, N-allyl-4,5-dimethyl-2-(trimethylsilyl)thiophene-3-carboxamide [CAS RN 175217-20-6];

thiabendazole, 2-(1,3-thiazol-4-yl)benzimidazole (U.S. Pat. No. 3,017,415);

thifluzamide, 2',6'-dibromo-2-methyl-4'-trifluoromethoxy-4-trifluoromethyl-1,3-thiazole-5-carboxanilide [CAS RN 130000-40-7];

thiophanate-methyl, 1,2-phenylenebis(iminocarbonothioyl)bis(dimethylcarbamate) (DE-A 19 30 540);

tiadinil, 3'-chloro-4,4'-dimethyl-1,2,3-thiadiazole-5-carboxanilide [CAS RN 223580-51-6];

tricyclazole, 5-methyl-1,2,4-triazolo[3,4-b][1,3]benzothiazole [CAS RN 41814-78-2];

triforine, N,N'-{piperazine-1,4-diylbis[(trichloromethyl)methylene]}diformamide (DE-A 19 01 421);

5-chloro-7-(4-methylpiperidin-1-yl)-6-(2,4,6-trifluorophenyl)-[1,2,4]-triazolo[1,5-a]pyrimidine (WO 98/46607) and other triazolo pyrimidine (EP-A 71 792; EP-A 141 317; WO 2003/009687; WO 2005/087771; WO 2005/087772; WO 2005/087773; WO 2006/087325; WO 2006/092428);

Bordeaux mixture, mixture of $CuSO_4 \times 3Cu(OH)_2 \times 3CaSO_4$ [CAS RN 8011-63-0]

copper acetate, $Cu(OCOCH_3)_2$ [CAS RN 8011-63-0];

copper oxychloride, $Cu_2Cl(OH)_3$ [CAS RN 1332-40-7];

basic copper sulfate, $CuSO_4$ [CAS RN 1344-73-6];

binapacryl, (RS)-2-sec-butyl-4,6-dinitrophenyl 3-methylcrotonate [CAS RN 485-31-4];

dinocap, mixture of 2,6-dinitro-4-octylphenylcrotonate and 2,4-dinitro-6-octylphenylcrotonate, where "octyl" is a mixture of 1-methylheptyl, 1-ethylhexyl and 1-propylpentyl (U.S. Pat. No. 2,526,660);

dinobuton, (RS)-2-sec-butyl-4,6-dinitrophenyl isopropyl carbonate [CAS RN 973-21-7];

nitrothal-isopropyl, diisopropyl 5-nitroisophthalate (Proc. Br. Insectic. Fungic. Conf. 7., Vol. 2, p. 673 (1973));

fenpiclonil, 4-(2,3-dichlorophenyl)-1H-pyrrole-3-carbonitrile (Proc. 1988 Br. Crop Prot. Conf.—Pests Dis., Vol. 1, p. 65);

fludioxonil, 4-(2,2-difluorobenzo[1,3]dioxol-4-yl)-1H-pyrrole-3-carbonitrile (The Pesticide Manual, publ. The British Crop Protection Council, 10th ed. 1995, p. 482);

acibenzolar-5-methyl, methyl 1,2,3-benzothiadiazole-7-carbothioate [CAS RN 135158-54-2];

flubenthiavalicarb (benthiavalicarb), isopropyl {(S)-1-[(1R)-1-(6-fluorobenzothiazol-2-yl)-ethylcarbamoyl]-2-methylpropyl}carbamate (JP-A 09/323,984);

carpropamid, 2,2-dichloro-N-[1-(4-chlorophenyl)ethyl]-1-ethyl-3-methylcyclopropane-carboxamide [CAS RN 104030-54-8];

chlorothalonil, 2,4,5,6-tetrachloroisophthalonitrile (U.S. Pat. No. 3,290,353);

cyflufenamid, (Z)—N-[α-(cyclopropylmethoxyimino)-2,3-difluoro-6-(trifluoromethyl)benzyl]-2-phenylacetamide (WO 96/19442);

cymoxanil, 1-(2-cyano-2-methoxyiminoacetyl)-3-ethylurea (U.S. Pat. No. 3,957,847);

diclomezine, 6-(3,5-dichlorophenyl-p-tolyl)pyridazin-3(2H)-one (U.S. Pat. No. 4,052,395)

diclocymet, (RS)-2-cyano-N—[(R)-1-(2,4-dichlorophenyl)ethyl]-3,3-dimethylbutyramide [CAS RN 139920-32-4];

diethofencarb, isopropyl 3,4-diethoxycarbanilate (EP-A 78 663);

edifenphos, O-ethyl S,S-diphenyl phosphorodithioate (DE-A 14 93 736)

ethaboxam, N-(cyano-2-thienylmethyl)-4-ethyl-2-(ethylamino)-5-thiazolecarboxamide (EP-A 639 574);

fenhexamid, N-(2,3-dichloro-4-hydroxyphenyl)-1-methylcyclohexanecarboxamide (Proc. Br. Crop Prot. Conf.—Pests Dis., 1998, Vol. 2, p. 327);

fentin-acetate, triphenyltin (U.S. Pat. No. 3,499,086);

fenoxanil, N-(1-cyano-1,2-dimethylpropyl)-2-(2,4-dichlorophenoxy)propanamide (EP-A 262 393);

ferimzone, (Z)-2'-methylacetophenone-4,6-dimethylpyrimidin-2-ylhydrazone [CAS RN 89269-64-7];

fluazinam, 3-chloro-N-[3-chloro-2,6-dinitro-4-(trifluoromethyl)phenyl]-5-(trifluoromethyl)-2-pyridinamine (The Pesticide Manual, publ. The British Crop Protection Council, 10th ed. (1995), p. 474);

fosetyl, fosetyl-aluminum, ethylphosphonate (FR 22 54 276);

iprovalicarb, isopropyl[(1S)-2-methyl-1-(1-p-tolylethylcarbamoyl)propyl]carbamate (EP-A 472 996);

hexachlorobenzene (C. R. Seances Acad. Agric. Fr., Vol. 31, p. 24 (1945));

mandipropamid, (RS)-2-(4-chlorophenyl)-N-[3-methoxy-4-(prop-2-ynyloxy)phenethyl]-2-(prop-2-ynyloxy)acetamide (WO 03/042166);

metrafenone, 3'-bromo-2,3,4,6'-tetramethoxy-2',6-dimethylbenzophenone (U.S. Pat. No. 5,945,567);

pencycuron, 1-(4-chlorobenzyl)-1-cyclopentyl-3-phenylurea (DE-A 27 32 257);

penthiopyrad, (RS)—N-[2-(1,3-dimethylbutyl)-3-thienyl]-1-methyl-3-(trifluoromethyl)-1H-pyrazole-4-carboxamide (JP 10/130,268);

propamocarb, isopropyl 3-(dimethylamino)propylcarbamate (DE-A 15 67 169);

phthalide (DE-A 16 43 347);

toloclofos-methyl, O-2,6-dichloro-p-tolyl-O,O-dimethyl phosphorothioate (GB 14 67 561);

quintozene, pentachloronitrobenzene (DE-A 682 048);

zoxamide, (RS)-3,5-dichloro-N-(3-chloro-1-ethyl-1-methyl-2-oxopropyl)-p-toluamide [CAS RN 156052-68-5];

captafol, N-(1,1,2,2-tetrachloroethylthio)cyclohex-4-ene-1,2-dicarboximide (Phytopathology, Vol. 52, p. 754 (1962));

captan, N-(trichloromethylthio)cyclohex-4-ene-1,2-dicarboximide (U.S. Pat. No. 2,553,770);

dichlofluanid, N-dichlorofluoromethylthio-N,N-dimethyl-N-phenylsulfamide (DE-A 11 93 498);

folpet, N-(trichloromethylthio)phthalimide (U.S. Pat. No. 2,553,770);

tolylfluanid, N-dichlorofluoromethylthio-N,N-dimethyl-N-p-tolylsulfamide (DE-A 11 93 498);

dimethomorph, 3-(4-chlorophenyl)-3-(3,4-dimethoxyphenyl)-1-morpholin-4-yl-propenone (EP-A 120 321);

flumetover, 2-(3,4-dimethoxyphenyl)-N-ethyl-α,α,α-trifluoro-N-methyl-p-toluamide [AGROW no. 243, 22 (1995)];

flumorph, 3-(4-fluorophenyl)-3-(3,4-dimethoxyphenyl)-1-morpholin-4-ylpropenone (EP-A 860 438);

N-(4'-bromobiphenyl-2-yl)-4-difluoromethyl-2-methylthiazole-5-carboxamide,

N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide (WO 03/66610);

N-(3',4'-dichloro-4-fluorobiphenyl-2-yl)-3-difluoromethyl-1-methylpyrazole-4-carboxamide and N-(3',4'-dichloro-5-fluorobiphenyl-2-yl)-3-difluoromethyl-1-methylpyrazole-4-carboxamide (WO 03/70705);

N-(2-cyanophenyl)-3,4-dichloroisothiazole-5-carboxamide (WO 99/24413);

N-(2-(4-[3-(4-chlorophenyl)prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide (WO 04/49804);

N-(2-Bicycloprop-2-ylphenyl)-3-difluoromethyl-1-methyl-1H-pyrazole-4-carboxamide is a mixture of the diastereomers N-(trans-2-bicycloprop-2-ylphenyl)-3-difluoromethyl-1-methyl-1H-pyrazole-4-carboxamide and N-(cis-2-bicycloprop-2-ylphenyl)-3-difluoromethyl-1-methyl-1H-pyrazole-4-carboxamide (WO 03/074491 and WO 2006/015866);

3-[5-(4-chlorophenyl)-2,3-dimethylisoxazolidin-3-yl]pyridine (EP-A 10 35 122);

2-butoxy-6-iodo-3-propylchromen-4-one (WO 03/14103);

N,N-dimethyl-3-(3-bromo-6-fluoro-2-methylindole-1-sulfonyl)-[1,2,4]triazole-1-sulfonamide (EP-A 10 31 571);

methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate (EP-A 12 01 648);

methyl 3-(4-chlorophenyl)-3-(2-isopropoxycarbonylamino-3-methylbutyrylamino)propionate (EP-A 10 28 125);

azoxystrobin, methyl 2-{2-[6-(2-cyano-1-vinylpenta-1,3-dienyloxy)pyrimidin-4-yloxy]phenyl}-3-methoxyacrylate (EP-A 382 375), dimoxystrobin, (E)-2-(methoxyimino)-N-methyl-2-[α-(2,5-xylyloxy)-o-tolyl]acetamide (EP-A 477 631);

fluoxastrobin, (E)-{2-[6-(2-chlorophenoxy)-5-fluoropyrimidin-4-yloxy]phenyl}(5,6-dihydro-1,4,2-dioxazin-3-yl)methanone O-methyloxime (WO 97/27189);

kresoxim-methyl, methyl (E)-methoxyimino[α-(o-tolyloxy)-o-tolyl]acetate (EP-A 253 213);

metominostrobin, (E)-2-(methoxyimino)-N-methyl-2-(2-phenoxyphenyl)acetamide (EP-A 398 692);

orysastrobin, (2E)-2-(methoxyimino)-2-{2-[(3E,5E,6E)-5-(methoxyimino)-4,6-dimethyl-2,8-dioxa-3,7-diazanona-3,6-dien-1-yl]phenyl}-N-methylacetamide (WO 97/15552);

picoxystrobin, methyl 3-methoxy-2-[2-(6-trifluoromethylpyridin-2-yloxymethyl)phenyl]acrylate (EP-A 278 595);
pyraclostrobin, methyl N-{2-[1-(4-chlorophenyl)-1H-pyrazol-3-yloxymethyl]phenyl}(N-methoxy)carbamate (WO 96/01256);
trifloxystrobin, methyl (E)-methoxyimino-{(E)-α-[1-(α,α,α-trifluoro-m-tolyl)ethylideneaminooxy]-o-tolyl}acetate (EP-A 460 575);
methyl 2-[ortho-(2,5-dimethylphenyloxymethylene)phenyl]-3-methoxyacrylate (EP-A 226 917);
5-chloro-7-(4-methylpiperidin-1-yl)-6-(2,4,6-trifluorophenyl)-[1,2,4]triazolo[1,5-a]pyrimidine (WO 98/46608);
3,4-dichloro-N-(2-cyanophenyl)isothiazole-5-carboxamide (WO 99/24413), compounds of the formula III (WO 04/049804);
N-(2-(4-[3-(4-chlorophenyl)prop-2-ynyloxy]-3-methoxyphenyl)ethyl)-2-methanesulfonylamino-3-methylbutyramide and N-(2-(4-[3-(4-chlorophenyl)prop-2-ynyloxy]-3-methoxyphenyl)ethyl)-2-ethanesulfonylamino-3-methylbutyramide (WO 03/66609);
2-butoxy-6-iodo-3-propylchromen-4-one (WO 03/14103);
N,N-dimethyl-3-(3-bromo-6-fluoro-2-methylindole-1-sulfonyl)-[1,2,4]triazole-1-sulfonamide (WO 03/053145);
methyl 3-(4-chlorophenyl)-3-(2-isopropoxycarbonylamino-3-methylbutyrylamino) propanoate (EP-A 1028125).

We have accordingly found that several objects can be achieved by the mixtures, defined at the outset, of the active compounds I and II. Moreover, we have found that simultaneous, that is joint or separate, application of at least one compound I and at least one of the active compounds II or successive application of at least one of the compound(s) I and at least one of the active compounds II allows better control of harmful fungi than is possible with the individual compounds alone (synergistic mixtures).

Moreover, the present invention relates to:
agricultural compositions comprising a mixture of at least one active compound I and at least one active compound II;
the use of a mixture of at least one active compound I and at least one active compound II for combating animal pests;
the use of a mixture of at least one active compound I and at least one active compound II for combating phytopathogenic harmful fungi;
a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of a mixture of at least one active compound I and at least one active compound II;
a method for protecting crops from attack or infestation by animal pests and/or phythopathogenic harmful fungi, which comprises contacting a crop with a mixture of at least one active compound I and at least one active compound II;
a method for the protection of seeds from soil insects and of the seedlings' roots and shoots from soil and foliar insects and/or phythopathogenic harmful fungi comprising contacting the seeds before sowing and/or after pregermination with a mixture of at least one active compound I and at least one active compound II;
and
seeds comprising a mixture of at least one active compound I and at least one active compound II.

The compounds I can be used as synergists for a large number of different fungicidal active compounds. By simultaneous, that is joint or separate, application of compound(s) I with at least one active compound II, the fungicidal and/or insecticidal activity is increased in a superadditive manner.

The compounds I can be present in different crystal modifications, which may differ in biological activity.

Preferences

Preferences of Insecticidal Isoxazoline Compound I of Formula I

With regard to their use in the pesticidal mixtures of the present invention, compounds I of formula I are preferred, wherein
A is A-1, A-4 or A-6;
$R^1$, $R^3$ are independently from one another selected from hydrogen, chloro or $CF_3$;
$R^2$ is hydrogen or chloro;
$R^4$ is hydrogen or $CH_3$,
$R^5$ is hydrogen or
$R^4$ and $R^5$ are together a bridging 1,3-butadienyl group, which form—together with the aromatic phenylring C they are attached to—a naphtyl ring.

Especially preferred are compounds I of formula I having the following meanings:
A is A-1, A-4 or A-6;
$R^1$, $R^2$, $R^3$ are chloro;
$R^4$ is hydrogen or $CH_3$,
$R^5$ is hydrogen or
$R^4$ and $R^5$ are together a bridging 1,3-butadienyl group, which form—together with the aromatic phenylring C they are attached to—a naphtyl ring.

Especially preferred are compounds I of formula I having the following meanings:
A is A-1, A-4 or A-6;
$R^1$, $R^3$ are chloro;
$R^2$ is hydrogen;
$R^4$ is hydrogen or $CH_3$,
$R^5$ is hydrogen or
$R^4$ and $R^5$ are together a bridging 1,3-butadienyl group, which form—together with the aromatic phenylring C they are attached to—a naphtyl ring.

Mostly preferred are compounds I of formula (I) have the following meanings:
A is A-6;
$R^1$, $R^3$ are chloro;
$R^2$ is hydrogen;
$R^4$ is $CH_3$,
$R^5$ is hydrogen
or
$R^4$ and $R^5$ are together a bridging 1,3-butadienyl group, which form—together with the aromatic phenylring C they are attached to—a naphtyl ring;

Further preferred are compounds I of formula I having the following meanings:
A is A-1, A-4 or A-6;
$R^1$, $R^3$ are $CF_3$;
$R^2$ is hydrogen;
$R^4$ is hydrogen for $CH_3$,
$R^5$ is hydrogen or
$R^4$ and $R^5$ are together a bridging 1,3-butadienyl group, which form—together with the aromatic phenylring C they are attached to—a naphtyl ring
or
A is A-1, A-4 or A-6;
$R^1$ is $CF_3$;
$R^2$, $R^3$ are hydrogen;
$R^4$ is hydrogen for $CH_3$, $R^5$ is hydrogen or $R^4$ and $R^5$ are together a bridging 1,3-butadienyl group, which form—together with the aromatic phenylring C they are attached to—a naphtyl ring.

Examples of the insecticidal isoxazoline compound I of formula I are given in the following table C.I.1.

TABLE C.I.1

| Compound I | A | $R^1$ | $R^2$ | $R^3$ | $R^4$ | $R^5$ |
|---|---|---|---|---|---|---|
| C.I-1 | A-1 | H | H | H | H | H |
| C.I-2 | A-2 | H | H | H | H | H |
| C.I-3 | A-3 | H | H | H | H | H |
| C.I-4 | A-4 | H | H | H | H | H |
| C.I-5 | A-5 | H | H | H | H | H |
| C.I-6 | A-6 | H | H | H | H | H |
| C.I-7 | A-7 | H | H | H | H | H |
| C.I-8 | A-8 | H | H | H | H | H |
| C.I-9 | A-9 | H | H | H | H | H |
| C.I-10 | A-1 | H | Cl | H | H | H |
| C.I-11 | A-2 | H | Cl | H | H | H |
| C.I-12 | A-3 | H | Cl | H | H | H |
| C.I-13 | A-4 | H | Cl | H | H | H |
| C.I-14 | A-5 | H | Cl | H | H | H |
| C.I-15 | A-6 | H | Cl | H | H | H |
| C.I-16 | A-7 | H | Cl | H | H | H |
| C.I-17 | A-8 | H | Cl | H | H | H |
| C.I-18 | A-9 | H | Cl | H | H | H |
| C.I-19 | A-1 | Cl | H | H | H | H |
| C.I-20 | A-2 | Cl | H | H | H | H |
| C.I-21 | A-3 | Cl | H | H | H | H |
| C.I-22 | A-4 | Cl | H | H | H | H |
| C.I-23 | A-5 | Cl | H | H | H | H |
| C.I-24 | A-6 | Cl | H | H | H | H |
| C.I-25 | A-7 | Cl | H | H | H | H |
| C.I-26 | A-8 | Cl | H | H | H | H |
| C.I-27 | A-9 | Cl | H | H | H | H |
| C.I-28 | A-1 | Cl | Cl | H | H | H |
| C.I-29 | A-2 | Cl | Cl | H | H | H |
| C.I-30 | A-3 | Cl | Cl | H | H | H |
| C.I-31 | A-4 | Cl | Cl | H | H | H |
| C.I-32 | A-5 | Cl | Cl | H | H | H |
| C.I-33 | A-6 | Cl | Cl | H | H | H |
| C.I-34 | A-7 | Cl | Cl | H | H | H |
| C.I-35 | A-8 | Cl | Cl | H | H | H |
| C.I-36 | A-9 | Cl | Cl | H | H | H |
| C.I-37 | A-1 | $CF_3$ | H | H | H | H |
| C.I-38 | A-2 | $CF_3$ | H | H | H | H |
| C.I-39 | A-3 | $CF_3$ | H | H | H | H |
| C.I-40 | A-4 | $CF_3$ | H | H | H | H |
| C.I-41 | A-5 | $CF_3$ | H | H | H | H |
| C.I-42 | A-6 | $CF_3$ | H | H | H | H |
| C.I-43 | A-7 | $CF_3$ | H | H | H | H |
| C.I-44 | A-8 | $CF_3$ | H | H | H | H |
| C.I-45 | A-9 | $CF_3$ | H | H | H | H |
| C.I-46 | A-1 | $CF_3$ | Cl | H | H | H |
| C.I-47 | A-2 | $CF_3$ | Cl | H | H | H |
| C.I-48 | A-3 | $CF_3$ | Cl | H | H | H |
| C.I-49 | A-4 | $CF_3$ | Cl | H | H | H |
| C.I-50 | A-5 | $CF_3$ | Cl | H | H | H |
| C.I-51 | A-6 | $CF_3$ | Cl | H | H | H |
| C.I-52 | A-7 | $CF_3$ | Cl | H | H | H |
| C.I-53 | A-8 | $CF_3$ | Cl | H | H | H |
| C.I-54 | A-9 | $CF_3$ | Cl | H | H | H |
| C.I-55 | A-1 | H | H | Cl | H | H |
| C.I-56 | A-2 | H | H | Cl | H | H |
| C.I-57 | A-3 | H | H | Cl | H | H |
| C.I-58 | A-4 | H | H | Cl | H | H |
| C.I-59 | A-5 | H | H | Cl | H | H |
| C.I-60 | A-6 | H | H | Cl | H | H |
| C.I-61 | A-7 | H | H | Cl | H | H |
| C.I-62 | A-8 | H | H | Cl | H | H |
| C.I-63 | A-9 | H | H | Cl | H | H |
| C.I-64 | A-1 | H | Cl | Cl | H | H |
| C.I-65 | A-2 | H | Cl | Cl | H | H |
| C.I-66 | A-3 | H | Cl | Cl | H | H |
| C.I-67 | A-4 | H | Cl | Cl | H | H |
| C.I-68 | A-5 | H | Cl | Cl | H | H |
| C.I-69 | A-6 | H | Cl | Cl | H | H |
| C.I-70 | A-7 | H | Cl | Cl | H | H |
| C.I-71 | A-8 | H | Cl | Cl | H | H |
| C.I-72 | A-9 | H | Cl | Cl | H | H |
| C.I-73 | A-1 | Cl | H | Cl | H | H |
| C.I-74 | A-2 | Cl | H | Cl | H | H |
| C.I-75 | A-3 | Cl | H | Cl | H | H |
| C.I-76 | A-4 | Cl | H | Cl | H | H |
| C.I-77 | A-5 | Cl | H | Cl | H | H |
| C.I-78 | A-6 | Cl | H | Cl | H | H |
| C.I-79 | A-7 | Cl | H | Cl | H | H |
| C.I-80 | A-8 | Cl | H | Cl | H | H |
| C.I-81 | A-9 | Cl | H | Cl | H | H |
| C.I-82 | A-1 | Cl | Cl | Cl | H | H |
| C.I-83 | A-2 | Cl | Cl | Cl | H | H |
| C.I-84 | A-3 | Cl | Cl | Cl | H | H |
| C.I-85 | A-4 | Cl | Cl | Cl | H | H |
| C.I-86 | A-5 | Cl | Cl | Cl | H | H |
| C.I-87 | A-6 | Cl | Cl | Cl | H | H |
| C.I-88 | A-7 | Cl | Cl | Cl | H | H |
| C.I-89 | A-8 | Cl | Cl | Cl | H | H |
| C.I-90 | A-9 | Cl | Cl | Cl | H | H |
| C.I-91 | A-1 | $CF_3$ | H | Cl | H | H |
| C.I-92 | A-2 | $CF_3$ | H | Cl | H | H |
| C.I-93 | A-3 | $CF_3$ | H | Cl | H | H |
| C.I-94 | A-4 | $CF_3$ | H | Cl | H | H |
| C.I-95 | A-5 | $CF_3$ | H | Cl | H | H |
| C.I-96 | A-6 | $CF_3$ | H | Cl | H | H |
| C.I-97 | A-7 | $CF_3$ | H | Cl | H | H |
| C.I-98 | A-8 | $CF_3$ | H | Cl | H | H |
| C.I-99 | A-9 | $CF_3$ | H | Cl | H | H |
| C.I-100 | A-1 | $CF_3$ | Cl | Cl | H | H |
| C.I-101 | A-2 | $CF_3$ | Cl | Cl | H | H |
| C.I-102 | A-3 | $CF_3$ | Cl | Cl | H | H |
| C.I-103 | A-4 | $CF_3$ | Cl | Cl | H | H |
| C.I-104 | A-5 | $CF_3$ | Cl | Cl | H | H |
| C.I-105 | A-6 | $CF_3$ | Cl | Cl | H | H |
| C.I-106 | A-7 | $CF_3$ | Cl | Cl | H | H |
| C.I-107 | A-8 | $CF_3$ | Cl | Cl | H | H |
| C.I-108 | A-9 | $CF_3$ | Cl | Cl | H | H |
| C.I-109 | A-1 | H | H | $CF_3$ | H | H |
| C.I-110 | A-2 | H | H | $CF_3$ | H | H |
| C.I-111 | A-3 | H | H | $CF_3$ | H | H |
| C.I-112 | A-4 | H | H | $CF_3$ | H | H |
| C.I-113 | A-5 | H | H | $CF_3$ | H | H |
| C.I-114 | A-6 | H | H | $CF_3$ | H | H |
| C.I-115 | A-7 | H | H | $CF_3$ | H | H |
| C.I-116 | A-8 | H | H | $CF_3$ | H | H |
| C.I-117 | A-9 | H | H | $CF_3$ | H | H |
| C.I-118 | A-1 | H | Cl | $CF_3$ | H | H |
| C.I-119 | A-2 | H | Cl | $CF_3$ | H | H |
| C.I-120 | A-3 | H | Cl | $CF_3$ | H | H |
| C.I-121 | A-4 | H | Cl | $CF_3$ | H | H |
| C.I-122 | A-5 | H | Cl | $CF_3$ | H | H |
| C.I-123 | A-6 | H | Cl | $CF_3$ | H | H |
| C.I-124 | A-7 | H | Cl | $CF_3$ | H | H |
| C.I-125 | A-8 | H | Cl | $CF_3$ | H | H |
| C.I-126 | A-9 | H | Cl | $CF_3$ | H | H |
| C.I-127 | A-1 | Cl | H | $CF_3$ | H | H |
| C.I-128 | A-2 | Cl | H | $CF_3$ | H | H |
| C.I-129 | A-3 | Cl | H | $CF_3$ | H | H |
| C.I-130 | A-4 | Cl | H | $CF_3$ | H | H |
| C.I-131 | A-5 | Cl | H | $CF_3$ | H | H |
| C.I-132 | A-6 | Cl | H | $CF_3$ | H | H |
| C.I-133 | A-7 | Cl | H | $CF_3$ | H | H |
| C.I-134 | A-8 | Cl | H | $CF_3$ | H | H |
| C.I-135 | A-9 | Cl | H | $CF_3$ | H | H |
| C.I-136 | A-1 | Cl | Cl | $CF_3$ | H | H |
| C.I-137 | A-2 | Cl | Cl | $CF_3$ | H | H |
| C.I-138 | A-3 | Cl | Cl | $CF_3$ | H | H |
| C.I-139 | A-4 | Cl | Cl | $CF_3$ | H | H |
| C.I-140 | A-5 | Cl | Cl | $CF_3$ | H | H |
| C.I-141 | A-6 | Cl | Cl | $CF_3$ | H | H |
| C.I-142 | A-7 | Cl | Cl | $CF_3$ | H | H |
| C.I-143 | A-8 | Cl | Cl | $CF_3$ | H | H |
| C.I-144 | A-9 | Cl | Cl | $CF_3$ | H | H |
| C.I-145 | A-1 | $CF_3$ | H | $CF_3$ | H | H |
| C.I-146 | A-2 | $CF_3$ | H | $CF_3$ | H | H |
| C.I-147 | A-3 | $CF_3$ | H | $CF_3$ | H | H |

TABLE C.I.1-continued

| Compound I | A | R¹ | R² | R³ | R⁴ | R⁵ |
|---|---|---|---|---|---|---|
| C.I-148 | A-4 | CF₃ | H | CF₃ | H | H |
| C.I-149 | A-5 | CF₃ | H | CF₃ | H | H |
| C.I-150 | A-6 | CF₃ | H | CF₃ | H | H |
| C.I-151 | A-7 | CF₃ | H | CF₃ | H | H |
| C.I-152 | A-8 | CF₃ | H | CF₃ | H | H |
| C.I-153 | A-9 | CF₃ | H | CF₃ | H | H |
| C.I-154 | A-1 | CF₃ | Cl | CF₃ | H | H |
| C.I-155 | A-2 | CF₃ | Cl | CF₃ | H | H |
| C.I-156 | A-3 | CF₃ | Cl | CF₃ | H | H |
| C.I-157 | A-4 | CF₃ | Cl | CF₃ | H | H |
| C.I-158 | A-5 | CF₃ | Cl | CF₃ | H | H |
| C.I-159 | A-6 | CF₃ | Cl | CF₃ | H | H |
| C.I-160 | A-7 | CF₃ | Cl | CF₃ | H | H |
| C.I-161 | A-8 | CF₃ | Cl | CF₃ | H | H |
| C.I-162 | A-9 | CF₃ | Cl | CF₃ | H | H |
| C.I-163 | A-1 | H | H | H | CH₃ | H |
| C.I-164 | A-2 | H | H | H | CH₃ | H |
| C.I-165 | A-3 | H | H | H | CH₃ | H |
| C.I-166 | A-4 | H | H | H | CH₃ | H |
| C.I-167 | A-5 | H | H | H | CH₃ | H |
| C.I-168 | A-6 | H | H | H | CH₃ | H |
| C.I-169 | A-7 | H | H | H | CH₃ | H |
| C.I-170 | A-8 | H | H | H | CH₃ | H |
| C.I-171 | A-9 | H | H | H | CH₃ | H |
| C.I-172 | A-1 | H | Cl | H | CH₃ | H |
| C.I-173 | A-2 | H | Cl | H | CH₃ | H |
| C.I-174 | A-3 | H | Cl | H | CH₃ | H |
| C.I-175 | A-4 | H | Cl | H | CH₃ | H |
| C.I-176 | A-5 | H | Cl | H | CH₃ | H |
| C.I-177 | A-6 | H | Cl | H | CH₃ | H |
| C.I-178 | A-7 | H | Cl | H | CH₃ | H |
| C.I-179 | A-8 | H | Cl | H | CH₃ | H |
| C.I-180 | A-9 | H | Cl | H | CH₃ | H |
| C.I-181 | A-1 | Cl | H | H | CH₃ | H |
| C.I-182 | A-2 | Cl | H | H | CH₃ | H |
| C.I-183 | A-3 | Cl | H | H | CH₃ | H |
| C.I-184 | A-4 | Cl | H | H | CH₃ | H |
| C.I-185 | A-5 | Cl | H | H | CH₃ | H |
| C.I-186 | A-6 | Cl | H | H | CH₃ | H |
| C.I-187 | A-7 | Cl | H | H | CH₃ | H |
| C.I-188 | A-8 | Cl | H | H | CH₃ | H |
| C.I-189 | A-9 | Cl | H | H | CH₃ | H |
| C.I-190 | A-1 | Cl | Cl | H | CH₃ | H |
| C.I-191 | A-2 | Cl | Cl | H | CH₃ | H |
| C.I-192 | A-3 | Cl | Cl | H | CH₃ | H |
| C.I-193 | A-4 | Cl | Cl | H | CH₃ | H |
| C.I-194 | A-5 | Cl | Cl | H | CH₃ | H |
| C.I-195 | A-6 | Cl | Cl | H | CH₃ | H |
| C.I-196 | A-7 | Cl | Cl | H | CH₃ | H |
| C.I-197 | A-8 | Cl | Cl | H | CH₃ | H |
| C.I-198 | A-9 | Cl | Cl | H | CH₃ | H |
| C.I-199 | A-1 | CF₃ | H | H | CH₃ | H |
| C.I-200 | A-2 | CF₃ | H | H | CH₃ | H |
| C.I-201 | A-3 | CF₃ | H | H | CH₃ | H |
| C.I-202 | A-4 | CF₃ | H | H | CH₃ | H |
| C.I-203 | A-5 | CF₃ | H | H | CH₃ | H |
| C.I-204 | A-6 | CF₃ | H | H | CH₃ | H |
| C.I-205 | A-7 | CF₃ | H | H | CH₃ | H |
| C.I-206 | A-8 | CF₃ | H | H | CH₃ | H |
| C.I-207 | A-9 | CF₃ | H | H | CH₃ | H |
| C.I-208 | A-1 | CF₃ | Cl | H | CH₃ | H |
| C.I-209 | A-2 | CF₃ | Cl | H | CH₃ | H |
| C.I-210 | A-3 | CF₃ | Cl | H | CH₃ | H |
| C.I-211 | A-4 | CF₃ | Cl | H | CH₃ | H |
| C.I-212 | A-5 | CF₃ | Cl | H | CH₃ | H |
| C.I-213 | A-6 | CF₃ | Cl | H | CH₃ | H |
| C.I-214 | A-7 | CF₃ | Cl | H | CH₃ | H |
| C.I-215 | A-8 | CF₃ | Cl | H | CH₃ | H |
| C.I-216 | A-9 | CF₃ | Cl | H | CH₃ | H |
| C.I-217 | A-1 | H | H | Cl | CH₃ | H |
| C.I-218 | A-2 | H | H | Cl | CH₃ | H |
| C.I-219 | A-3 | H | H | Cl | CH₃ | H |
| C.I-220 | A-4 | H | H | Cl | CH₃ | H |
| C.I-221 | A-5 | H | H | Cl | CH₃ | H |
| C.I-222 | A-6 | H | H | Cl | CH₃ | H |
| C.I-223 | A-7 | H | H | Cl | CH₃ | H |
| C.I-224 | A-8 | H | H | Cl | CH₃ | H |
| C.I-225 | A-9 | H | H | Cl | CH₃ | H |
| C.I-226 | A-1 | H | Cl | Cl | CH₃ | H |
| C.I-227 | A-2 | H | Cl | Cl | CH₃ | H |
| C.I-228 | A-3 | H | Cl | Cl | CH₃ | H |
| C.I-229 | A-4 | H | Cl | Cl | CH₃ | H |
| C.I-230 | A-5 | H | Cl | Cl | CH₃ | H |
| C.I-231 | A-6 | H | Cl | Cl | CH₃ | H |
| C.I-232 | A-7 | H | Cl | Cl | CH₃ | H |
| C.I-233 | A-8 | H | Cl | Cl | CH₃ | H |
| C.I-234 | A-9 | H | Cl | Cl | CH₃ | H |
| C.I-235 | A-1 | Cl | H | Cl | CH₃ | H |
| C.I-236 | A-2 | Cl | H | Cl | CH₃ | H |
| C.I-237 | A-3 | Cl | H | Cl | CH₃ | H |
| C.I-238 | A-4 | Cl | H | Cl | CH₃ | H |
| C.I-239 | A-5 | Cl | H | Cl | CH₃ | H |
| C.I-240 | A-6 | Cl | H | Cl | CH₃ | H |
| C.I-241 | A-7 | Cl | H | Cl | CH₃ | H |
| C.I-242 | A-8 | Cl | H | Cl | CH₃ | H |
| C.I-243 | A-9 | Cl | H | Cl | CH₃ | H |
| C.I-244 | A-1 | Cl | Cl | Cl | CH₃ | H |
| C.I-245 | A-2 | Cl | Cl | Cl | CH₃ | H |
| C.I-246 | A-3 | Cl | Cl | Cl | CH₃ | H |
| C.I-247 | A-4 | Cl | Cl | Cl | CH₃ | H |
| C.I-248 | A-5 | Cl | Cl | Cl | CH₃ | H |
| C.I-249 | A-6 | Cl | Cl | Cl | CH₃ | H |
| C.I-250 | A-7 | Cl | Cl | Cl | CH₃ | H |
| C.I-251 | A-8 | Cl | Cl | Cl | CH₃ | H |
| C.I-252 | A-9 | Cl | Cl | Cl | CH₃ | H |
| C.I-253 | A-1 | CF₃ | H | Cl | CH₃ | H |
| C.I-254 | A-2 | CF₃ | H | Cl | CH₃ | H |
| C.I-255 | A-3 | CF₃ | H | Cl | CH₃ | H |
| C.I-256 | A-4 | CF₃ | H | Cl | CH₃ | H |
| C.I-257 | A-5 | CF₃ | H | Cl | CH₃ | H |
| C.I-258 | A-6 | CF₃ | H | Cl | CH₃ | H |
| C.I-259 | A-7 | CF₃ | H | Cl | CH₃ | H |
| C.I-260 | A-8 | CF₃ | H | Cl | CH₃ | H |
| C.I-261 | A-9 | CF₃ | H | Cl | CH₃ | H |
| C.I-262 | A-1 | CF₃ | Cl | Cl | CH₃ | H |
| C.I-263 | A-2 | CF₃ | Cl | Cl | CH₃ | H |
| C.I-264 | A-3 | CF₃ | Cl | Cl | CH₃ | H |
| C.I-265 | A-4 | CF₃ | Cl | Cl | CH₃ | H |
| C.I-266 | A-5 | CF₃ | Cl | Cl | CH₃ | H |
| C.I-267 | A-6 | CF₃ | Cl | Cl | CH₃ | H |
| C.I-268 | A-7 | CF₃ | Cl | Cl | CH₃ | H |
| C.I-269 | A-8 | CF₃ | Cl | Cl | CH₃ | H |
| C.I-270 | A-9 | CF₃ | Cl | Cl | CH₃ | H |
| C.I-271 | A-1 | H | H | CF₃ | CH₃ | H |
| C.I-272 | A-2 | H | H | CF₃ | CH₃ | H |
| C.I-273 | A-3 | H | H | CF₃ | CH₃ | H |
| C.I-274 | A-4 | H | H | CF₃ | CH₃ | H |
| C.I-275 | A-5 | H | H | CF₃ | CH₃ | H |
| C.I-276 | A-6 | H | H | CF₃ | CH₃ | H |
| C.I-277 | A-7 | H | H | CF₃ | CH₃ | H |
| C.I-278 | A-8 | H | H | CF₃ | CH₃ | H |
| C.I-279 | A-9 | H | H | CF₃ | CH₃ | H |
| C.I-280 | A-1 | H | Cl | CF₃ | CH₃ | H |
| C.I-281 | A-2 | H | Cl | CF₃ | CH₃ | H |
| C.I-282 | A-3 | H | Cl | CF₃ | CH₃ | H |
| C.I-283 | A-4 | H | Cl | CF₃ | CH₃ | H |
| C.I-284 | A-5 | H | Cl | CF₃ | CH₃ | H |
| C.I-285 | A-6 | H | Cl | CF₃ | CH₃ | H |
| C.I-286 | A-7 | H | Cl | CF₃ | CH₃ | H |
| C.I-287 | A-8 | H | Cl | CF₃ | CH₃ | H |
| C.I-288 | A-9 | H | Cl | CF₃ | CH₃ | H |
| C.I-289 | A-1 | Cl | H | CF₃ | CH₃ | H |
| C.I-290 | A-2 | Cl | H | CF₃ | CH₃ | H |
| C.I-291 | A-3 | Cl | H | CF₃ | CH₃ | H |
| C.I-292 | A-4 | Cl | H | CF₃ | CH₃ | H |
| C.I-293 | A-5 | Cl | H | CF₃ | CH₃ | H |
| C.I-294 | A-6 | Cl | H | CF₃ | CH₃ | H |
| C.I-295 | A-7 | Cl | H | CF₃ | CH₃ | H |
| C.I-296 | A-8 | Cl | H | CF₃ | CH₃ | H |
| C.I-297 | A-9 | Cl | H | CF₃ | CH₃ | H |
| C.I-298 | A-1 | Cl | Cl | CF₃ | CH₃ | H |
| C.I-299 | A-2 | Cl | Cl | CF₃ | CH₃ | H |
| C.I-300 | A-3 | Cl | Cl | CF₃ | CH₃ | H |
| C.I-301 | A-4 | Cl | Cl | CF₃ | CH₃ | H |
| C.I-302 | A-5 | Cl | Cl | CF₃ | CH₃ | H |
| C.I-303 | A-6 | Cl | Cl | CF₃ | CH₃ | H |

TABLE C.I.1-continued

| Compound I | A | R¹ | R² | R³ | R⁴ | R⁵ |
|---|---|---|---|---|---|---|
| C.I-304 | A-7 | Cl | Cl | $CF_3$ | $CH_3$ | H |
| C.I-305 | A-8 | Cl | Cl | $CF_3$ | $CH_3$ | H |
| C.I-306 | A-9 | Cl | Cl | $CF_3$ | $CH_3$ | H |
| C.I-307 | A-1 | $CF_3$ | H | $CF_3$ | $CH_3$ | H |
| C.I-308 | A-2 | $CF_3$ | H | $CF_3$ | $CH_3$ | H |
| C.I-309 | A-3 | $CF_3$ | H | $CF_3$ | $CH_3$ | H |
| C.I-310 | A-4 | $CF_3$ | H | $CF_3$ | $CH_3$ | H |
| C.I-311 | A-5 | $CF_3$ | H | $CF_3$ | $CH_3$ | H |
| C.I-312 | A-6 | $CF_3$ | H | $CF_3$ | $CH_3$ | H |
| C.I-313 | A-7 | $CF_3$ | H | $CF_3$ | $CH_3$ | H |
| C.I-314 | A-8 | $CF_3$ | H | $CF_3$ | $CH_3$ | H |
| C.I-315 | A-9 | $CF_3$ | H | $CF_3$ | $CH_3$ | H |
| C.I-316 | A-1 | $CF_3$ | Cl | $CF_3$ | $CH_3$ | H |
| C.I-317 | A-2 | $CF_3$ | Cl | $CF_3$ | $CH_3$ | H |
| C.I-318 | A-3 | $CF_3$ | Cl | $CF_3$ | $CH_3$ | H |
| C.I-319 | A-4 | $CF_3$ | Cl | $CF_3$ | $CH_3$ | H |
| C.I-320 | A-5 | $CF_3$ | Cl | $CF_3$ | $CH_3$ | H |
| C.I-321 | A-6 | $CF_3$ | Cl | $CF_3$ | $CH_3$ | H |
| C.I-322 | A-7 | $CF_3$ | Cl | $CF_3$ | $CH_3$ | H |
| C.I-323 | A-8 | $CF_3$ | Cl | $CF_3$ | $CH_3$ | H |
| C.I-324 | A-9 | $CF_3$ | Cl | $CF_3$ | $CH_3$ | H |
| C.I-325 | A-1 | H | H | H | CH=CH—CH=CH | |
| C.I-326 | A-2 | H | H | H | CH=CH—CH=CH | |
| C.I-327 | A-3 | H | H | H | CH=CH—CH=CH | |
| C.I-328 | A-4 | H | H | H | CH=CH—CH=CH | |
| C.I-329 | A-5 | H | H | H | CH=CH—CH=CH | |
| C.I-330 | A-6 | H | H | H | CH=CH—CH=CH | |
| C.I-331 | A-7 | H | H | H | CH=CH—CH=CH | |
| C.I-332 | A-8 | H | H | H | CH=CH—CH=CH | |
| C.I-333 | A-9 | H | H | H | CH=CH—CH=CH | |
| C.I-334 | A-1 | H | Cl | H | CH=CH—CH=CH | |
| C.I-335 | A-2 | H | Cl | H | CH=CH—CH=CH | |
| C.I-336 | A-3 | H | Cl | H | CH=CH—CH=CH | |
| C.I-337 | A-4 | H | Cl | H | CH=CH—CH=CH | |
| C.I-338 | A-5 | H | Cl | H | CH=CH—CH=CH | |
| C.I-339 | A-6 | H | Cl | H | CH=CH—CH=CH | |
| C.I-340 | A-7 | H | Cl | H | CH=CH—CH=CH | |
| C.I-341 | A-8 | H | Cl | H | CH=CH—CH=CH | |
| C.I-342 | A-9 | H | Cl | H | CH=CH—CH=CH | |
| C.I-343 | A-1 | Cl | H | H | CH=CH—CH=CH | |
| C.I-344 | A-2 | Cl | H | H | CH=CH—CH=CH | |
| C.I-345 | A-3 | Cl | H | H | CH=CH—CH=CH | |
| C.I-346 | A-4 | Cl | H | H | CH=CH—CH=CH | |
| C.I-347 | A-5 | Cl | H | H | CH=CH—CH=CH | |
| C.I-348 | A-6 | Cl | H | H | CH=CH—CH=CH | |
| C.I-349 | A-7 | Cl | H | H | CH=CH—CH=CH | |
| C.I-350 | A-8 | Cl | H | H | CH=CH—CH=CH | |
| C.I-351 | A-9 | Cl | H | H | CH=CH—CH=CH | |
| C.I-352 | A-1 | Cl | Cl | H | CH=CH—CH=CH | |
| C.I-353 | A-2 | Cl | Cl | H | CH=CH—CH=CH | |
| C.I-354 | A-3 | Cl | Cl | H | CH=CH—CH=CH | |
| C.I-355 | A-4 | Cl | Cl | H | CH=CH—CH=CH | |
| C.I-356 | A-5 | Cl | Cl | H | CH=CH—CH=CH | |
| C.I-357 | A-6 | Cl | Cl | H | CH=CH—CH=CH | |
| C.I-358 | A-7 | Cl | Cl | H | CH=CH—CH=CH | |
| C.I-359 | A-8 | Cl | Cl | H | CH=CH—CH=CH | |
| C.I-360 | A-9 | Cl | Cl | H | CH=CH—CH=CH | |
| C.I-361 | A-1 | $CF_3$ | H | H | CH=CH—CH=CH | |
| C.I-362 | A-2 | $CF_3$ | H | H | CH=CH—CH=CH | |
| C.I-363 | A-3 | $CF_3$ | H | H | CH=CH—CH=CH | |
| C.I-364 | A-4 | $CF_3$ | H | H | CH=CH—CH=CH | |
| C.I-365 | A-5 | $CF_3$ | H | H | CH=CH—CH=CH | |
| C.I-366 | A-6 | $CF_3$ | H | H | CH=CH—CH=CH | |
| C.I-367 | A-7 | $CF_3$ | H | H | CH=CH—CH=CH | |
| C.I-368 | A-8 | $CF_3$ | H | H | CH=CH—CH=CH | |
| C.I-369 | A-9 | $CF_3$ | H | H | CH=CH—CH=CH | |
| C.I-370 | A-1 | $CF_3$ | Cl | H | CH=CH—CH=CH | |
| C.I-371 | A-2 | $CF_3$ | Cl | H | CH=CH—CH=CH | |
| C.I-372 | A-3 | $CF_3$ | Cl | H | CH=CH—CH=CH | |
| C.I-373 | A-4 | $CF_3$ | Cl | H | CH=CH—CH=CH | |
| C.I-374 | A-5 | $CF_3$ | Cl | H | CH=CH—CH=CH | |
| C.I-375 | A-6 | $CF_3$ | Cl | H | CH=CH—CH=CH | |
| C.I-376 | A-7 | $CF_3$ | Cl | H | CH=CH—CH=CH | |
| C.I-377 | A-8 | $CF_3$ | Cl | H | CH=CH—CH=CH | |
| C.I-378 | A-9 | $CF_3$ | Cl | H | CH=CH—CH=CH | |
| C.I-379 | A-1 | H | H | Cl | CH=CH—CH=CH | |
| C.I-380 | A-2 | H | H | Cl | CH=CH—CH=CH | |
| C.I-381 | A-3 | H | H | Cl | CH=CH—CH=CH | |
| C.I-382 | A-4 | H | H | Cl | CH=CH—CH=CH | |
| C.I-383 | A-5 | H | H | Cl | CH=CH—CH=CH | |
| C.I-384 | A-6 | H | H | Cl | CH=CH—CH=CH | |
| C.I-385 | A-7 | H | H | Cl | CH=CH—CH=CH | |
| C.I-386 | A-8 | H | H | Cl | CH=CH—CH=CH | |
| C.I-387 | A-9 | H | H | Cl | CH=CH—CH=CH | |
| C.I-388 | A-1 | H | Cl | Cl | CH=CH—CH=CH | |
| C.I-389 | A-2 | H | Cl | Cl | CH=CH—CH=CH | |
| C.I-390 | A-3 | H | Cl | Cl | CH=CH—CH=CH | |
| C.I-391 | A-4 | H | Cl | Cl | CH=CH—CH=CH | |
| C.I-392 | A-5 | H | Cl | Cl | CH=CH—CH=CH | |
| C.I-393 | A-6 | H | Cl | Cl | CH=CH—CH=CH | |
| C.I-394 | A-7 | H | Cl | Cl | CH=CH—CH=CH | |
| C.I-395 | A-8 | H | Cl | Cl | CH=CH—CH=CH | |
| C.I-396 | A-9 | H | Cl | Cl | CH=CH—CH=CH | |
| C.I-397 | A-1 | Cl | H | Cl | CH=CH—CH=CH | |
| C.I-398 | A-2 | Cl | H | Cl | CH=CH—CH=CH | |
| C.I-399 | A-3 | Cl | H | Cl | CH=CH—CH=CH | |
| C.I-400 | A-4 | Cl | H | Cl | CH=CH—CH=CH | |
| C.I-401 | A-5 | Cl | H | Cl | CH=CH—CH=CH | |
| C.I-402 | A-6 | Cl | H | Cl | CH=CH—CH=CH | |
| C.I-403 | A-7 | Cl | H | Cl | CH=CH—CH=CH | |
| C.I-404 | A-8 | Cl | H | Cl | CH=CH—CH=CH | |
| C.I-405 | A-9 | Cl | H | Cl | CH=CH—CH=CH | |
| C.I-406 | A-1 | Cl | Cl | Cl | CH=CH—CH=CH | |
| C.I-407 | A-2 | Cl | Cl | Cl | CH=CH—CH=CH | |
| C.I-408 | A-3 | Cl | Cl | Cl | CH=CH—CH=CH | |
| C.I-409 | A-4 | Cl | Cl | Cl | CH=CH—CH=CH | |
| C.I-410 | A-5 | Cl | Cl | Cl | CH=CH—CH=CH | |
| C.I-411 | A-6 | Cl | Cl | Cl | CH=CH—CH=CH | |
| C.I-412 | A-7 | Cl | Cl | Cl | CH=CH—CH=CH | |
| C.I-413 | A-8 | Cl | Cl | Cl | CH=CH—CH=CH | |
| C.I-414 | A-9 | Cl | Cl | Cl | CH=CH—CH=CH | |
| C.I-415 | A-1 | $CF_3$ | H | Cl | CH=CH—CH=CH | |
| C.I-416 | A-2 | $CF_3$ | H | Cl | CH=CH—CH=CH | |
| C.I-417 | A-3 | $CF_3$ | H | Cl | CH=CH—CH=CH | |
| C.I-418 | A-4 | $CF_3$ | H | Cl | CH=CH—CH=CH | |
| C.I-419 | A-5 | $CF_3$ | H | Cl | CH=CH—CH=CH | |
| C.I-420 | A-6 | $CF_3$ | H | Cl | CH=CH—CH=CH | |
| C.I-421 | A-7 | $CF_3$ | H | Cl | CH=CH—CH=CH | |
| C.I-422 | A-8 | $CF_3$ | H | Cl | CH=CH—CH=CH | |
| C.I-423 | A-9 | $CF_3$ | H | Cl | CH=CH—CH=CH | |
| C.I-424 | A-1 | $CF_3$ | Cl | Cl | CH=CH—CH=CH | |
| C.I-425 | A-2 | $CF_3$ | Cl | Cl | CH=CH—CH=CH | |
| C.I-426 | A-3 | $CF_3$ | Cl | Cl | CH=CH—CH=CH | |
| C.I-427 | A-4 | $CF_3$ | Cl | Cl | CH=CH—CH=CH | |
| C.I-428 | A-5 | $CF_3$ | Cl | Cl | CH=CH—CH=CH | |
| C.I-429 | A-6 | $CF_3$ | Cl | Cl | CH=CH—CH=CH | |
| C.I-430 | A-7 | $CF_3$ | Cl | Cl | CH=CH—CH=CH | |
| C.I-431 | A-8 | $CF_3$ | Cl | Cl | CH=CH—CH=CH | |
| C.I-432 | A-9 | $CF_3$ | Cl | Cl | CH=CH—CH=CH | |
| C.I-433 | A-1 | H | H | $CF_3$ | CH=CH—CH=CH | |
| C.I-434 | A-2 | H | H | $CF_3$ | CH=CH—CH=CH | |
| C.I-435 | A-3 | H | H | $CF_3$ | CH=CH—CH=CH | |
| C.I-436 | A-4 | H | H | $CF_3$ | CH=CH—CH=CH | |
| C.I-437 | A-5 | H | H | $CF_3$ | CH=CH—CH=CH | |
| C.I-438 | A-6 | H | H | $CF_3$ | CH=CH—CH=CH | |
| C.I-439 | A-7 | H | H | $CF_3$ | CH=CH—CH=CH | |
| C.I-440 | A-8 | H | H | $CF_3$ | CH=CH—CH=CH | |
| C.I-441 | A-9 | H | H | $CF_3$ | CH=CH—CH=CH | |
| C.I-442 | A-1 | H | Cl | $CF_3$ | CH=CH—CH=CH | |
| C.I-443 | A-2 | H | Cl | $CF_3$ | CH=CH—CH=CH | |
| C.I-444 | A-3 | H | Cl | $CF_3$ | CH=CH—CH=CH | |
| C.I-445 | A-4 | H | Cl | $CF_3$ | CH=CH—CH=CH | |
| C.I-446 | A-5 | H | Cl | $CF_3$ | CH=CH—CH=CH | |
| C.I-447 | A-6 | H | Cl | $CF_3$ | CH=CH—CH=CH | |
| C.I-448 | A-7 | H | Cl | $CF_3$ | CH=CH—CH=CH | |
| C.I-449 | A-8 | H | Cl | $CF_3$ | CH=CH—CH=CH | |
| C.I-450 | A-9 | H | Cl | $CF_3$ | CH=CH—CH=CH | |
| C.I-451 | A-1 | Cl | H | $CF_3$ | CH=CH—CH=CH | |
| C.I-452 | A-2 | Cl | H | $CF_3$ | CH=CH—CH=CH | |
| C.I-453 | A-3 | Cl | H | $CF_3$ | CH=CH—CH=CH | |
| C.I-454 | A-4 | Cl | H | $CF_3$ | CH=CH—CH=CH | |
| C.I-455 | A-5 | Cl | H | $CF_3$ | CH=CH—CH=CH | |
| C.I-456 | A-6 | Cl | H | $CF_3$ | CH=CH—CH=CH | |
| C.I-457 | A-7 | Cl | H | $CF_3$ | CH=CH—CH=CH | |
| C.I-458 | A-8 | Cl | H | $CF_3$ | CH=CH—CH=CH | |
| C.I-459 | A-9 | Cl | H | $CF_3$ | CH=CH—CH=CH | |

TABLE C.I.1-continued

| Compound I | A | R¹ | R² | R³ | R⁴ | R⁵ |
|---|---|---|---|---|---|---|
| C.I-460 | A-1 | Cl | Cl | CF₃ | CH=CH | CH=CH |
| C.I-461 | A-2 | Cl | Cl | CF₃ | CH=CH | CH=CH |
| C.I-462 | A-3 | Cl | Cl | CF₃ | CH=CH | CH=CH |
| C.I-463 | A-4 | Cl | Cl | CF₃ | CH=CH | CH=CH |
| C.I-464 | A-5 | Cl | Cl | CF₃ | CH=CH | CH=CH |
| C.I-465 | A-6 | Cl | Cl | CF₃ | CH=CH | CH=CH |
| C.I-466 | A-7 | Cl | Cl | CF₃ | CH=CH | CH=CH |
| C.I-467 | A-8 | Cl | Cl | CF₃ | CH=CH | CH=CH |
| C.I-468 | A-9 | Cl | Cl | CF₃ | CH=CH | CH=CH |
| C.I-469 | A-1 | CF₃ | H | CF₃ | CH=CH | CH=CH |
| C.I-470 | A-2 | CF₃ | H | CF₃ | CH=CH | CH=CH |
| C.I-471 | A-3 | CF₃ | H | CF₃ | CH=CH | CH=CH |
| C.I-472 | A-4 | CF₃ | H | CF₃ | CH=CH | CH=CH |
| C.I-473 | A-5 | CF₃ | H | CF₃ | CH=CH | CH=CH |
| C.I-474 | A-6 | CF₃ | H | CF₃ | CH=CH | CH=CH |
| C.I-475 | A-7 | CF₃ | H | CF₃ | CH=CH | CH=CH |
| C.I-476 | A-8 | CF₃ | H | CF₃ | CH=CH | CH=CH |
| C.I-477 | A-9 | CF₃ | H | CF₃ | CH=CH | CH=CH |
| C.I-478 | A-1 | CF₃ | Cl | CF₃ | CH=CH | CH=CH |
| C.I-479 | A-2 | CF₃ | Cl | CF₃ | CH=CH | CH=CH |
| C.I-480 | A-3 | CF₃ | Cl | CF₃ | CH=CH | CH=CH |
| C.I-481 | A-4 | CF₃ | Cl | CF₃ | CH=CH | CH=CH |
| C.I-482 | A-5 | CF₃ | Cl | CF₃ | CH=CH | CH=CH |
| C.I-483 | A-6 | CF₃ | Cl | CF₃ | CH=CH | CH=CH |
| C.I-484 | A-7 | CF₃ | Cl | CF₃ | CH=CH | CH=CH |
| C.I-485 | A-8 | CF₃ | Cl | CF₃ | CH=CH | CH=CH |
| C.I-486 | A-9 | CF₃ | Cl | CF₃ | CH=CH | CH=CH |

The examples of compounds I of formula I of table C.I.1 include their tautomers, racemic mixtures, individual pure enantiomers and diastereomers and their optically active mixtures.

General preparation methods of compounds of formula I

The active compounds I can be prepared according to methods as described in WO2005/085216, WO2007/074789 or in WO2007/079162.

Preference is given to mixtures of a compound I of the formula I in table C.I with at least one active compound selected from the group II.A of the azoles.

Preference is also given to mixtures of a compound I of the formula I in table C.I with at least one active compound selected from the group II.B of the strobilurins.

Preference is given to mixtures of a compound I of the formula I in table C.I with at least one active compound selected from the group II.C of the carboxamides.

Preference is furthermore also given to mixtures of a compound I of the formula I in table C.I with at least one active compound selected from the group II.D of the heterocyclic compounds.

Preference is furthermore also given to mixtures of a compound I of the formula I in table C.I with at least one active compound selected from the group II.E of the carbamates.

Preference is furthermore also given to mixtures of a compound I of the formula I in table C.I with at least one active compound selected from the group II.F of other various fungicides.

Preferences of Fungicidal Compound II

Preference is given to mixtures of a compound of the formula I with at least one active compound II selected from the group II.A of azoles consisting of cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, cyazofamid, benomyl, carbendazim and ethaboxam.

Particular preference is given to mixtures of a compound of the formula I with at least one active compound II selected from the group II.A of azoles consisting of cyproconazole, difenoconazole, epoxiconazole, fluquinconazole, flusilazole, flutriafol, metconazole, myclobutanil, propiconazole, prothioconazole, triadimefon, triadimenol, tebuconazole, tetraconazole, triticonazole, prochloraz, cyazofamid, benomyl and carbendazim.

Very particular preference is given to mixtures of a compound of the formula I with at least one active compound II selected from the group II.A of azoles consisting of benomyl, carbendazim, epoxiconazole, fluquinconazole, flutriafol, flusilazole, metconazole, prochloraz, prothioconazole, tebuconazole and triticonazole.

Preference is given to mixtures of a compound of the formula I with at least one active compound II selected from the group of the II.B of strobilurins consisting of azoxystrobin, dimoxystrobin, fluoxastrobin, kresoxim-methyl, orysastrobin, picoxystrobin, pyraclostrobin and trifloxystrobin.

Particular preference is given to mixtures of a compound of the formula I with at least one active compound II selected from the group II.B of strobilurins consisting of azoxystrobin, kresoxim-methyl, orysastrobin, picoxystrobin, pyraclostrobin and trifloxystrobin.

Very particular preference is given to mixtures of a compound of the formula I with picoxystrobin, pyraclostrobin and trifloxystrobin.

Preference is given to mixtures of a compound of the formula I with at least one active compound II selected from the group II.C of carboxamides consisting of bixafen, boscalid, carpropamid, dimethomorph, fenhexamid, flumorph, fluopicolide (picobenzamid), fluopyram, isothianil, mandipropamid, metalaxyl, mefenoxam, ofurace, penthiopyrad and zoxamide.

Particular preference is given to mixtures of a compound of the formula I with at least one active compound II selected from the group II.C of carboxamides consisting of boscalid, carpropamid, dimethomorph, fenhexamid, fluopicolide, fluopyram, mandipropamid, metalaxyl, mefenoxam, ofurace, penthiopyrad and zoxamide.

Very particular preference is given to mixtures of a compound of the formula I with at least one active compound II selected from the group II.C of carboxamides consisting of boscalid, dimethomorph, fenhexamid and penthiopyrad.

Preference is given to mixtures of a compound of the formula I with at least one active compound II selected from the group II.D of heterocyclic compounds consisting of acibenzolar-S-methyl, captafol, cyprodinil, dodemorph, famoxadone fenamidone, fenarimol, fenpropimorph, fenpropidin, fenoxanil, fludioxonil, fluazinam, folpet, iprodione, mepanipyrim, probenazole, proquinazid, pyrimethanil, quinoxyfen triforine, tridemorph, vinclozolin and 5-chloro-7-(4-methylpiperidin-1-yl)-6-(2,4,6-trifluorophenyl)-[1,2,4]triazolo[1,5-a]pyrimidine.

Particular preference is also given to mixtures of a compound of the formula I with at least one active compound II selected from the group II.D of heterocyclic compounds consisting of dodemorph, famoxadone, fenpropimorph, iprodione, proquinazid, pyrimethanil, quinoxyfen, tridemorph, vinclozolin and 5-chloro-7-(4-methylpiperidin-1-yl)-6-(2,4,6-trifluorophenyl)-[1,2,4]triazolo[1,5-a]pyrimidine.

Very particular preference is given to mixtures of a compound of the formula I with at least one active compound II selected from the group II.D of heterocyclic compounds consisting of dodemorph, famoxadone, fenpropimorph, iprodione, proquinazid pyrimethanil, tridemorph and 5-chloro-7-(4-methylpiperidin-1-yl)-6-(2,4,6-trifluorophenyl)-[1,2,4]triazolo[1,5-a]pyrimidine.

Preference is also given to mixtures of a compound of the formula I with at least one active compound II selected from the group II.E of carbamates consisting of iprovalicarb, flubenthiavalicarb, maneb, mancozeb, metiram, propineb, propamocarb and thiram.

Particular preference is also given to mixtures of a compound of the formula I with at least one active compound II selected from the group II.E of carbamates consisting of iprovalicarb, flubenthiavalicarb, maneb, mancozeb, metiram and thiram.

Very particular preference is given to mixtures of a compound of the formula I with at least one active compound II selected from the group II.E of carbamates consisting of maneb, mancozeb, metiram and thiram.

Preference is also given to mixtures of a compound of the formula I with at least one active compound II selected from the group II.F of other fungicides consisting of chlorothalonil, copper acetate, copper hydroxide, copper oxychloride, basic copper sulfate, cymoxanil, dichlofluanid, dithianon, fentin salts, such as fentin acetate, fosetyl, fosetyl-aluminum, flusulfamide, metrafenone, phosphorous acid and its salts, thiophanate-methyl, sulfur and spiroxamine.

Particular preference is also given to mixtures of a compound of the formula I with at least one active compound II selected from the group II.F of other fungicides consisting of chlorothalonil, dithianon, flusulfamide, fosetyl-aluminium, metrafenone, phosphorous acid and its salts and thiophanate-methyl.

Very particular preference is given to mixtures of a compound of the formula I with at least one active compound II selected from the group II.F of other fungicides consisting of chlorothalonil, dithianon, flusulfamide, metrafenone and phosphorous acid and its salts.

Preferred combinations of insecticidal compound I with fungicidal compound II

High Preference is given to the following combinations of insecticidal compounds I with fungicidal compounds II in tables A to F.

TABLE A

Preferred combinations of preferred insecticidal compound I with preferred fungicidal compound II of group II.A:

| Mixture no. | Active compound I | Active compound II |
| --- | --- | --- |
| M-A.1 | C.I-37 | benomyl |
| M-A.2 | C.I-40 | benomyl |
| M-A.3 | C.I-73 | benomyl |
| M-A.4 | C.I-76 | benomyl |
| M-A.5 | C.I-145 | benomyl |
| M-A.6 | C.I-148 | benomyl |
| M-A.7 | C.I-199 | benomyl |
| M-A.8 | C.I-202 | benomyl |
| M-A.9 | C.I-235 | benomyl |
| M-A.10 | C.I-238 | benomyl |
| M-A.11 | C.I-240 | benomyl |
| M-A.12 | C.I-244 | benomyl |
| M-A.13 | C.I-247 | benomyl |
| M-A.14 | C.I-307 | benomyl |
| M-A.15 | C.I-310 | benomyl |
| M-A.16 | C.I-361 | benomyl |
| M-A.17 | C.I-364 | benomyl |
| M-A.18 | C.I-397 | benomyl |
| M-A.19 | C.I-400 | benomyl |
| M-A.20 | C.I-402 | benomyl |
| M-A.21 | C.I-406 | benomyl |
| M-A.22 | C.I-409 | benomyl |
| M-A.23 | C.I-469 | benomyl |
| M-A.24 | C.I-472 | benomyl |
| M-A.25 | C.I-37 | carbendazim |
| M-A.26 | C.I-40 | carbendazim |
| M-A.27 | C.I-73 | carbendazim |
| M-A.28 | C.I-76 | carbendazim |

TABLE A-continued

Preferred combinations of preferred insecticidal compound I with preferred fungicidal compound II of group II.A:

| Mixture no. | Active compound I | Active compound II |
| --- | --- | --- |
| M-A.29 | C.I-145 | carbendazim |
| M-A.30 | C.I-148 | carbendazim |
| M-A.31 | C.I-199 | carbendazim |
| M-A.32 | C.I-202 | carbendazim |
| M-A.33 | C.I-235 | carbendazim |
| M-A.34 | C.I-238 | carbendazim |
| M-A.35 | C.I-240 | carbendazim |
| M-A.36 | C.I-244 | carbendazim |
| M-A.37 | C.I-247 | carbendazim |
| M-A.38 | C.I-307 | carbendazim |
| M-A.39 | C.I-310 | carbendazim |
| M-A.40 | C.I-361 | carbendazim |
| M-A.41 | C.I-364 | carbendazim |
| M-A.42 | C.I-397 | carbendazim |
| M-A.43 | C.I-400 | carbendazim |
| M-A.44 | C.I-402 | carbendazim |
| M-A.45 | C.I-406 | carbendazim |
| M-A.46 | C.I-409 | carbendazim |
| M-A.47 | C.I-469 | carbendazim |
| M-A.48 | C.I-472 | carbendazim |
| M-A.49 | C.I-37 | epoxiconazole |
| M-A.50 | C.I-40 | epoxiconazole |
| M-A.51 | C.I-73 | epoxiconazole |
| M-A.52 | C.I-76 | epoxiconazole |
| M-A.53 | C.I-145 | epoxiconazole |
| M-A.54 | C.I-148 | epoxiconazole |
| M-A.55 | C.I-199 | epoxiconazole |
| M-A.56 | C.I-202 | epoxiconazole |
| M-A.57 | C.I-235 | epoxiconazole |
| M-A.58 | C.I-238 | epoxiconazole |
| M-A.59 | C.I-240 | epoxiconazole |
| M-A.60 | C.I-244 | epoxiconazole |
| M-A.61 | C.I-247 | epoxiconazole |
| M-A.62 | C.I-307 | epoxiconazole |
| M-A.63 | C.I-310 | epoxiconazole |
| M-A.64 | C.I-361 | epoxiconazole |
| M-A.65 | C.I-364 | epoxiconazole |
| M-A.66 | C.I-397 | epoxiconazole |
| M-A.67 | C.I-400 | epoxiconazole |
| M-A.68 | C.I-402 | epoxiconazole |
| M-A.69 | C.I-406 | epoxiconazole |
| M-A.70 | C.I-409 | epoxiconazole |
| M-A.71 | C.I-469 | epoxiconazole |
| M-A.72 | C.I-472 | epoxiconazole |
| M-A.73 | C.I-37 | fluquinconazole |
| M-A.74 | C.I-40 | fluquinconazole |
| M-A.75 | C.I-73 | fluquinconazole |
| M-A.76 | C.I-76 | fluquinconazole |
| M-A.77 | C.I-145 | fluquinconazole |
| M-A.78 | C.I-148 | fluquinconazole |
| M-A.79 | C.I-199 | fluquinconazole |
| M-A.80 | C.I-202 | fluquinconazole |
| M-A.81 | C.I-235 | fluquinconazole |
| M-A.82 | C.I-238 | fluquinconazole |
| M-A.83 | C.I-240 | fluquinconazole |
| M-A.84 | C.I-244 | fluquinconazole |
| M-A.85 | C.I-247 | fluquinconazole |
| M-A.86 | C.I-307 | fluquinconazole |
| M-A.87 | C.I-310 | fluquinconazole |
| M-A.88 | C.I-361 | fluquinconazole |
| M-A.89 | C.I-364 | fluquinconazole |
| M-A.90 | C.I-397 | fluquinconazole |
| M-A.91 | C.I-400 | fluquinconazole |
| M-A.92 | C.I-402 | fluquinconazole |
| M-A.93 | C.I-406 | fluquinconazole |
| M-A.94 | C.I-409 | fluquinconazole |
| M-A.95 | C.I-469 | fluquinconazole |
| M-A.96 | C.I-472 | fluquinconazole |
| M-A.97 | C.I-37 | flusilazole |
| M-A.98 | C.I-40 | flusilazole |
| M-A.99 | C.I-73 | flusilazole |
| M-A.100 | C.I-76 | flusilazole |
| M-A.101 | C.I-145 | flusilazole |
| M-A.102 | C.I-148 | flusilazole |

TABLE A-continued

Preferred combinations of preferred insecticidal compound I with preferred fungicidal compound II of group II.A:

| Mixture no. | Active compound I | Active compound II |
|---|---|---|
| M-A.103 | C.I-199 | flusilazole |
| M-A.104 | C.I-202 | flusilazole |
| M-A.105 | C.I-235 | flusilazole |
| M-A.106 | C.I-238 | flusilazole |
| M-A.107 | C.I-240 | flusilazole |
| M-A.108 | C.I-244 | flusilazole |
| M-A.109 | C.I-247 | flusilazole |
| M-A.110 | C.I-307 | flusilazole |
| M-A.111 | C.I-310 | flusilazole |
| M-A.112 | C.I-361 | flusilazole |
| M-A.113 | C.I-364 | flusilazole |
| M-A.114 | C.I-397 | flusilazole |
| M-A.115 | C.I-400 | flusilazole |
| M-A.116 | C.I-402 | flusilazole |
| M-A.117 | C.I-406 | flusilazole |
| M-A.118 | C.I-409 | flusilazole |
| M-A.119 | C.I-469 | flusilazole |
| M-A.120 | C.I-472 | flusilazole |
| M-A.121 | C.I-37 | flutriafol |
| M-A.122 | C.I-40 | flutriafol |
| M-A.123 | C.I-73 | flutriafol |
| M-A.124 | C.I-76 | flutriafol |
| M-A.125 | C.I-145 | flutriafol |
| M-A.126 | C.I-148 | flutriafol |
| M-A.127 | C.I-199 | flutriafol |
| M-A.128 | C.I-202 | flutriafol |
| M-A.129 | C.I-235 | flutriafol |
| M-A.130 | C.I-238 | flutriafol |
| M-A.131 | C.I-240 | flutriafol |
| M-A.132 | C.I-244 | flutriafol |
| M-A.133 | C.I-247 | flutriafol |
| M-A.134 | C.I-307 | flutriafol |
| M-A.135 | C.I-310 | flutriafol |
| M-A.136 | C.I-361 | flutriafol |
| M-A.137 | C.I-364 | flutriafol |
| M-A.138 | C.I-397 | flutriafol |
| M-A.139 | C.I-400 | flutriafol |
| M-A.140 | C.I-402 | flutriafol |
| M-A.141 | C.I-406 | flutriafol |
| M-A.142 | C.I-409 | flutriafol |
| M-A.143 | C.I-469 | flutriafol |
| M-A.144 | C.I-472 | flutriafol |
| M-A.145 | C.I-37 | metconazole |
| M-A.146 | C.I-40 | metconazole |
| M-A.147 | C.I-73 | metconazole |
| M-A.148 | C.I-76 | metconazole |
| M-A.149 | C.I-145 | metconazole |
| M-A.150 | C.I-148 | metconazole |
| M-A.151 | C.I-199 | metconazole |
| M-A.152 | C.I-202 | metconazole |
| M-A.153 | C.I-235 | metconazole |
| M-A.154 | C.I-238 | metconazole |
| M-A.155 | C.I-240 | metconazole |
| M-A.156 | C.I-244 | metconazole |
| M-A.157 | C.I-247 | metconazole |
| M-A.158 | C.I-307 | metconazole |
| M-A.159 | C.I-310 | metconazole |
| M-A.160 | C.I-361 | metconazole |
| M-A.161 | C.I-364 | metconazole |
| M-A.162 | C.I-397 | metconazole |
| M-A.163 | C.I-400 | metconazole |
| M-A.164 | C.I-402 | metconazole |
| M-A.165 | C.I-406 | metconazole |
| M-A.166 | C.I-409 | metconazole |
| M-A.167 | C.I-469 | metconazole |
| M-A.168 | C.I-472 | metconazole |
| M-A.169 | C.I-37 | prochloraz |
| M-A.170 | C.I-40 | prochloraz |
| M-A.171 | C.I-73 | prochloraz |
| M-A.172 | C.I-76 | prochloraz |
| M-A.173 | C.I-145 | prochloraz |
| M-A.174 | C.I-148 | prochloraz |
| M-A.175 | C.I-199 | prochloraz |
| M-A.176 | C.I-202 | prochloraz |
| M-A.177 | C.I-235 | prochloraz |
| M-A.178 | C.I-238 | prochloraz |
| M-A.179 | C.I-240 | prochloraz |
| M-A.180 | C.I-244 | prochloraz |
| M-A.181 | C.I-247 | prochloraz |
| M-A.182 | C.I-307 | prochloraz |
| M-A.183 | C.I-310 | prochloraz |
| M-A.184 | C.I-361 | prochloraz |
| M-A.185 | C.I-364 | prochloraz |
| M-A.186 | C.I-397 | prochloraz |
| M-A.187 | C.I-400 | prochloraz |
| M-A.188 | C.I-402 | prochloraz |
| M-A.189 | C.I-406 | prochloraz |
| M-A.190 | C.I-409 | prochloraz |
| M-A.191 | C.I-469 | prochloraz |
| M-A.192 | C.I-472 | prochloraz |
| M-A.193 | C.I-37 | prothioconazole |
| M-A.194 | C.I-40 | prothioconazole |
| M-A.195 | C.I-73 | prothioconazole |
| M-A.196 | C.I-76 | prothioconazole |
| M-A.197 | C.I-145 | prothioconazole |
| M-A.198 | C.I-148 | prothioconazole |
| M-A.199 | C.I-199 | prothioconazole |
| M-A.200 | C.I-202 | prothioconazole |
| M-A.201 | C.I-235 | prothioconazole |
| M-A.202 | C.I-238 | prothioconazole |
| M-A.203 | C.I-240 | prothioconazole |
| M-A.204 | C.I-244 | prothioconazole |
| M-A.205 | C.I-247 | prothioconazole |
| M-A.206 | C.I-307 | prothioconazole |
| M-A.207 | C.I-310 | prothioconazole |
| M-A.208 | C.I-361 | prothioconazole |
| M-A.209 | C.I-364 | prothioconazole |
| M-A.210 | C.I-397 | prothioconazole |
| M-A.211 | C.I-400 | prothioconazole |
| M-A.212 | C.I-402 | prothioconazole |
| M-A.213 | C.I-406 | prothioconazole |
| M-A.214 | C.I-409 | prothioconazole |
| M-A.215 | C.I-469 | prothioconazole |
| M-A.216 | C.I-472 | prothioconazole |
| M-A.217 | C.I-37 | tebuconazole |
| M-A.218 | C.I-40 | tebuconazole |
| M-A.219 | C.I-73 | tebuconazole |
| M-A.220 | C.I-76 | tebuconazole |
| M-A.221 | C.I-145 | tebuconazole |
| M-A.222 | C.I-148 | tebuconazole |
| M-A.223 | C.I-199 | tebuconazole |
| M-A.224 | C.I-202 | tebuconazole |
| M-A.225 | C.I-235 | tebuconazole |
| M-A.226 | C.I-238 | tebuconazole |
| M-A.227 | C.I-240 | tebuconazole |
| M-A.228 | C.I-244 | tebuconazole |
| M-A.229 | C.I-247 | tebuconazole |
| M-A.230 | C.I-307 | tebuconazole |
| M-A.231 | C.I-310 | tebuconazole |
| M-A.232 | C.I-361 | tebuconazole |
| M-A.233 | C.I-364 | tebuconazole |
| M-A.234 | C.I-397 | tebuconazole |
| M-A.235 | C.I-400 | tebuconazole |
| M-A.236 | C.I-402 | tebuconazole |
| M-A.237 | C.I-406 | tebuconazole |
| M-A.238 | C.I-409 | tebuconazole |
| M-A.239 | C.I-469 | tebuconazole |
| M-A.240 | C.I-472 | tebuconazole |
| M-A.241 | C.I-37 | triticonazole |
| M-A.242 | C.I-40 | triticonazole |
| M-A.243 | C.I-73 | triticonazole |
| M-A.244 | C.I-76 | triticonazole |
| M-A.245 | C.I-145 | triticonazole |
| M-A.246 | C.I-148 | triticonazole |
| M-A.247 | C.I-199 | triticonazole |
| M-A.248 | C.I-202 | triticonazole |
| M-A.249 | C.I-235 | triticonazole |
| M-A.250 | C.I-238 | triticonazole |

TABLE A-continued

Preferred combinations of preferred insecticidal compound I with preferred fungicidal compound II of group II.A:

| Mixture no. | Active compound I | Active compound II |
|---|---|---|
| M-A.251 | C.I-240 | triticonazole |
| M-A.252 | C.I-244 | triticonazole |
| M-A.253 | C.I-247 | triticonazole |
| M-A.254 | C.I-307 | triticonazole |
| M-A.255 | C.I-310 | triticonazole |
| M-A.256 | C.I-361 | triticonazole |
| M-A.257 | C.I-364 | triticonazole |
| M-A.258 | C.I-397 | triticonazole |
| M-A.259 | C.I-400 | triticonazole |
| M-A.260 | C.I-402 | triticonazole |
| M-A.261 | C.I-406 | triticonazole |
| M-A.262 | C.I-409 | triticonazole |
| M-A.263 | C.I-469 | triticonazole |
| M-A.264 | C.I-472 | triticonazole |

TABLE B

Preferred combinations of preferred insecticidal compound I with preferred fungicidal compound II of group II.B:

| Mixture no. | Active compound I | Active compound II |
|---|---|---|
| M-B.1 | C.I-37 | pyraclostrobin |
| M-B.2 | C.I-40 | pyraclostrobin |
| M-B.3 | C.I-73 | pyraclostrobin |
| M-B.4 | C.I-76 | pyraclostrobin |
| M-B.5 | C.I-145 | pyraclostrobin |
| M-B.6 | C.I-148 | pyraclostrobin |
| M-B.7 | C.I-199 | pyraclostrobin |
| M-B.8 | C.I-202 | pyraclostrobin |
| M-B.9 | C.I-235 | pyraclostrobin |
| M-B.10 | C.I-238 | pyraclostrobin |
| M-B.11 | C.I-240 | pyraclostrobin |
| M-B.12 | C.I-244 | pyraclostrobin |
| M-B.13 | C.I-247 | pyraclostrobin |
| M-B.14 | C.I-307 | pyraclostrobin |
| M-B.15 | C.I-310 | pyraclostrobin |
| M-B.16 | C.I-361 | pyraclostrobin |
| M-B.17 | C.I-364 | pyraclostrobin |
| M-B.18 | C.I-397 | pyraclostrobin |
| M-B.19 | C.I-400 | pyraclostrobin |
| M-B.20 | C.I-402 | pyraclostrobin |
| M-B.21 | C.I-406 | pyraclostrobin |
| M-B.22 | C.I-409 | pyraclostrobin |
| M-B.23 | C.I-469 | pyraclostrobin |
| M-B.24 | C.I-472 | pyraclostrobin |
| M-B.25 | C.I-37 | picoxystrobin |
| M-B.26 | C.I-40 | picoxystrobin |
| M-B.27 | C.I-73 | picoxystrobin |
| M-B.28 | C.I-76 | picoxystrobin |
| M-B.29 | C.I-145 | picoxystrobin |
| M-B.30 | C.I-148 | picoxystrobin |
| M-B.31 | C.I-199 | picoxystrobin |
| M-B.32 | C.I-202 | picoxystrobin |
| M-B.33 | C.I-235 | picoxystrobin |
| M-B.34 | C.I-238 | picoxystrobin |
| M-B.35 | C.I-240 | picoxystrobin |
| M-B.36 | C.I-244 | picoxystrobin |
| M-B.37 | C.I-247 | picoxystrobin |
| M-B.38 | C.I-307 | picoxystrobin |
| M-B.39 | C.I-310 | picoxystrobin |
| M-B.40 | C.I-361 | picoxystrobin |
| M-B.41 | C.I-364 | picoxystrobin |
| M-B.42 | C.I-397 | picoxystrobin |
| M-B.43 | C.I-400 | picoxystrobin |
| M-B.44 | C.I-402 | picoxystrobin |
| M-B.45 | C.I-406 | picoxystrobin |
| M-B.46 | C.I-409 | picoxystrobin |
| M-B.47 | C.I-469 | picoxystrobin |
| M-B.48 | C.I-472 | picoxystrobin |

TABLE B-continued

Preferred combinations of preferred insecticidal compound I with preferred fungicidal compound II of group II.B:

| Mixture no. | Active compound I | Active compound II |
|---|---|---|
| M-B.49 | C.I-37 | trifloxystrobin |
| M-B.50 | C.I-40 | trifloxystrobin |
| M-B.51 | C.I-73 | trifloxystrobin |
| M-B.52 | C.I-76 | trifloxystrobin |
| M-B.53 | C.I-145 | trifloxystrobin |
| M-B.54 | C.I-148 | trifloxystrobin |
| M-B.55 | C.I-199 | trifloxystrobin |
| M-B.56 | C.I-202 | trifloxystrobin |
| M-B.57 | C.I-235 | trifloxystrobin |
| M-B.58 | C.I-238 | trifloxystrobin |
| M-B.59 | C.I-240 | trifloxystrobin |
| M-B.60 | C.I-244 | trifloxystrobin |
| M-B.61 | C.I-247 | trifloxystrobin |
| M-B.62 | C.I-307 | trifloxystrobin |
| M-B.63 | C.I-310 | trifloxystrobin |
| M-B.64 | C.I-361 | trifloxystrobin |
| M-B.65 | C.I-364 | trifloxystrobin |
| M-B.66 | C.I-397 | trifloxystrobin |
| M-B.67 | C.I-400 | trifloxystrobin |
| M-B.68 | C.I-402 | trifloxystrobin |
| M-B.69 | C.I-406 | trifloxystrobin |
| M-B.70 | C.I-409 | trifloxystrobin |
| M-B.71 | C.I-469 | trifloxystrobin |
| M-B.72 | C.I-472 | trifloxystrobin |

TABLE C

Preferred combinations of preferred insecticidal compound I with preferred fungicidal compound II of group II.C:

| Mixture no. | Active compound I | Active compound II |
|---|---|---|
| M-C.1 | C.I-37 | boscalid |
| M-C.2 | C.I-40 | boscalid |
| M-C.3 | C.I-73 | boscalid |
| M-C.4 | C.I-76 | boscalid |
| M-C.5 | C.I-145 | boscalid |
| M-C.6 | C.I-148 | boscalid |
| M-C.7 | C.I-199 | boscalid |
| M-C.8 | C.I-202 | boscalid |
| M-C.9 | C.I-235 | boscalid |
| M-C.10 | C.I-238 | boscalid |
| M-C.11 | C.I-240 | boscalid |
| M-C.12 | C.I-244 | boscalid |
| M-C.13 | C.I-247 | boscalid |
| M-C.14 | C.I-307 | boscalid |
| M-C.15 | C.I-310 | boscalid |
| M-C.16 | C.I-361 | boscalid |
| M-C.17 | C.I-364 | boscalid |
| M-C.18 | C.I-397 | boscalid |
| M-C.19 | C.I-400 | boscalid |
| M-C.20 | C.I-402 | boscalid |
| M-C.21 | C.I-406 | boscalid |
| M-C.22 | C.I-409 | boscalid |
| M-C.23 | C.I-469 | boscalid |
| M-C.24 | C.I-472 | boscalid |
| M-C.25 | C.I-37 | dimethomorph |
| M-C.26 | C.I-40 | dimethomorph |
| M-C.27 | C.I-73 | dimethomorph |
| M-C.28 | C.I-76 | dimethomorph |
| M-C.29 | C.I-145 | dimethomorph |
| M-C.30 | C.I-148 | dimethomorph |
| M-C.31 | C.I-199 | dimethomorph |
| M-C.32 | C.I-202 | dimethomorph |
| M-C.33 | C.I-235 | dimethomorph |
| M-C.34 | C.I-238 | dimethomorph |
| M-C.35 | C.I-240 | dimethomorph |
| M-C.36 | C.I-244 | dimethomorph |
| M-C.37 | C.I-247 | dimethomorph |
| M-C.38 | C.I-307 | dimethomorph |

TABLE C-continued

Preferred combinations of preferred insecticidal compound I with preferred fungicidal compound II of group II.C:

| Mixture no. | Active compound I | Active compound II |
|---|---|---|
| M-C.39 | C.I-310 | dimethomorph |
| M-C.40 | C.I-361 | dimethomorph |
| M-C.41 | C.I-364 | dimethomorph |
| M-C.42 | C.I-397 | dimethomorph |
| M-C.43 | C.I-400 | dimethomorph |
| M-C.44 | C.I-402 | dimethomorph |
| M-C.45 | C.I-406 | dimethomorph |
| M-C.46 | C.I-409 | dimethomorph |
| M-C.47 | C.I-469 | dimethomorph |
| M-C.48 | C.I-472 | dimethomorph |
| M-C.49 | C.I-37 | penthiopyrad |
| M-C.50 | C.I-40 | penthiopyrad |
| M-C.51 | C.I-73 | penthiopyrad |
| M-C.52 | C.I-76 | penthiopyrad |
| M-C.53 | C.I-145 | penthiopyrad |
| M-C.54 | C.I-148 | penthiopyrad |
| M-C.55 | C.I-199 | penthiopyrad |
| M-C.56 | C.I-202 | penthiopyrad |
| M-C.57 | C.I-235 | penthiopyrad |
| M-C.58 | C.I-238 | penthiopyrad |
| M-C.59 | C.I-240 | penthiopyrad |
| M-C.60 | C.I-244 | penthiopyrad |
| M-C.61 | C.I-247 | penthiopyrad |
| M-C.62 | C.I-307 | penthiopyrad |
| M-C.63 | C.I-310 | penthiopyrad |
| M-C.64 | C.I-361 | penthiopyrad |
| M-C.65 | C.I-364 | penthiopyrad |
| M-C.66 | C.I-397 | penthiopyrad |
| M-C.67 | C.I-400 | penthiopyrad |
| M-C.68 | C.I-402 | penthiopyrad |
| M-C.69 | C.I-406 | penthiopyrad |
| M-C.70 | C.I-409 | penthiopyrad |
| M-C.71 | C.I-469 | penthiopyrad |
| M-C.72 | C.I-472 | penthiopyrad |
| M-C.73 | C.I-37 | fenhexamid |
| M-C.74 | C.I-40 | fenhexamid |
| M-C.75 | C.I-73 | fenhexamid |
| M-C.76 | C.I-76 | fenhexamid |
| M-C.77 | C.I-145 | fenhexamid |
| M-C.78 | C.I-148 | fenhexamid |
| M-C.79 | C.I-199 | fenhexamid |
| M-C.80 | C.I-202 | fenhexamid |
| M-C.81 | C.I-235 | fenhexamid |
| M-C.82 | C.I-238 | fenhexamid |
| M-C.83 | C.I-240 | fenhexamid |
| M-C.84 | C.I-244 | fenhexamid |
| M-C.85 | C.I-247 | fenhexamid |
| M-C.86 | C.I-307 | fenhexamid |
| M-C.87 | C.I-310 | fenhexamid |
| M-C.88 | C.I-361 | fenhexamid |
| M-C.89 | C.I-364 | fenhexamid |
| M-C.90 | C.I-397 | fenhexamid |
| M-C.91 | C.I-400 | fenhexamid |
| M-C.92 | C.I-402 | fenhexamid |
| M-C.93 | C.I-406 | fenhexamid |
| M-C.94 | C.I-409 | fenhexamid |
| M-C.95 | C.I-469 | fenhexamid |
| M-C.96 | C.I-472 | fenhexamid |

TABLE D

Preferred combinations of preferred insecticidal compound I with preferred fungicidal compound II of group II.D:

| Mixture no. | Active compound I | Active compound II |
|---|---|---|
| M-D.1 | C.I-37 | dodemorph |
| M-D.2 | C.I-40 | dodemorph |
| M-D.3 | C.I-73 | dodemorph |
| M-D.4 | C.I-76 | dodemorph |
| M-D.5 | C.I-145 | dodemorph |
| M-D.6 | C.I-148 | dodemorph |
| M-D.7 | C.I-199 | dodemorph |
| M-D.8 | C.I-202 | dodemorph |
| M-D.9 | C.I-235 | dodemorph |
| M-D.10 | C.I-238 | dodemorph |
| M-D.11 | C.I-240 | dodemorph |
| M-D.12 | C.I-244 | dodemorph |
| M-D.13 | C.I-247 | dodemorph |
| M-D.14 | C.I-307 | dodemorph |
| M-D.15 | C.I-310 | dodemorph |
| M-D.16 | C.I-361 | dodemorph |
| M-D.17 | C.I-364 | dodemorph |
| M-D.18 | C.I-397 | dodemorph |
| M-D.19 | C.I-400 | dodemorph |
| M-D.20 | C.I-402 | dodemorph |
| M-D.21 | C.I-406 | dodemorph |
| M-D.22 | C.I-409 | dodemorph |
| M-D.23 | C.I-469 | dodemorph |
| M-D.24 | C.I-472 | dodemorph |
| M-D.25 | C.I-37 | famoxadone |
| M-D.26 | C.I-40 | famoxadone |
| M-D.27 | C.I-73 | famoxadone |
| M-D.28 | C.I-76 | famoxadone |
| M-D.29 | C.I-145 | famoxadone |
| M-D.30 | C.I-148 | famoxadone |
| M-D.31 | C.I-199 | famoxadone |
| M-D.32 | C.I-202 | famoxadone |
| M-D.33 | C.I-235 | famoxadone |
| M-D.34 | C.I-238 | famoxadone |
| M-D.35 | C.I-240 | famoxadone |
| M-D.36 | C.I-244 | famoxadone |
| M-D.37 | C.I-247 | famoxadone |
| M-D.38 | C.I-307 | famoxadone |
| M-D.39 | C.I-310 | famoxadone |
| M-D.40 | C.I-361 | famoxadone |
| M-D.41 | C.I-364 | famoxadone |
| M-D.42 | C.I-397 | famoxadone |
| M-D.43 | C.I-400 | famoxadone |
| M-D.44 | C.I-402 | famoxadone |
| M-D.45 | C.I-406 | famoxadone |
| M-D.46 | C.I-409 | famoxadone |
| M-D.47 | C.I-469 | famoxadone |
| M-D.48 | C.I-472 | famoxadone |
| M-D.49 | C.I-37 | fenpropimorph |
| M-D.50 | C.I-40 | fenpropimorph |
| M-D.51 | C.I-73 | fenpropimorph |
| M-D.52 | C.I-76 | fenpropimorph |
| M-D.53 | C.I-145 | fenpropimorph |
| M-D.54 | C.I-148 | fenpropimorph |
| M-D.55 | C.I-199 | fenpropimorph |
| M-D.56 | C.I-202 | fenpropimorph |
| M-D.57 | C.I-235 | fenpropimorph |
| M-D.58 | C.I-238 | fenpropimorph |
| M-D.59 | C.I-240 | fenpropimorph |
| M-D.60 | C.I-244 | fenpropimorph |
| M-D.61 | C.I-247 | fenpropimorph |
| M-D.62 | C.I-307 | fenpropimorph |
| M-D.63 | C.I-310 | fenpropimorph |
| M-D.64 | C.I-361 | fenpropimorph |
| M-D.65 | C.I-364 | fenpropimorph |
| M-D.66 | C.I-397 | fenpropimorph |
| M-D.67 | C.I-400 | fenpropimorph |
| M-D.68 | C.I-402 | fenpropimorph |
| M-D.69 | C.I-406 | fenpropimorph |
| M-D.70 | C.I-409 | fenpropimorph |
| M-D.71 | C.I-469 | fenpropimorph |
| M-D.72 | C.I-472 | fenpropimorph |
| M-D.73 | C.I-37 | proquinazid |
| M-D.74 | C.I-40 | proquinazid |
| M-D.75 | C.I-73 | proquinazid |
| M-D.76 | C.I-76 | proquinazid |
| M-D.77 | C.I-145 | proquinazid |
| M-D.78 | C.I-148 | proquinazid |

TABLE D-continued

Preferred combinations of preferred insecticidal compound I with preferred fungicidal compound II of group II.D:

| Mixture no. | Active compound I | Active compound II |
|---|---|---|
| M-D.79 | C.I-199 | proquinazid |
| M-D.80 | C.I-202 | proquinazid |
| M-D.81 | C.I-235 | proquinazid |
| M-D.82 | C.I-238 | proquinazid |
| M-D.83 | C.I-240 | proquinazid |
| M-D.84 | C.I-244 | proquinazid |
| M-D.85 | C.I-247 | proquinazid |
| M-D.86 | C.I-307 | proquinazid |
| M-D.87 | C.I-310 | proquinazid |
| M-D.88 | C.I-361 | proquinazid |
| M-D.89 | C.I-364 | proquinazid |
| M-D.90 | C.I-397 | proquinazid |
| M-D.91 | C.I-400 | proquinazid |
| M-D.92 | C.I-402 | proquinazid |
| M-D.93 | C.I-406 | proquinazid |
| M-D.94 | C.I-409 | proquinazid |
| M-D.95 | C.I-469 | proquinazid |
| M-D.96 | C.I-472 | proquinazid |
| M-D.97 | C.I-37 | pyrimethanil |
| M-D.98 | C.I-40 | pyrimethanil |
| M-D.99 | C.I-73 | pyrimethanil |
| M-D.100 | C.I-76 | pyrimethanil |
| M-D.101 | C.I-145 | pyrimethanil |
| M-D.102 | C.I-148 | pyrimethanil |
| M-D.103 | C.I-199 | pyrimethanil |
| M-D.104 | C.I-202 | pyrimethanil |
| M-D.105 | C.I-235 | pyrimethanil |
| M-D.106 | C.I-238 | pyrimethanil |
| M-D.107 | C.I-240 | pyrimethanil |
| M-D.108 | C.I-244 | pyrimethanil |
| M-D.109 | C.I-247 | pyrimethanil |
| M-D.110 | C.I-307 | pyrimethanil |
| M-D.111 | C.I-310 | pyrimethanil |
| M-D.112 | C.I-361 | pyrimethanil |
| M-D.113 | C.I-364 | pyrimethanil |
| M-D.114 | C.I-397 | pyrimethanil |
| M-D.115 | C.I-400 | pyrimethanil |
| M-D.116 | C.I-402 | pyrimethanil |
| M-D.117 | C.I-406 | pyrimethanil |
| M-D.118 | C.I-409 | pyrimethanil |
| M-D.119 | C.I-469 | pyrimethanil |
| M-D.120 | C.I-472 | pyrimethanil |
| M-D.121 | C.I-37 | tridemorph |
| M-D.122 | C.I-40 | tridemorph |
| M-D.123 | C.I-73 | tridemorph |
| M-D.124 | C.I-76 | tridemorph |
| M-D.125 | C.I-145 | tridemorph |
| M-D.126 | C.I-148 | tridemorph |
| M-D.127 | C.I-199 | tridemorph |
| M-D.128 | C.I-202 | tridemorph |
| M-D.129 | C.I-235 | tridemorph |
| M-D.130 | C.I-238 | tridemorph |
| M-D.131 | C.I-240 | tridemorph |
| M-D.132 | C.I-244 | tridemorph |
| M-D.133 | C.I-247 | tridemorph |
| M-D.134 | C.I-307 | tridemorph |
| M-D.135 | C.I-310 | tridemorph |
| M-D.136 | C.I-361 | tridemorph |
| M-D.137 | C.I-364 | tridemorph |
| M-D.138 | C.I-397 | tridemorph |
| M-D.139 | C.I-400 | tridemorph |
| M-D.140 | C.I-402 | tridemorph |
| M-D.141 | C.I-406 | tridemorph |
| M-D.142 | C.I-409 | tridemorph |
| M-D.143 | C.I-469 | tridemorph |
| M-D.144 | C.I-472 | tridemorph |
| M-D.145 | C.I-37 | 5-chloro-7-(4-methyl-piperidin-1-yl)-6-(2,4,6-trifluorophenyl)-[1,2,4]triazolo[1,5-a]pyrimidine |
| M-D.146 | C.I-40 | 5-chloro-7-(4-methyl-piperidin-1-yl)-6-(2,4,6-trifluorophenyl)-[1,2,4]triazolo[1,5-a]pyrimidine |
| M-D.147 | C.I-73 | 5-chloro-7-(4-methyl-piperidin-1-yl)-6-(2,4,6-trifluorophenyl)-[1,2,4]triazolo[1,5-a]pyrimidine |
| M-D.148 | C.I-76 | 5-chloro-7-(4-methyl-piperidin-1-yl)-6-(2,4,6-trifluorophenyl)-[1,2,4]triazolo[1,5-a]pyrimidine |
| M-D.149 | C.I-145 | 5-chloro-7-(4-methyl-piperidin-1-yl)-6-(2,4,6-trifluorophenyl)-[1,2,4]triazolo[1,5-a]pyrimidine |
| M-D.150 | C.I-148 | 5-chloro-7-(4-methyl-piperidin-1-yl)-6-(2,4,6-trifluorophenyl)-[1,2,4]triazolo[1,5-a]pyrimidine |
| M-D.151 | C.I-199 | 5-chloro-7-(4-methyl-piperidin-1-yl)-6-(2,4,6-trifluorophenyl)-[1,2,4]triazolo[1,5-a]pyrimidine |
| M-D.152 | C.I-202 | 5-chloro-7-(4-methyl-piperidin-1-yl)-6-(2,4,6-trifluorophenyl)-[1,2,4]triazolo[1,5-a]pyrimidine |
| M-D.153 | C.I-235 | 5-chloro-7-(4-methyl-piperidin-1-yl)-6-(2,4,6-trifluorophenyl)-[1,2,4]triazolo[1,5-a]pyrimidine |
| M-D.154 | C.I-238 | 5-chloro-7-(4-methyl-piperidin-1-yl)-6-(2,4,6-trifluorophenyl)-[1,2,4]triazolo[1,5-a]pyrimidine |
| M-D.155 | C.I-240 | 5-chloro-7-(4-methyl-piperidin-1-yl)-6-(2,4,6-trifluorophenyl)-[1,2,4]triazolo[1,5-a]pyrimidine |
| M-D.156 | C.I-244 | 5-chloro-7-(4-methyl-piperidin-1-yl)-6-(2,4,6-trifluorophenyl)-[1,2,4]triazolo[1,5-a]pyrimidine |
| M-D.157 | C.I-247 | 5-chloro-7-(4-methyl-piperidin-1-yl)-6-(2,4,6-trifluorophenyl)-[1,2,4]triazolo[1,5-a]pyrimidine |
| M-D.158 | C.I-307 | 5-chloro-7-(4-methyl-piperidin-1-yl)-6-(2,4,6-trifluorophenyl)-[1,2,4]triazolo[1,5-a]pyrimidine |
| M-D.159 | C.I-310 | 5-chloro-7-(4-methyl-piperidin-1-yl)-6-(2,4,6-trifluorophenyl)-[1,2,4]triazolo[1,5-a]pyrimidine |
| M-D.160 | C.I-361 | 5-chloro-7-(4-methyl-piperidin-1-yl)-6-(2,4,6-trifluorophenyl)-[1,2,4]triazolo[1,5-a]pyrimidine |
| M-D.161 | C.I-364 | 5-chloro-7-(4-methyl-piperidin-1-yl)-6-(2,4,6-trifluorophenyl)-[1,2,4]triazolo[1,5-a]pyrimidine |
| M-D.162 | C.I-397 | 5-chloro-7-(4-methyl-piperidin-1-yl)-6-(2,4,6-trifluorophenyl)-[1,2,4]triazolo[1,5-a]pyrimidine |
| M-D.163 | C.I-400 | 5-chloro-7-(4-methyl-piperidin-1-yl)-6-(2,4,6-trifluorophenyl)-[1,2,4]triazolo[1,5-a]pyrimidine |
| M-D.164 | C.I-402 | 5-chloro-7-(4-methyl-piperidin-1-yl)-6-(2,4,6-trifluorophenyl)-[1,2,4]triazolo[1,5-a]pyrimidine |
| M-D.165 | C.I-406 | 5-chloro-7-(4-methyl-piperidin-1-yl)-6-(2,4,6- |

TABLE D-continued

Preferred combinations of preferred insecticidal compound I with preferred fungicidal compound II of group II.D:

| Mixture no. | Active compound I | Active compound II |
|---|---|---|
| | | trifluorophenyl)-[1,2,4]triazolo[1,5-a]pyrimidine |
| M-D.166 | C.I-409 | 5-chloro-7-(4-methyl-piperidin-1-yl)-6-(2,4,6-trifluorophenyl)-[1,2,4]triazolo[1,5-a]pyrimidine |
| M-D.167 | C.I-469 | 5-chloro-7-(4-methyl-piperidin-1-yl)-6-(2,4,6-trifluorophenyl)-[1,2,4]triazolo[1,5-a]pyrimidine |
| M-D.168 | C.I-472 | 5-chloro-7-(4-methyl-piperidin-1-yl)-6-(2,4,6-trifluorophenyl)-[1,2,4]triazolo[1,5-a]pyrimidine |
| M-D.169 | C.I-37 | iprodione |
| M-D.170 | C.I-40 | iprodione |
| M-D.171 | C.I-73 | iprodione |
| M-D.172 | C.I-76 | iprodione |
| M-D.173 | C.I-145 | iprodione |
| M-D.174 | C.I-148 | iprodione |
| M-D.175 | C.I-199 | iprodione |
| M-D.176 | C.I-202 | iprodione |
| M-D.177 | C.I-235 | iprodione |
| M-D.178 | C.I-238 | iprodione |
| M-D.179 | C.I-240 | iprodione |
| M-D.180 | C.I-244 | iprodione |
| M-D.181 | C.I-247 | iprodione |
| M-D.182 | C.I-307 | iprodione |
| M-D.183 | C.I-310 | iprodione |
| M-D.184 | C.I-361 | iprodione |
| M-D.185 | C.I-364 | iprodione |
| M-D.186 | C.I-397 | iprodione |
| M-D.187 | C.I-400 | iprodione |
| M-D.188 | C.I-402 | iprodione |
| M-D.189 | C.I-406 | iprodione |
| M-D.190 | C.I-409 | iprodione |
| M-D.191 | C.I-469 | iprodione |
| M-D.192 | C.I-472 | iprodione |

TABLE E

Preferred combinations of preferred insecticidal compound I with preferred fungicidal compound II of group II.E:

| Mixture no. | Active compound I | Active compound II |
|---|---|---|
| M-E.1 | C.I-37 | maneb |
| M-E.2 | C.I-40 | maneb |
| M-E.3 | C.I-73 | maneb |
| M-E.4 | C.I-76 | maneb |
| M-E.5 | C.I-145 | maneb |
| M-E.6 | C.I-148 | maneb |
| M-E.7 | C.I-199 | maneb |
| M-E.8 | C.I-202 | maneb |
| M-E.9 | C.I-235 | maneb |
| M-E.10 | C.I-238 | maneb |
| M-E.11 | C.I-240 | maneb |
| M-E.12 | C.I-244 | maneb |
| M-E.13 | C.I-247 | maneb |
| M-E.14 | C.I-307 | maneb |
| M-E.15 | C.I-310 | maneb |
| M-E.16 | C.I-361 | maneb |
| M-E.17 | C.I-364 | maneb |
| M-E.18 | C.I-397 | maneb |
| M-E.19 | C.I-400 | maneb |
| M-E.20 | C.I-402 | maneb |
| M-E.21 | C.I-406 | maneb |
| M-E.22 | C.I-409 | maneb |
| M-E.23 | C.I-469 | maneb |
| M-E.24 | C.I-472 | maneb |
| M-E.25 | C.I-37 | mancozeb |
| M-E.26 | C.I-40 | mancozeb |
| M-E.27 | C.I-73 | mancozeb |
| M-E.28 | C.I-76 | mancozeb |
| M-E.29 | C.I-145 | mancozeb |
| M-E.30 | C.I-148 | mancozeb |
| M-E.31 | C.I-199 | mancozeb |
| M-E.32 | C.I-202 | mancozeb |
| M-E.33 | C.I-235 | mancozeb |
| M-E.34 | C.I-238 | mancozeb |
| M-E.35 | C.I-240 | mancozeb |
| M-E.36 | C.I-244 | mancozeb |
| M-E.37 | C.I-247 | mancozeb |
| M-E.38 | C.I-307 | mancozeb |
| M-E.39 | C.I-310 | mancozeb |
| M-E.40 | C.I-361 | mancozeb |
| M-E.41 | C.I-364 | mancozeb |
| M-E.42 | C.I-397 | mancozeb |
| M-E.43 | C.I-400 | mancozeb |
| M-E.44 | C.I-402 | mancozeb |
| M-E.45 | C.I-406 | mancozeb |
| M-E.46 | C.I-409 | mancozeb |
| M-E.47 | C.I-469 | mancozeb |
| M-E.48 | C.I-472 | mancozeb |
| M-E.49 | C.I-37 | metiram |
| M-E.50 | C.I-40 | metiram |
| M-E.51 | C.I-73 | metiram |
| M-E.52 | C.I-76 | metiram |
| M-E.53 | C.I-145 | metiram |
| M-E.54 | C.I-148 | metiram |
| M-E.55 | C.I-199 | metiram |
| M-E.56 | C.I-202 | metiram |
| M-E.57 | C.I-235 | metiram |
| M-E.58 | C.I-238 | metiram |
| M-E.59 | C.I-240 | metiram |
| M-E.60 | C.I-244 | metiram |
| M-E.61 | C.I-247 | metiram |
| M-E.62 | C.I-307 | metiram |
| M-E.63 | C.I-310 | metiram |
| M-E.64 | C.I-361 | metiram |
| M-E.65 | C.I-364 | metiram |
| M-E.66 | C.I-397 | metiram |
| M-E.67 | C.I-400 | metiram |
| M-E.68 | C.I-402 | metiram |
| M-E.69 | C.I-406 | metiram |
| M-E.70 | C.I-409 | metiram |
| M-E.71 | C.I-469 | metiram |
| M-E.72 | C.I-472 | metiram |
| M-E.73 | C.I-37 | thiram |
| M-E.74 | C.I-40 | thiram |
| M-E.75 | C.I-73 | thiram |
| M-E.76 | C.I-76 | thiram |
| M-E.77 | C.I-145 | thiram |
| M-E.78 | C.I-148 | thiram |
| M-E.79 | C.I-199 | thiram |
| M-E.80 | C.I-202 | thiram |
| M-E.81 | C.I-235 | thiram |
| M-E.82 | C.I-238 | thiram |
| M-E.83 | C.I-240 | thiram |
| M-E.84 | C.I-244 | thiram |
| M-E.85 | C.I-247 | thiram |
| M-E.86 | C.I-307 | thiram |
| M-E.87 | C.I-310 | thiram |
| M-E.88 | C.I-361 | thiram |
| M-E.89 | C.I-364 | thiram |
| M-E.90 | C.I-397 | thiram |
| M-E.91 | C.I-400 | thiram |
| M-E.92 | C.I-402 | thiram |
| M-E.93 | C.I-406 | thiram |
| M-E.94 | C.I-409 | thiram |
| M-E.95 | C.I-469 | thiram |
| M-E.96 | C.I-472 | thiram |

TABLE F

Preferred combinations of preferred insecticidal compound I with preferred fungicidal compound II of group II.F:

| Mixture no. | Active compound I | Active compound II |
|---|---|---|
| M-F.1 | C.I-37 | chlorothalonil |
| M-F.2 | C.I-40 | chlorothalonil |
| M-F.3 | C.I-73 | chlorothalonil |
| M-F.4 | C.I-76 | chlorothalonil |
| M-F.5 | C.I-145 | chlorothalonil |
| M-F.6 | C.I-148 | chlorothalonil |
| M-F.7 | C.I-199 | chlorothalonil |
| M-F.8 | C.I-202 | chlorothalonil |
| M-F.9 | C.I-235 | chlorothalonil |
| M-F.10 | C.I-238 | chlorothalonil |
| M-F.11 | C.I-240 | chlorothalonil |
| M-F.12 | C.I-244 | chlorothalonil |
| M-F.13 | C.I-247 | chlorothalonil |
| M-F.14 | C.I-307 | chlorothalonil |
| M-F.15 | C.I-310 | chlorothalonil |
| M-F.16 | C.I-361 | chlorothalonil |
| M-F.17 | C.I-364 | chlorothalonil |
| M-F.18 | C.I-397 | chlorothalonil |
| M-F.19 | C.I-400 | chlorothalonil |
| M-F.20 | C.I-402 | chlorothalonil |
| M-F.21 | C.I-406 | chlorothalonil |
| M-F.22 | C.I-409 | chlorothalonil |
| M-F.23 | C.I-469 | chlorothalonil |
| M-F.24 | C.I-472 | chlorothalonil |
| M-F.25 | C.I-37 | dithianon |
| M-F.26 | C.I-40 | dithianon |
| M-F.27 | C.I-73 | dithianon |
| M-F.28 | C.I-76 | dithianon |
| M-F.29 | C.I-145 | dithianon |
| M-F.30 | C.I-148 | dithianon |
| M-F.31 | C.I-199 | dithianon |
| M-F.32 | C.I-202 | dithianon |
| M-F.33 | C.I-235 | dithianon |
| M-F.34 | C.I-238 | dithianon |
| M-F.35 | C.I-240 | dithianon |
| M-F.36 | C.I-244 | dithianon |
| M-F.37 | C.I-247 | dithianon |
| M-F.38 | C.I-307 | dithianon |
| M-F.39 | C.I-310 | dithianon |
| M-F.40 | C.I-361 | dithianon |
| M-F.41 | C.I-364 | dithianon |
| M-F.42 | C.I-397 | dithianon |
| M-F.43 | C.I-400 | dithianon |
| M-F.44 | C.I-402 | dithianon |
| M-F.45 | C.I-406 | dithianon |
| M-F.46 | C.I-409 | dithianon |
| M-F.47 | C.I-469 | dithianon |
| M-F.48 | C.I-472 | dithianon |
| M-F.49 | C.I-37 | metrafenone |
| M-F.50 | C.I-40 | metrafenone |
| M-F.51 | C.I-73 | metrafenone |
| M-F.52 | C.I-76 | metrafenone |
| M-F.53 | C.I-145 | metrafenone |
| M-F.54 | C.I-148 | metrafenone |
| M-F.55 | C.I-199 | metrafenone |
| M-F.56 | C.I-202 | metrafenone |
| M-F.57 | C.I-235 | metrafenone |
| M-F.58 | C.I-238 | metrafenone |
| M-F.59 | C.I-240 | metrafenone |
| M-F.60 | C.I-244 | metrafenone |
| M-F.61 | C.I-247 | metrafenone |
| M-F.62 | C.I-307 | metrafenone |
| M-F.63 | C.I-310 | metrafenone |
| M-F.64 | C.I-361 | metrafenone |
| M-F.65 | C.I-364 | metrafenone |
| M-F.66 | C.I-397 | metrafenone |
| M-F.67 | C.I-400 | metrafenone |
| M-F.68 | C.I-402 | metrafenone |
| M-F.69 | C.I-406 | metrafenone |
| M-F.70 | C.I-409 | metrafenone |
| M-F.71 | C.I-469 | metrafenone |
| M-F.72 | C.I-472 | metrafenone |
| M-F.73 | C.I-37 | phosphorous acid |
| M-F.74 | C.I-40 | phosphorous acid |
| M-F.75 | C.I-73 | phosphorous acid |
| M-F.76 | C.I-76 | phosphorous acid |
| M-F.77 | C.I-145 | phosphorous acid |
| M-F.78 | C.I-148 | phosphorous acid |
| M-F.79 | C.I-199 | phosphorous acid |
| M-F.80 | C.I-202 | phosphorous acid |
| M-F.81 | C.I-235 | phosphorous acid |
| M-F.82 | C.I-238 | phosphorous acid |
| M-F.83 | C.I-240 | phosphorous acid |
| M-F.84 | C.I-244 | phosphorous acid |
| M-F.85 | C.I-247 | phosphorous acid |
| M-F.86 | C.I-307 | phosphorous acid |
| M-F.87 | C.I-310 | phosphorous acid |
| M-F.88 | C.I-361 | phosphorous acid |
| M-F.89 | C.I-364 | phosphorous acid |
| M-F.90 | C.I-397 | phosphorous acid |
| M-F.91 | C.I-400 | phosphorous acid |
| M-F.92 | C.I-402 | phosphorous acid |
| M-F.93 | C.I-406 | phosphorous acid |
| M-F.94 | C.I-409 | phosphorous acid |
| M-F.95 | C.I-469 | phosphorous acid |
| M-F.96 | C.I-472 | phosphorous acid |
| M-F.97 | C.I-37 | flusulfamide |
| M-F.98 | C.I-40 | flusulfamide |
| M-F.99 | C.I-73 | flusulfamide |
| M-F.100 | C.I-76 | flusulfamide |
| M-F.101 | C.I-145 | flusulfamide |
| M-F.102 | C.I-148 | flusulfamide |
| M-F.103 | C.I-199 | flusulfamide |
| M-F.104 | C.I-202 | flusulfamide |
| M-F.105 | C.I-235 | flusulfamide |
| M-F.106 | C.I-238 | flusulfamide |
| M-F.107 | C.I-240 | flusulfamide |
| M-F.108 | C.I-244 | flusulfamide |
| M-F.109 | C.I-247 | flusulfamide |
| M-F.110 | C.I-307 | flusulfamide |
| M-F.111 | C.I-310 | flusulfamide |
| M-F.112 | C.I-361 | flusulfamide |
| M-F.113 | C.I-364 | flusulfamide |
| M-F.114 | C.I-397 | flusulfamide |
| M-F.115 | C.I-400 | flusulfamide |
| M-F.116 | C.I-402 | flusulfamide |
| M-F.117 | C.I-406 | flusulfamide |
| M-F.118 | C.I-409 | flusulfamide |
| M-F.119 | C.I-469 | flusulfamide |
| M-F.120 | C.I-472 | flusulfamide |

Pests and Fungi

The mixtures of the present invention have excellent activity against a broad spectrum of phytopathogenic fungi and animal pests.

Animal Pests

The mixtures of the present invention have excellent activity against a broad spectrum of animal pests.

They are in particular suitable for efficiently controlling arthropodal pests such as arachnids, myriapedes and insects as well as nematodes.

In particular, they are suitable for controlling insect pests, such as insects from the order of
lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis*

*armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica* 12-punctata *Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci,* termites (Isopters), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus;* cockroaches (Blattaria—Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis;* bugs, aphids, leafhoppers, whiteflies, scale insects, cicadas (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis goSsypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribisnigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina;* arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinaei, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis; Araneida,* e.g. *Latrodectus mactans,* and *Loxosceles reclusa;* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

They are also suitable for controlling Nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

They are also useful for controlling arachnids (Arachnoidea), such as acarians (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis.*

Phytopathogenic Fungi

The mixtures of the present invention have excellent activity against a broad spectrum of phytopathogenic fungi Ascomycetes, Basidiomycetes, Deuteromycetes and Peronosporomycetes (syn. Oomycetes). Some of them are systemically effective and can be employed in crop protection as foliar fungicides, as fungicides for seed dressing and as soil fungicides. They can also be used for treating seed.

They are particularly important in the control of a multitude of fungi on various cultivated plants, such as wheat, rye, barley, oats, rice, corn, lawns, bananas, cotton, soybean, coffee, sugar cane, grapevines, fruits and ornamental plants, and vegetables such as cucumbers, beans, tomatoes, potatoes and cucurbits, and on the seeds of these plants.

They are especially suitable for controlling the following plant diseases:

*Alternaria* species on vegetables, oilseed rape, sugar beet and fruit and rice, for example, *A. solani* or *A. alternata* on potatoes and tomatoes;

*Aphanomyces* species on sugar beet and vegetables;

*Ascochyta* species on cereals and vegetables;

*Bipolaris* and *Drechslera* species on corn, cereals, rice and lawns, for example, *D. maydis* on corn;

*Blumeria graminis* (powdery mildew) on cereals;

*Botrytis cinerea* (gray mold) on strawberries, vegetables, flowers and grapevines;

*Bremia lactucae* on lettuce;

*Cercospora* species on corn, soybeans, rice and sugar beet;

*Cochliobolus* species on corn, cereals, rice, for example *Cochliobolus sativus* on cereals, *Cochliobolus miyabeanus* on rice;

*Colletotricum* species on soybeans and cotton;

*Drechslera* species, *Pyrenophora* species on corn, cereals, rice and lawns, for example, *D. teres* on barley or *D. tritici-repentis* on wheat;

Esca on grapevines, caused by *Phaeoacremonium chlamydosporium, Ph. Aleophilum* and *Formitipora punctata* (syn. *Phellinus punctatus*);

*Exserohilum* species on corn;

*Erysiphe cichoracearum* and *Sphaerotheca fuliginea* on cucumbers;

*Fusarium* and *Verticillium* species on various plants, for example, *F. graminearum* or *F. culmorum* on cereals or *F. oxysporum* on a multitude of plants, such as, for example, tomatoes;

*Gaeumanomyces graminis* on cereals;

*Gibberella* species on cereals and rice (for example *Gibberella fujikuroi* on rice);

Grainstaining complex on rice;
*Helminthosporium* species on corn and rice;
*Michrodochium nivale* on cereals;
*Mycosphaerella* species on cereals, bananas and peanuts, for example, *M. graminicola* on wheat or *M. fijiensis* on bananas;
*Peronospora* species on cabbage and bulbous plants, for example, *P. brassicae* on cabbage or *P. destructor* on onions;
*Phakopsara pachyrhizi* and *Phakopsara meibomiae* on soybeans;
*Phomopsis* species on soybeans and sunflowers;
*Phytophthora infestans* on potatoes and tomatoes;
*Phytophthora* species on various plants, for example, *P. capsici* on bell pepper;
*Plasmopara viticola* on grapevines;
*Podosphaera leucotricha* on apples;
*Pseudocercosporella herpotrichoides* on cereals;
*Pseudoperonospora* on various plants, for example, *P. cubensis* on cucumber or *P. humili* on hops;
*Puccinia* species on various plants, for example, *P. triticina, P. striformins, P. hordei* or *P. graminis* on cereals or *P. asparagi* on asparagus;
*Pyricularia oryzae, Corticium sasakii, Sarocladium oryzae, S. attenuatum, Entyloma oryzae* on rice;
*Pyricularia grisea* on lawns and cereals;
*Pythium* spp. on lawns, rice, corn, cotton, oilseed rape, sunflowers, sugar beet, vegetables and other plants, for example, *P. ultiumum* on various plants, *P. aphanidermatum* on lawns;
*Rhizoctonia* species on cotton, rice, potatoes, lawns, corn, oilseed rape, sugar beet, vegetables and on various plants, for example, *R. solani* on beet and various plants;
*Rhynchosporium secalis* on barley, rye and triticale;
*Sclerotinia* species on oilseed rape and sunflowers;
*Septoria tritici* and *Stagonospora nodorum* on wheat;
*Erysiphe* (syn. *Uncinula*) *necator* on grapevines;
*Setospaeria* species on corn and lawns;
*Sphacelotheca reilinia* on corn;
*Thievaliopsis* species on soybeans and cotton;
*Tilletia* species on cereals;
*Ustilago* species on cereals, corn and sugar cane, for example, *U. maydis* on corn;
*Venturia* species (scab) on apples and pears, for example, *V. inaequalis* on apples.

The mixtures according to the invention are also suitable for controlling harmful fungi in the protection of materials (for example wood, paper, paint dispersions, fibers or fabrics) and in the protection of stored products. In the protection of wood, particular attention is paid to the following harmful fungi: Ascomycetes, such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and Zygomycetes, such as *Mucor* spp., additionally in the protection of materials the following yeasts: *Candida* spp. and *Saccharomyces cerevisae*.

Formulations

The pesticidal mixtures according to the present invention can be converted into the customary formulations, for example solutions, emulsions, suspensions, dusts, powders, pastes and granules. The use form depends on the particular intended purpose; in each case, it should ensure a fine and even distribution of the compounds according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally gelling agents.

Examples of suitable solvents are water, aromatic solvents (for example Solvesso™ products, xylene), paraffins (for example mineral oil fractions), alcohols (for example methanol, butanol, pentanol, benzyl alcohol), ketones (for example cyclohexanone, gamma-butyrolactone), pyrrolidones (NMP (N-methyl-pyrrolidone), NOP(N-octyl-pyrrolidone)), acetates (glycol diacetate), glycols, fatty acid dimethylamides, fatty acids and fatty acid esters. In principle, solvent mixtures may also be used.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropyl-ene, lauryl alcohol polyglycol ether acetal, sorbitol esters, lignosulfite waste liquors and methylcellulose.

Substances, which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

An example of a gelling agent is carrageen (Satiagel®)

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds. In this case, the active compounds are employed in a purity of from 90% to 100% by weight, preferably 95% to 100% by weight (according to NMR spectrum or HLPC spectrum).

For seed treatment purposes, respective formulations can be diluted 2-10 fold leading to concentrations in the ready to use preparations of 0.01 to 60% by weight active compounds by weight, preferably 0.1 to 40% by weight.

The mixtures of the present invention can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier.

However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:

1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetters or other auxiliaries are added. The active compound(s) dissolve(s) upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of gelling agent wetters and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable powders (DP, DS)

5 parts by weight of the active compound(s) are ground finely and mixed intimately with 95 parts by weight of finely divided kaolin. This gives a dustable product having 5% (w/w) of active compound(s).

J) Granules (GR, FG, GG, MG)

0.5 part by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

Various types of oils, wetters, adjuvants or bactericides may be added to the active ingredients. Suitable adjuvants in this context are, in particular: organically modified polysiloxanes, e.g. BREAK THRU S 240™; alcohol alkoxylates, e.g. ATPLUS 245™, ATPLUS MBA 1303™, PLURAFAC LF 300™ and LUTENSOL ON 30™; EO/PO block polymers, e.g. PLURONIC RPE 2035™ and GENAPOL B™; alcohol ethoxylates, e.g. LUTENSOL XP 80™; and sodium dioctyl-sulfosuccinate, e.g. LEOPHEN RA™.

Compositions of this invention may further contain other active ingredients than those listed above. For example further insecticides or fungicides, herbicides, fertilizers such as ammonium nitrate, urea, potash, and superphosphate, phytotoxicants and plant growth regulators and safeners. These agents usually are admixed with the agents according to the invention in a weight ratio of 1:10 to 10:1.

The pesticidal mixtures may comprise additionally one or more further insecticidal compound III of the following list M of pesticides. The list is intended to illustrate the possible combinations, but not to impose any limitation:

M.1. Organo(thio)phosphates: acephate, azamethiphos, azinphosethyl, azinphosmethyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroids: acrinathrin, allethrin, d-cis-trans allethrin, d-trans allethrin, bifenthrin, bioallethrin, bioallethrin S-cyl-clopentenyl, bioresmethrin, cyprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide; (R)—, (S)-3-Chlor-N1-{2-methyl-4-[1,2,2,2-tetrafluor-1-(trifluormethyl)ethyl]phenyl}-N2-(1-methyl-2-methylsulfonylethyl)phthalamid (M21.1)

M.22. Various: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, 4-But-2-ynyloxy-6-(3,5-dimethyl-piperidin-1-yl)-2-fluoro-pyrimidine (M22.1), 3-Benzoylamino-N-[2,6-dimethyl-4-(1,2,2,2-tetrafluoro-1-trifluoromethyl-ethyl)-phenyl]-2-fluoro-benzamide (M22.2), 4-[5-(3,5-Dichloro-phenyl)-5-trifluoromethyl-4,5-dihydro-isoxazol-3-yl]-2-methyl-N-pyridin-2-ylmethyl-benzamide (M22.3), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.4), 4-[5-(3,5-Dichloro-phenyl)-5-trifluoromethyl-4,5-dihydro-isoxazol-3-yl]-2-methyl-N-thiazol-2-ylmethyl-benzamide (M22.5), 4-[5-(3,5-Dichloro-phenyl)-5-trifluoromethyl-4,5-dihydro-isoxazol-3-yl]-2-methyl-N-(tetrahydro-furan-2-yl-methyl)-benzamide (M22.6), 4-{[(6-Bromopyrid-3-yl)methyl](2-fluoroethyl)amino}furan-2(5H)-on (M22.7), 4-{[(6-

Fluoropyrid-3-yl)methyl](2,2-difluoroethyl)amino}furan-2 (5H)-on(M22.8), 4-{[(2-Chloro1,3-thiazolo-5-yl)methyl](2-fluoroethyl)amino}furan-2(5H)-on (M22.9), 4-{[(6-Chloropyrid-3-yl)methyl](2-fluoroethyl)amino}furan-2 (5H)-on (M22.10), 4-{[(6-Chloropyrid-3-yl)methyl](2,2-difluoroethyl)amino}furan-2(5H)-on(M22.11), 4-{[(6-Chloro-5-fluoropyrid-3-yl)methyl]methyl)amino}furan-2 (5H)-on (M22.12), 4-{[(5,6-Dichloropyrid-3-yl)methyl](2-fluoroethyl)amino}furan-2(5H)-on (M22.13), 4-{[(6-Chloro-5-fluoropyrid-3-yl)methyl](cyclopropyl) amino}furan-2(5H)-on (M22.14), 4-{[(6-Chloropyrid-3-yl) methyl](cyclopropyl)amino}furan-2(5H)-on (M22.15), 4-{ [(6-Chloropyrid-3-yl)methyl](methyl)amino}furan-2(5H)-on (M22.16), Cyclopropaneacetic acid, 1,1'-[(3S,4R,4aR,6S, 6aS,12R,12aS,12bS)-4-[[(2-cyclopropylacetyl)oxy] methyl]-1,3,4,4a,5,6,6a,12,12a,12b-decahydro-[2-hydroxy-4,6a,12b-trimethyl-1'-oxo-9-(3-pyridinyl)-2H,11H-naphtho [2,1-b]pyrano[3,4-e]pyran-3,6-diyl]ester (M22.17), 8-(2-Cyclopropylmethoxy-4-methyl-phenoxy)-3-(6-methyl-pyridazin-3-yl)-3-aza-bicyclo[3.2.1]octane (M22.18), M.23. N—R'-2,2-dihalo-1-R"cyclo-propanecarboxamide-2-(2,6-dichloro-α,α,α-trifluoro-p-tolyl)hydrazone or N—R'-2, 2-di(R''')propionamide-2-(2,6-dichloro-α,α,α-trifluoro-p-tolyl)-hydrazone, wherein R' is methyl or ethyl, halo is chloro or bromo, R'' is hydrogen or methyl and R''' is methyl or ethyl;

M.24. Anthranilamides: chloranthraniliprole, cyantraniliprole,

5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M24.1), 5-Bromo-2-(3-chloro-pyridin-2-yl)-2H-pyrazole-3-carboxylic acid [2-chloro-4-cyano-6-(1-cyclopropyl-ethyl-carbamoyl)-phenyl]-amide (M24.2), 5-Bromo-2-(3-chloro-pyridin-2-yl)-2H-pyrazole-3-carboxylic acid [2-bromo-4-cyano-6-(1-cyclopropyl-ethyl-carbamoyl)-phenyl]-amide (M24.3), 5-Bromo-2-(3-chloro-pyridin-2-yl)-2H-pyrazole-3-carboxylic acid [2-bromo-4-chloro-6-(1-cyclopropyl-ethyl-carbamoyl)-phenyl]-amide (M24.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M24.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M24.6), M.25. Malononitrile compounds: $CF_2HCF_2CF_2CF_2CH_2C(CN)_2CH_2CH_2CF_3$, (2-(2,2,3,3,4,4,5,5-octafluoropentyl)-2-(3,3,3-trifluoro-propyl)malononitrile), $CF_2HCF_2CF_2CF_2CH_2C(CN)_2CH_2CH_2CF_2CF_3$ (2-(2,2,3,3,4,4,5,5-octafluoropentyl)-2-(3,3,4,4,4-pentafluorobutyl)-malonodinitrile);

M.26. Microbial disruptors: *Bacillus thuringiensis* subsp. *Israelensi, Bacillus sphaericus, Bacillus thuringiensis* subsp. *Aizawai, Bacillus thuringiensis* subsp. *Kurstaki, Bacillus thuringiensis* subsp. *Tenebrionis;*

The commercially available compounds of the group M may be found in The Pesticide Manual, 13th Edition, British Crop Protection Council (2003) among other publications.

Lepimectin is known from Agro Project, PJB Publications Ltd, November 2004. Benclothiaz and its preparation have been described in EP-A1454621. Methidathion and Paraoxon and their preparation have been described in Farm Chemicals Handbook, Volume 88, Meister Publishing Company, 2001. Metaflumizone and its preparation have been described in EP-A1462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. AKD 1022 and its preparation have been described in U.S. Pat. No. 6,300,348. Chloranthraniliprole has been described in WO 01/70671, WO 03/015519 and WO 05/118552. Cyantraniliprole has been described in WO 01/70671, WO 04/067528 and WO 05/118552. The anthranilamides M 24.1 to M 24.6 have been described in WO 2008/72743 and WO 200872783. The phthalamide M 21.1 is known from WO 2007/101540. Cyflumetofen and its preparation have been described in WO 04/080180. The aminoquinazolinone compound pyrifluquinazon has been described in EP A 109 7932. Sulfoximine sulfoxaflor has been described in WO 2006/060029 and WO 2007/149134. The alkynylether compound M22.1 is described e.g. in JP 2006131529. Organic sulfur compounds have been described in WO 2007060839. The carboxamide compound M 22.2 is known from WO 2007/83394. The oxazoline compounds M 22.3 to M 22.6 have been described in WO 2007/074789. The furanon compounds M 22.7 to M 22.16 have been described eg. in WO 2007/115644. The pyripyropene derivative M 22.17 has been described in WO 2008/66153 and WO 2008/108491. The pyridazin compound M 22.18 has been described in JP 2008/115155. The malononitrile compounds have been described in WO 02/089579, WO 02/090320, WO 02/090321, WO 04/006677, WO 05/068423, WO 05/068432 and WO 05/063694.

Those additional ingredients may be used sequentially or in combination with the above-described compositions, if appropriate also added only immediately prior to use (tank mix). For example, the plant(s) may be sprayed with a composition of this invention either before or after being treated with other active ingredients.

Applications

The one or more active compound(s) I and the one or more active compound(s) II can be applied according to different ways of applications, which are I. simultaneously, that is
   a) jointly (i.e. as mixture as such, e.g. a ready-to-use-formulation, or as tank mix) or
   b) separately (i.e. application via separate tanks), or
II. in succession separately, the sequence, in this case, generally not having any effect on the result of the control measures.

Therefore, the method for controlling harmful fungi and animal pests is carried out by the separate or joint application of at least one active compound I and at least one of the active compound II, or a mixture of at least one active compounds I and at least one of the active compound II, by spraying or dusting the seeds, the plants or the soils before or after sowing of the plants or before or after emergence of the plants.

The inventive mixtures or compositions of these mixtures can also be employed for protecting plants from attack or infestation by insects, acarids or nematodes comprising contacting a plant, or soil or water in which the plant is growing.

In the context of the present invention, the term plant refers to an entire plant, a part of the plant or the propagation material of the plant, that is, the seed or the seedling.

The mixtures of the present invention are employed as such or in form of compositions by treating the insects, the fungi or the plants, plant propagation materials, such as seeds, soil, surfaces, materials or rooms to be protected from insecticidal attack with a pesticidally effective amount of the active compounds. The application can be carried out both before and after the infection of the plants, plant propagation materials, such as seeds, soil, surfaces, materials or rooms by the insects.

The present invention also includes a method of combating animal pests and harmful fungi which comprises contacting the fungi and/or animal pests, their habit, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture according to the present invention.

Plants which can be treated with the inventive mixtures include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

Some of the inventive mixtures have systemic action and can therefore be used for the protection of the plant shoot against foliar pests as well as for the treatment of the seed and roots against soil pests.

The mixtures of compounds I and II or their corresponding formulations are applied by treating the harmful fungi and the animal pests, their habitat or the plants, seeds, soils, areas, materials or spaces to be kept free from them with a pesticidally effective amount of the mixture or, in the case of separate application, of the compounds I and II. Application can be before or after the infection by harmful fungi and/or animal pests.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The mixtures of the present invention and the compositions comprising them are particularly important in the control of a multitude of fungi and insects on various cultivated plants.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat. Protoc. 2007; 2(5):1225-35., Curr Opin Chem. Biol. 2006 October; 10(5): 487-91. Epub 2006 Aug. 28., Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example CLEARFIELD® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names ROUNDU-PREADY® (glyphosate) and LIBERTY® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. NEXERA® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of the inventive mixtures or of compositions comprising the mixtures needed to achieve an observable effect on growth, including the effects of necrosis, death, retardation, prevention, and removal, destruction, or otherwise diminishing the occurrence and activity of the target organism.

The pesticidally effective amount can vary for the various mixtures/compositions used in the invention. A pesticidally effective amount of the mixtures/compositions will also vary according to the prevailing conditions such as desired pesticidal effect and duration, weather, target species, locus, mode of application, and the like.

Preferred application methods are into water bodies, via soil, cracks and crevices, pastures, manure piles, sewers, into water, on floor, wall, or by perimeter spray application and bait.

Usually, mixtures of at least one compound I and at least one active compound II are employed. However, mixtures of at least one compound I with two or, if desired, more active components may also offer particular advantages.

Suitable further active components in the above sense are particularly the active compounds II mentioned at the outset and in particular the preferred active compounds II mentioned above.

The inventive mixtures and the compositions comprising them can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities).

In the case of soil treatment or of application to the pests dwelling place or nest, the quantity of active ingredient(s) ranges from 0.0001 to 500 g per 100 m$^2$, preferably from 0.001 to 20 g per 100 m$^2$.

Customary application rates in the protection of materials are, for example, from 0.01 g to 1000 g of active compound(s) per m$^2$ treated material, desirably from 0.1 g to 50 g per m$^2$.

Pesticidal compositions for use in the impregnation of materials typically contain from 0.001 to 95 weight %, preferably from 0.1 to 45 weight %, and more preferably from 1 to 25 weight % of at least one repellent and/or insecticide.

For use in spray compositions, the content of the mixture of the active ingredients is from 0.001 to 80 weights %, preferably from 0.01 to 50 weight % and most preferably from 0.01 to 15 weight %.

In general, "synergistically effective amount" means that the one or more active compound(s) I and the one or more active compound(s) II are usually applied in a weight ratio of from 500:1 to 1:100, preferably from 20:1 to 1:50, in particular from 5:1 to 1:20. Depending on the nature of the compounds the employed weight ratio of compound(s) I and compound(s) II ranges can start from 100:1 to 1:100, preferably from 20:1 to 1:20, in particular from 10:1 to 1:10.

Further active compounds are, if desired, mixed in a ratio of from 20:1 to 1:20 to the compound I.

Depending on the desired effect, the application rates of the mixtures according to the invention are from 5 g/ha to 2000 g/ha, preferably from 20 to 1500 g/ha, more preferably from 50 to 1000 g/ha and in particular from 50 to 750 g/ha. For use in treating crop plants, the rate of application of the mixture of the active ingredients of this invention may be in the range of 0.1 g to 4000 g per hectare, desirably from 25 g to 600 g per hectare, more desirably from 50 g to 500 g per hectare.

Correspondingly, the application rates for the compound(s) I are generally from 1 to 1000 g/ha, preferably from 10 to 900 g/ha, in particular from 20 to 750 g/ha.

Correspondingly, the application rates for the active compound II are generally from 1 to 2000 g/ha, preferably from 10 to 1500 g/ha, in particular from 40 to 1000 g/ha.

Methods to control infectious diseases transmitted by insects (e.g. malaria, dengue and yellow fever, lymphatic filariasis, and leishmaniasis) with the inventive mixtures and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a composition including the inventive mixtures, optionally a repellent and at least one binder.

Bait Formulations and Applications

The mixtures according to the invention can be applied to any and all developmental stages, such as egg, larva, pupa, and adult. The pests may be controlled by contacting the target pest, its food supply, habitat, breeding ground or its locus with a pesticidally effective amount of the inventive mixtures or of compositions comprising the mixtures.

"Locus" in general means a plant, seed, soil, area, material or environment in which pests or fungi are growing or may grow.

The mixtures according to the invention are effective through both contact and ingestion.

The inventive mixtures are effective through both contact (via soil, glass, wall, bed net, carpet, plant parts or animal parts), and ingestion (bait, or plant part) and through trophallaxis and transfer.

According to another preferred embodiment of the invention, for use against non crop pests such as ants, termites, wasps, flies, mosquitoes, crickets, locusts, or cockroaches the inventive mixtures are prepared into a bait preparation.

The bait can be a liquid, a solid or a semisolid preparation (e.g. a gel). The bait employed in the composition is a product which is sufficiently attractive to incite insects such as ants, termites, wasps, flies, mosquitoes, crickets etc. or cockroaches to eat it. This attractant may be chosen from feeding stimulants or para and/or sex pheromones readily known in the art.

For use in bait compositions, the typical content of active ingredient(s) is from 0.0001 weight % to 15 weight %, desirably from 0.001 weight % to 5% weight % of active compound. The composition used may also comprise other additives such as a solvent of the active material, a flavoring agent, a preserving agent, a dye or a bitter agent. Its attractiveness may also be enhanced by a special color, shape or texture.

According to a preferred embodiment of the invention, the mixtures according to the present invention are employed via soil application. Soil application is especially favorable for use against ants, termites, crickets, or cockroaches.

According to another preferred embodiment of the invention, for use against non crop pests such as ants, termites, wasps, flies, mosquitoes, crickets, locusts, or cockroaches the mixtures according to the present invention are prepared into a bait preparation.

Seed Treatment

The mixtures according to the present invention are also suitable for the treatment of seeds in order to protect the seed from harmful fungi and animal pests, in particular from soil-living fungi and insect pests and the resulting plant's roots and shoots against soil pests and foliar insects.

The protection of the resulting plant's roots and shoots is preferred.

The present invention therefore comprises therefore a method for the protection of seeds from insects, in particular from soil pests and of the seedlings' roots and shoots from harmful fungi and insects, in particular from soil and foliar insects, said method comprising contacting the seeds before sowing and/or after pregermination with mixtures according to the present invention.

Particularly preferred is a method, wherein the plant's roots and shoots are protected.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compounds. The term "coated with and/or containing" generally signifies that the active ingredients are for the most part on the surface of the propagation product at the time of application, although a greater or lesser part of the ingredient may penetrate into the propagation product, depending on the method of application. When the said propagation product are (re)planted, it may absorb the active ingredient.

Suitable seeds are seeds of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the mixtures according to the invention may also be used for the treatment seeds from plants, which tolerate the action of herbicides or fungicides or insecticides owing to breeding, including genetic engineering methods.

For example, the active mixtures can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the mixtures according to the present invention can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the mixtures is carried out by spraying or by dusting the seeds before sowing of the plants and before emergence of the plants.

In the treatment of seeds the corresponding formulations are applied by treating the seeds with an effective amount of the mixture according to the present invention. Herein, the application rates of the active compound(s) are generally from 0.1 g to 10 kg per 100 kg of seed, preferably from 1 g to 5 kg per 100 kg of seed, in particular from 1 g to 2.5 kg per 100 kg of seed. For specific crops such as lettuce the rate can be higher.

Compositions, which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient(s), 1-200 g/l Surfactant, 0 to 200 g/l antifreezing agent, 0 to 400 g/l of binder, 0 to 200 g/l of a pigment and up to 1 liter of a solvent, preferably water.

Preferred FS formulations of the active compounds for seed treatment usually comprise from 0.1 to 80% by weight (1 to 800 g/l) of the active ingredient(s), from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The invention also relates to seed comprising mixtures according to the present invention. The amount of the compound I or the agriculturally useful salt thereof will in general vary from 0.1 g to 10 kg per 100 kg of seed, preferably from 1 g to 5 kg per 100 kg of seed, more preferably from 1 g to 1000 g per 100 kg of seeds, most preferably from 1 g to 750 g per 100 kg of seeds, and in particular from 5 g to 500 g per 100 kg of seed.

EXAMPLES

Some of the preferred compound I examples are characterized by their physical data in the following table C.I.2. The characterization can be done by coupled High Performance Liquid Chromatography/mass spectrometry (HPLC/MS), by NMR or by their melting points.

The compounds were characterized by $^1$H-NMR. The signals are characterized by chemical shift (ppm) vs. tetramethylsilane, by their multiplicity and by their integral (relative number of hydrogen atoms given). The following abbreviations are used to characterize the multiplicity of the signals: M=multiplett, q=quartett, t=triplett, d=doublet and s=singulett.

The compounds were characterized by HPLC/MS. Analytical HPLC column: RP-18 column CHROMOLITH® Speed ROD from Merck KgaA, Germany). Elution: acetonitrile+0.1% trifluoroacetic acid (TFA)/water+0.1% trifluoroacetic acid (TFA) in a ratio of from 5:95 to 95:5 in 5 minutes at 40° C.

Specific compound examples of isoxazoline compounds of formula I:

TABLE C.I.2

| Compound example | Structure of compound I | HPLC-MS ($t_r$ = retention time) | $^1$H NMR (in CDCl$_3$): δ [ppm] |
|---|---|---|---|
| C.I.73 | | $t_r$ = 3.32 min; m = 494.0 | $^1$H-NMR (500 MHz, CDCl$_3$): δ = 8.50 (d, 1H), 7.95 (m, 1H), 7.90 (m, 2H), 7.70 (m, 3H), 7.52 (s, 2H), 7.40 (m, 1H), 7.35 (m, 1H), 7.25 (m, 1H), 4.75 (s, 2H), 4.10 (d, 1H), 3.75 (m, 1H). |
| C.I.235 | | $t_r$ = 3.40 min; m = 508.0 | $^1$H-NMR (500 MHz, CDCl$_3$): δ = 8.55 (m, 1H), 7.70 (m, 1H), 7.50 (m, 5H), 7.45 (s, 1H), 7.40 (m, 1H), 7.25 (m, 2H), 4.75 (d, 2H), 4.05 (d, 1H), 3.68 (d, 1H), 2.50 (s, 3H). |

TABLE C.I.2-continued

| Compound example | Structure of compound I | HPLC-MS ($t_r$ = retention time) | $^1$H NMR (in CDCl$_3$): δ [ppm] |
|---|---|---|---|
| C.I.397 | (structure) | $t_r$ = 3.59 min; m = 544.1 | $^1$H-NMR (500 MHz, CDCl$_3$): δ = 8.85 (m, 1H), 8.52 (m, 1H), 8.47 (m, 1H), 7.30-7.80 (m, 10H), 7.25 (m, 1H), 4.85 (m, 2H), 4.26 (d, 1H), 3.88 (d, 1H). |
| C.I.240 | (structure) | $t_r$ = 3.911 min; m = 556.1 | $^1$H-NMR (500 MHz, CDCl$_3$): δ = 7.42-7.58 (m, 6H), 7.01 (br dd, 1H), 6.77 (br. dd, 1H), 4.20 (d, 2H), 4.08 (d, 1H), 3.95 (m, 1H), 3.71 (d, 1H), 2.44 (s, 3H). |
| C.I.402 | (structure) | $t_r$ = 3.886 min; m = 592.0 | $^1$H-NMR (500 MHz, CDCl$_3$): δ = 8.84 (d, 1H), 8.30 (d, 1H), 7.46-7.72 (m, 7H), 6.88 (m, 1H), 6.81 (m, 1H), 4.29 (d, 2H), 4.26 (d, 1H), 3.97 (m, 2H), 3.90 (d, 1H), |

Biology

Synergism can be described as an interaction where the combined effect of two or more compounds is greater than the sum of the individual effects of each of the compounds. The presence of a synergistic effect in terms of percent control, between two mixing partners (X and Y) can be calculated using the Colby equation (Colby, S. R., 1967, Calculating Synergistic and Antagonistic Responses in Herbicide Combinations, Weeds, 15, 20-22):

$$E = \frac{XY}{100}$$

When the observed combined control effect is greater than the expected combined control effect (E), then the combined effect is synergistic.

The following tests can demonstrate the pesticidal effects and the control efficacy of the compounds and mixtures of this invention on specific pests. However, the pest control protection afforded by the mixtures is not limited to these species. In certain instances, combinations of a compound I of this invention with other pest control compounds or agents are found to exhibit synergistic effects against certain important pests.

The analysis of synergism of the mixtures can be determined using Colby's equation.

The visually determined percentages of infected leaf areas are converted into efficacies in % of the untreated control:

The efficacy (E) is calculated as follows using Abbot's formula:

$$E = (1-\alpha/\beta) \cdot 100$$

α corresponds to the fungicidal infection of the treated plants in % and

β corresponds to the fungicidal infection of the untreated (control) plants in %

An efficacy of 0 means that the infection level of the treated plants corresponds to that of the untreated control plants; an efficacy of 100 means that the treated plants are not infected.

The expected efficacies of mixtures of active compounds is determined using Colby's formula (Colby, S. R. "Calculating synergistic and antagonistic responses of herbicide Combinations", Weeds, 15, 20-22, 1967) and compared with the observed efficacies.

Colby's formula:
$$E = x+y-x \cdot y/100$$

E expected efficacy, expressed in % of the untreated control, when using the mixture of the active compounds A and B at the concentrations a and b x efficacy, expressed in % of the untreated control, when using the active compound A at the concentration a y efficacy, expressed in % of the untreated control, when using the active compound B at the concentration b Synergism is demonstrated, when the activity of the mixtures according to the invention is considerably higher than predicted using Colby's formula.

If not otherwise described, the active compounds, separately or jointly, are prepared as a stock solution comprising 0.25% by weight of active compounds in acetone or DMSO. 1% by weight of the emulsifier UNIPEROL® EL (wetting agent having emulsifying and dispersant action based on ethoxylated alkylphenols) is added to this solution, and the mixture is diluted with water to the desired concentration.

B.1 Pesticidal Action Against Fungi

The fungicidal action of the compounds of the formula I was demonstrated by the following experiments:

B.1.A) Microtiter Tests

The active substances were formulated separately as a stock solution in dimethyl sulfoxide (DMSO) at a concentration of 10 000 ppm.

The compound II flubenthiavalicarb (benthiavalicarb) was used as commercial finished formulations and diluted with water to the stated concentration of the active compound.

Fungicidal Test Example 1:
Activity Against the Late Blight Pathogen *Phytophthora infestans* in the Microtiter Test (Phytin)

The stock solution was pipetted into a microtiter plate (MTP) and diluted to the stated active substance concentration using a pea juice-based aqueous nutrient medium for fungi. An aqueous zoospore suspension of *Phytophthora infestans* was then added. The plates were placed in a water vapor-saturated chamber at temperatures of 18° C. Using an absorption photometer, the MTPs were measured at 405 nm on day 7 after the inoculation.

Fungicidal Test Example 2:
Activity Against the Grey Mold *Botrytis cinerea* in the Microtiterplate Test (Botrci)

The stock solutions were mixed according to the ratio, pipetted onto a micro titer plate (MTP) and diluted with water to the stated concentrations. A spore suspension of Botrci cinerea in an aqueous biomalt solution was then added. The plates were placed in a water vapor-saturated chamber at a temperature of 18° C. Using an absorption photometer, the MTPs were measured at 405 nm 7 days after the inoculation.

Fungicidal Test Example 3:
Activity Against Rice Blast *Pyricularia oryzae* in the Microtiterplate Test (Pyrior)

The stock solution was pipetted into a microtiter plate (MTP) and diluted to the stated active substance concentration using a malt-based aqueous nutrient medium for fungi. An aqueous spore suspension of *Pyricularia oryzae* was then added. The plates were placed in a water vapor-saturated chamber at temperatures of 18° C. Using an absorption photometer, the microtiter plates were measured at 405 nm on day 7 after the inoculation.

Fungicidal Test Example 4:
Activity Against Leaf Blotch on Wheat Caused by *Septoria tritici* (Septtr)

The stock solution was pipetted into a microtiter plate (MTP) and diluted to the stated active substance concentration using a malt-based aqueous nutrient medium for fungi. An aqueous spore suspension of *Septoria tritici* was then added. The plates were placed in a water vapor-saturated chamber at temperatures of 18° C. Using an absorption photometer, the microtiter plates were measured at 405 nm on day 7 after the inoculation.

The measured parameters of the fungicidal tests were compared to the growth of the active compound-free control variant (100%) and the fungus-free and active compound-free blank value to determine the relative growth in % of the pathogens in the respective active compounds. These percentages were converted into efficacies. An efficacy of 0 means that the growth level of the pathogens corresponds to that of the untreated control; an efficacy of 100 means that the pathogens were not growing.

As explained above, the expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Results

Test Compounds I of Formula I:

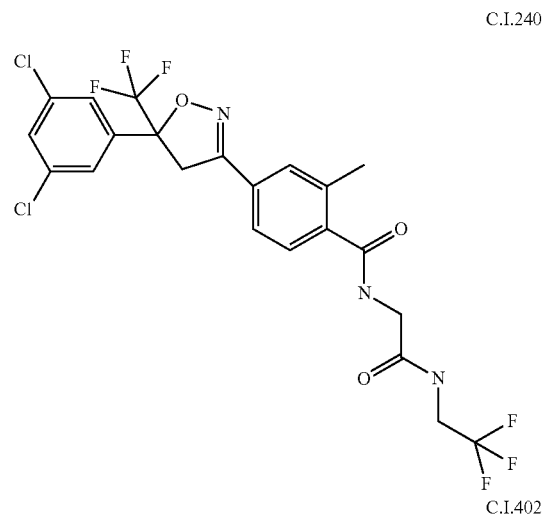

C.I.240

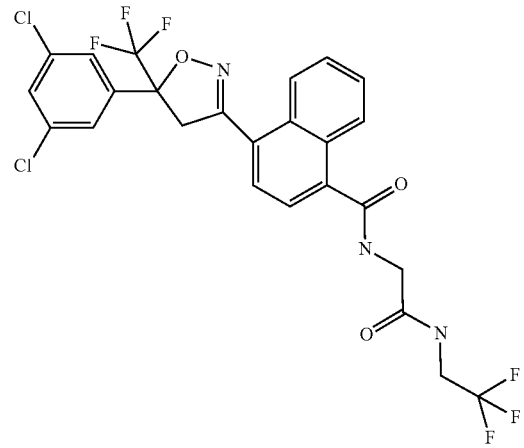

C.I.402

TABLE B.1.1

Fungicidal test example 1: Phytin

| Active compound/ active mixture | Concentration (ppm) | Mixture | Observed efficacy | Calculated efficacy according to Colby (%) | Synergism (%) |
|---|---|---|---|---|---|
| C.I.240 | 16 | — | 15 | | |
| | 4 | — | 6 | | |
| Pyraclostrobin | 0.016 | — | 13 | | |
| Chlorothalonil | 1 | — | 53 | | |

TABLE B.1.1-continued

Fungicidal test example 1: Phytin

| Active compound/ active mixture | Concentration (ppm) | Mixture | Observed efficacy | Calculated efficacy according to Colby (%) | Synergism (%) |
|---|---|---|---|---|---|
| C.I.240 | 4 | 250:1 | 38 | 18 | 20 |
| Pyraclostrobin | 0.016 | | | | |
| C.I.240 | 16 | 16:1 | 100 | 60 | 40 |
| Chlorothalonil | 1 | | | | |

TABLE B.1.2

Fungicidal test example 2: Botrci

| Active compound/ active mixture | Concentration (ppm) | Mixture | Observed efficacy | Calculated efficacy according to Colby (%) | Synergism (%) |
|---|---|---|---|---|---|
| C.I.240 | 16 | — | 18 | | |
| | 0.063 | — | 0 | | |
| Fenhexamid | 0.016 | — | 51 | | |
| Chlorothalonil | 1 | — | 43 | | |
| C.I.240 | 0.063 | 4:1 | 91 | 51 | 40 |
| Fenhexamid | 0.016 | | | | |
| C.I.240 | 16 | 16:1 | 98 | 53 | 45 |
| Chlorothalonil | 1 | | | | |

TABLE B.1.3

Fungicidal test example 3: Pyrior

| Active compound/ active mixture | Concentration (ppm) | Mixture | Observed efficacy | Calculated efficacy according to Colby (%) | Synergism (%) |
|---|---|---|---|---|---|
| C.I.240 | 4 | | 11 | | |
| | 1 | | 0 | | |
| C.I.402 | 4 | | 35 | | |
| | 1 | | 6 | | |
| Trifloxystrobin | 0.063 | | 32 | | |
| Picoxystrobin | 0.063 | | 60 | | |
| Carbendazim | 0.25 | | 18 | | |
| Pyraclostrobin | 0.004 | | 26 | | |
| Mancozeb | 1 | | 36 | | |
| Epoxiconazol | 0.063 | | 0 | | |
| Iprodion | 0.24 | | 4 | | |
| C.I.240 | 1 | 16:1 | 61 | 32 | 29 |
| Trifloxystrobin | 0.063 | | | | |
| C.I.240 | 4 | 64:1 | 85 | 64 | 21 |
| Picoxystrobin | 0.063 | | | | |
| C.I.240 | 4 | 16:1 | 61 | 27 | 34 |
| Carbendazim | 0.25 | | | | |
| C.I.402 | 4 | 16:1 | 75 | 36 | 39 |
| Trifloxystrobin | 0.25 | | | | |
| C.I.402 | 4 | 64:1 | 96 | 74 | 22 |
| Picoxystrobin | 0.063 | | | | |
| C.I.402 | 1 | 250:1 | 78 | 31 | 47 |
| Pyraclostrobin | 0.004 | | | | |
| C.I.402 | 4 | 4:1 | 66 | 37 | 29 |
| Mancozeb | 1 | | | | |
| C.I.402 | 4 | 64:1 | 74 | 35 | 39 |
| Epoxiconazol | 0.063 | | | | |
| C.I.402 | 4 | 16:1 | 89 | 46 | 43 |
| Carbendazim | 0.25 | | | | |
| C.I.402 | 4 | 16:1 | 64 | 38 | 26 |
| Iprodion | 0.25 | | | | |

TABLE B.1.4

Fungicidal test example 4: Septtr

| Active compound/ active mixture | Concentration (ppm) | Mixture | Observed efficacy | Calculated efficacy according to Colby (%) | Synergism (%) |
|---|---|---|---|---|---|
| C.I.240 | 4 | — | 0 | | |
| C.I.402 | 63 | — | 0 | | |
| | 4 | — | 2 | | |
| Azoxystrobin | 0.063 | — | 56 | | |
| Fluoxastrobin | 0.25 | — | 68 | | |
| Fubenthiavalicarb (Benthivalicarb) | 4 | — | 0 | | |
| C.I.240 | 4 | 64:1 | 75 | 56 | 19 |
| Azoxystrobin | 0.063 | | | | |
| C.I.402 | 4 | 16:1 | 92 | 69 | 23 |
| Fluoxastrobin | 0.25 | | | | |
| C.I.402 | 63 | 16:1 | 23 | 0 | 23 |
| Flubenthiavalicarb (Benthivalicarb) | 4 | | | | |

B.2. Pesticidal Action Against Animal Pests

The following tests are suitable for demonstrating the control efficacy of mixtures on specific animal pests. However, the pest control protection afforded by the mixtures is not limited to these species. In certain instances, combinations of a compounds I of formula I of this invention with other pest control compounds or agents can be found to exhibit synergistic effects against certain important invertebrate pests.

The analysis of synergism or antagonism between the mixtures or compositions can also be determined using Colby's equation.

Insecticidal Test Example 1:
Activity Against Vetch Aphid (*Megoura viciae*)

For evaluating control of vetch aphid (*Megoura viciae*) through contact or systemic means the test unit consists of -microtiter plates containing broad bean leaf disks. The mixtures are formulated using a solution containing 75 wt % water and 25 wt % DMSO. Different concentrations of formulated mixtures are sprayed onto the leaf disks at 2.5 µl, using a custom built micro atomizer, at two replications.

For experimental mixtures in these tests identical volumes of both mixing partners at the desired concentrations respectively, are mixed together.

After application, the leaf disks are air-dried and 5-8 adult aphids are placed on the leaf disks inside the microtiter plate wells. The aphids are then allowed to suck on the treated leaf disks and are incubated at 23±1° C. and 50±5% room humidity for 5 days. Aphid mortality and fecundity is then visually assessed.

Insecticidal Test Example 2:
Activity Against Bird Cherry Aphid (*Rhopalosiphum padi*)

For evaluating control of bird cherry aphid (*Rhopalosiphum padi*) through contact or systemic means the test unit consists of microtiter plates containing barley leaf disks. The mixtures are formulated using a solution containing 75 wt % water and 25 wt % DMSO. Different concentrations of formulated mixtures are sprayed onto the leaf disks at 2.5 µl, using a custom built micro atomizer, at two replications.

For experimental mixtures in these tests identical volumes of both mixing partners at the desired concentrations respectively, are mixed together.

After application, the leaf disks are air-dried and 5-8 adult aphids placed on the leaf disks inside the microtiter plate wells. The aphids are then allowed to suck on the treated leaf disks and incubated at 25±1° C. and 80±5% room humidity for 3 to 5 days. Aphid mortality and fecundity is then visually assessed.

Insecticidal Test Example 3:
Activity Against Green Peach Aphid (*Myzus persicae*)

For evaluating control of green peach aphid (*Myzus persicae*) through systemic means the test unit consists of well-Microtiter plates containing liquid artificial diet under an artificial membrane.

The mixtures are formulated using a solution containing 75 wt % water and 25 wt % DMSO. Different concentrations of formulated mixtures are pipetted into the aphid diet, using a custom built pipetter, at two replications.

For experimental mixtures in these tests identical volumes of both mixing partners at the desired concentrations respectively, are mixed together.

After application, 5-8 adult aphids are placed on the artificial membrane inside the microtiter plate wells. The aphids are then allowed to suck on the treated aphid diet and incubated at 23±1° C. and 50±5% room humidity for 3 days. Aphid mortality and fecundity is then visually assessed.

Insecticidal Test Example 4:
Activity Against Boll Weevil (*Anthonomus grandis*)

For evaluating control of boll weevil (*Anthonomus grandis*) the test unit consists of well-microtiter plates containing an insect diet and 20-30 *A. grandis* eggs.

The mixtures are formulated using a solution containing 75 wt % water and 25 wt % DMSO. Different concentrations of formulated mixtures are sprayed onto the insect diet at 20 µl, using a custom built micro atomizer, at two replications.

For experimental mixtures in these tests identical volumes of both mixing partners at the desired concentrations respectively, are mixed together.

After application, microtiter plates are incubated at 23±1° C. and 50±5% room humidity for 5 days. Egg and larval mortality is then visually assessed.

Insecticidal Test Example 5:
Activity Against Mediterranean Fruitfly (*Ceratitis capitata*)

For evaluating control of Mediterranean fruitfly (*Ceratitis capitata*) the test unit consists of well-microtiter plates containing an insect diet and 50-80 *C. capitata* eggs.

The mixtures are formulated using a solution containing 75 wt % water and 25 wt % DMSO. Different concentrations of formulated mixtures are sprayed onto the insect diet at 5 µl, using a custom built micro atomizer, at two replications.

For experimental mixtures in these tests identical volumes of both mixing partners at the desired concentrations respectively, are mixed together.

After application, microtiter plates are incubated at 28±1° C. and 80±5% room humidity for 5 days. Egg and larval mortality is then visually assessed.

Insecticidal Test Example 6:
Activity Against Tobacco Budworm (*Heliothis virescens*)

For evaluating control of tobacco budworm (*Heliothis virescens*) the test unit consists of well-microtiter plates containing an insect diet and 15-25 *H. virescens* eggs.

The mixtures are formulated using a solution containing 75 wt % water and 25 wt % DMSO. Different concentrations of formulated mixtures are sprayed onto the insect diet at 10 µl, using a custom built micro atomizer, at two replications.

For experimental mixtures in these tests identical volumes of both mixing partners at the desired concentrations respectively, are mixed together.

After application, microtiter plates are incubated at 28±1° C. and 80±5% room humidity for 5 days. Egg and larval mortality is then visually assessed.

The invention claimed is:
1. A pesticidal mixture comprising at least two active compounds,
wherein:
1) at least one active compound I is a isoxazoline compound of the formula (I)

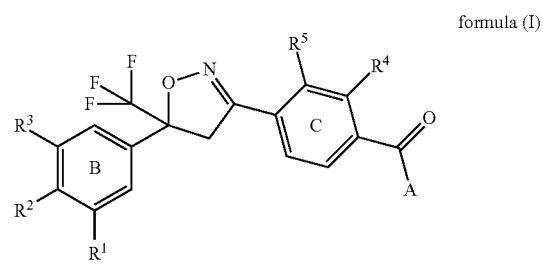

wherein
A is

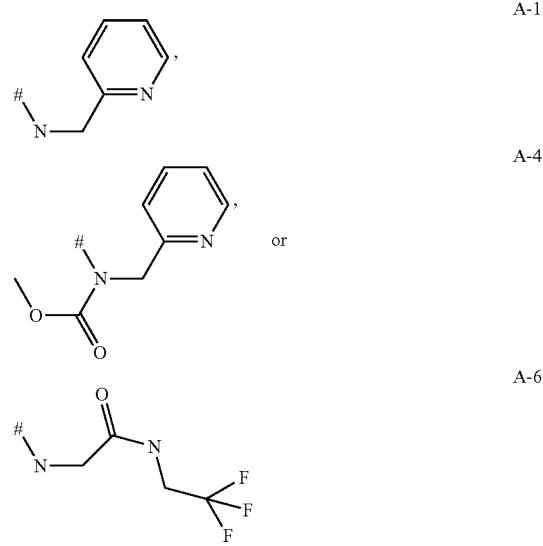

and wherein #denotes the bond in formula I;
$R^1$, $R^3$ are independently from one another selected from the group consisting of hydrogen, chloro and $CF_3$;
$R^2$ is hydrogen or chloro;
$R^4$ is hydrogen or $CH_3$,
$R^5$ is hydrogen,
or
$R^4$ and $R^5$ are together a bridging 1,3-butadienyl group, which form—together with the aromatic phenylring C they are attached to—a naphthyl ring;
or the tautomers, enantiomers, diastereomers or salts thereof,
and
2) at least one active compound II is a fungicidal compound selected from the groups IIA to IIF:
IIA an azole selected from the group consisting of triazoles, imidazoles, pyrazoles, thiazoles and oxazoles selected from the group consisting of benomyl, carbendazim, difenoconazole, epoxiconazole, fluquinconazole, flusilazole, flutriafol, metconazole, prochloraz, prothioconazole, tebuconazole, and triticonazole;

IIB a strobilurin selected from the group consisting of azoxystrobin, dimoxystrobin, fluoxastrobin, kresoxim-methyl, orysastrobin, picoxystrobin, pyraclostrobin, and trifloxystrobin;

IIC a carboxamide selected from the group consisting of bixafen, boscalid, carpropamid, dimethomorph, fenhexamid, fluopyram, flumorph, fluopicolide (picobenzamid), mandipropamid, metalaxyl, mefenoxam, ofurace, penthiopyrad, and zoxamide;

IID a heterocyclic compound selected from the group consisting of dodemorph, famoxadone, fenpropidin, fenpropimorph, proquinazid, pyrimethanil, quinoxyfen, tridemorph, vinclozolin, and 5-chloro-7-(4-methylpiperidin-1-yl)-6-(2,4,6-trifluorophenyl)-[1,2,4]triazolo[1,5-a]pyrimidine;

IIE a carbamate selected from the group consisting of flubenthiavalicarb, iprovalicarb, mancozeb, maneb, metiram, and thiram;

IIF a fungicide selected from
the group of sulfur-containing heterocyclyl compounds comprising dithianon;
the group of organophosphorus compounds comprising fosetyl-aluminum, and phosphorous acid and its salts;
the group of organochlorine compounds comprising chlorothalonil, flusulfamide, and thiophanate-methyl;

wherein the compound of formula (I) and compound II are present in a weight ratio of 500:1 to 1:100.

2. The pesticidal mixture according to claim 1 comprising additionally one or more further insecticidal compound III.

3. The pesticidal mixture according to claim 1, wherein the substituents of the compound I of formula (I) have the following meanings:
A is A-1, A-4 or A-6;
$R^1$, $R^3$ are independently from one another selected from the group consisting of hydrogen, chloro and $CF_3$;
$R^2$ is hydrogen or chloro;
$R^4$ is hydrogen or $CH_3$,
$R^5$ is hydrogen
or
$R^4$ and $R^5$ are together a bridging 1,3-butadienyl group, which form—together with the aromatic phenylring C they are attached to—a naphthyl ring;
or the tautomers, enantiomer, diastereomer or salts thereof.

4. The pesticidal mixture according to claim 1, wherein the substituents of the compound I of formula (I) have the following meanings:
A is A-1, A-4 or A-6;
$R^1$, $R^2$, $R^3$ are chloro;
$R^4$ or is hydrogen $CH_3$,
$R^5$ is hydrogen
or
$R^4$ and $R^5$ are together a bridging 1,3-butadienyl group, which form—together with the aromatic phenylring C they are attached to—a naphthyl ring;
or the tautomers, enantiomers, diastereomers or salts thereof.

5. The pesticidal mixture according to claim 1, wherein the substituents of the compound I of formula (I) have the following meanings:
A is A-1, A-4 or A-6;
$R^1$, $R^3$ are chloro;
$R^2$ is hydrogen;
$R^4$ is hydrogen or $CH_3$,
$R^5$ is hydrogen
or
$R^4$ and $R^5$ are together a bridging 1,3-butadienyl group, which form—together with the aromatic phenylring C they are attached to—a naphthyl ring;
or the tautomers, enantiomers, diastereomers or salts thereof.

6. The pesticidal mixture according to claim 1, wherein the substituents of the compound I of formula (I) have the following meanings:
A is A-6;
$R^1$, $R^3$ are chloro;
$R^2$ is hydrogen;
$R^4$ is $CH_3$,
$R^5$ is hydrogen
or
$R^4$ and $R^5$ are together a bridging 1,3-butadienyl group, which form—together with the aromatic phenylring C they are attached to—a naphthyl ring;
or the tautomers, enantiomers, diastereomers or salts thereof.

7. The pesticidal mixture according to claim 1, wherein the substituents of the compound I of formula (I) have the following meanings:
A is A-1, A-4 or A-6;
$R^1$, $R^3$ are $CF_3$;
$R^2$ is hydrogen;
$R^4$ is hydrogen or $CH_3$,
$R^5$ is hydrogen
or
$R^4$ and $R^5$ are together a bridging 1,3-butadienyl group, which form—together with the aromatic phenylring C they are attached to—a naphthyl ring;
or the tautomers, enantiomers, diastereomers or salts thereof.

8. The pesticidal mixture according to claim 1, wherein the substituents of the active compound I of formula I have the following meanings:
A is A-1, A-4 or A-6;
$R^1$ is $CF_3$;
$R^2$, $R^3$ are hydrogen;
$R^4$ is hydrogen or $CH_3$,
$R^5$ is hydrogen
or
$R^4$ and $R^5$ are together a bridging 1,3-butadienyl group, which form—together with the aromatic phenylring C they are attached to—a naphthyl ring;
or the tautomers, enantiomers, diastereomers or salts thereof.

9. The pesticidal mixture according to claim 1, comprising a compound I of the formula (I) and a compound II in a weight ratio of from 100:1 to 1:100.

10. The pesticidal mixture according to claim 1, comprising an active compound II selected from the group II.A of azoles consisting of benomyl, carbendazim, epoxiconazole, fluquinconazole, flutriafol, flusilazole, metconazole, prochloraz, prothioconazole, tebuconazole and triticonazole.

11. The pesticidal mixture according to claim 1, comprising an active compound II selected from the group consisting of picoxystrobin, pyraclostrobin and trifloxystrobin.

12. The pesticidal mixture according to claim 1, comprising an active compound II selected from the group consisting of boscalid, dimethomorph, fenhexamid and penthiopyrad.

13. The pesticidal mixture according to claim 1, comprising an active compound II selected from the group consisting of dodemorph, famoxadone, fenpropimorph, iprodione, proquinazid, pyrimethanil, tridemorph and 5-chloro-7-(4-methylpiperidin-1-yl)-6-(2,4,6-trifluorophenyl)-[1,2,4]triazolo[1,5-a]pyrimidine.

14. The pesticidal mixture according to claim 1, comprising an active compound II selected from the group consisting of maneb, mancozeb, metiram and thiram.

15. The pesticidal mixture according to claim 1, comprising an active compound II selected from the group consisting of chlorothalonil, dithianon, flusulfamide, metrafenone and phosphorous acid and its salts.

16. A ternary or quaternary pesticidal mixture according to claim 1, comprising two active compounds II.

17. A pesticidal composition, comprising a liquid or solid carrier and a mixture of at least one active compound I and at least one active compound II according to claim 1.

18. A method for controlling phytopathogenic harmful fungi, wherein the fungi, their habitat or the plants to be protected against fungal attack, the soil or seed are treated with an effective amount of a mixture of at least one active compound I and at least one active compound II according to claim 1.

19. A method for protecting plants from phytopathogenic harmful fungi, wherein the fungi, their habitat or the plants to be protected against fungal attack, the soil or seed are treated with an effective amount of a mixture of at least one active compound I and at least one active compound II according to claim 1.

20. A method according to claim 18, wherein the mixture is applied in an amount of from 5 g/ha to 2000 g/ha.

21. A method for protection of seed comprising contacting the seeds with an effective amount of a mixture of at least one active compound I and at least one active compound II according to claim 1.

22. A method according to claim 21 wherein the mixture of the active compound I and the active compound II is applied in an amount of from 0.001 g to 10 kg per 100 kg of seeds.

23. A seed treated with the mixture of at least one active compound I and at least one active compound II according to claim 1 in an amount of from 0.1 g to 10 kg per 100 kg of seeds.

24. A method according to claim 18, wherein the active compound I and the active compound II are applied simultaneously, that is jointly or separately, or in succession.

* * * * *

UNITED STATES PATENT AND TRADEMARK OFFICE
CERTIFICATE OF CORRECTION

PATENT NO.       : 8,597,688 B2                                    Page 1 of 1
APPLICATION NO.  : 13/003032
DATED            : December 3, 2013
INVENTOR(S)      : Karsten Koerber et al.

It is certified that error appears in the above-identified patent and that said Letters Patent is hereby corrected as shown below:

In the Claims

Claim 1, col. 65, line 12, after "fenpropimorph," insert --iprodione--.

Claim 4, col. 65, line 51, after "$R^4$" delete "or"; and after "hydrogen" insert --or--.

Signed and Sealed this
Fourteenth Day of October, 2014

Michelle K. Lee
*Deputy Director of the United States Patent and Trademark Office*